(12) United States Patent
Schultz et al.

(10) Patent No.: US 6,768,107 B2
(45) Date of Patent: Jul. 27, 2004

(54) INTEGRATED MONOLITHIC MICROFABRICATED DISPENSING NOZZLE AND LIQUID CHROMATOGRAPHY-ELECTROSPRAY SYSTEM AND METHOD

(75) Inventors: Gary A. Schultz, Ithaca, NY (US); Thomas N. Corso, Lansing, NY (US)

(73) Assignees: Advion BioSciences, Inc., Ithaca, NY (US); Kionix, Inc., Ithaca, NY (US)

(*) Notice: Subject to any disclaimer, the term of this patent is extended or adjusted under 35 U.S.C. 154(b) by 0 days.

(21) Appl. No.: 10/426,455

(22) Filed: Apr. 30, 2003

(65) Prior Publication Data

US 2004/0016878 A1 Jan. 29, 2004

Related U.S. Application Data

(62) Division of application No. 09/468,535, filed on Dec. 20, 1999, now Pat. No. 6,633,031.
(60) Provisional application No. 60/122,972, filed on Mar. 2, 1999.

(51) Int. Cl.[7] .......................... H01J 49/04; H01J 49/26; B01D 59/44
(52) U.S. Cl. ...................... 250/288; 250/281; 250/282; 250/423 R; 210/198.2; 210/748; 430/313; 430/320
(58) Field of Search ................... 250/288, 281, 250/282, 423 R; 210/198.2, 748; 430/313, 320

(56) References Cited

U.S. PATENT DOCUMENTS

| | | |
|---|---|---|
| 3,150,442 A | 9/1964 | Straw et al. |
| 3,538,744 A | 11/1970 | Karasek et al. |
| 3,669,881 A | 6/1972 | Cremer et al. |
| 3,738,759 A | 6/1973 | Diurich et al. |
| 3,915,652 A | 10/1975 | Natelson |

(List continued on next page.)

FOREIGN PATENT DOCUMENTS

| | | |
|---|---|---|
| DE | 43 18 407 A1 | 6/1993 |
| EP | 0 677 322 A2 | 10/1995 |
| EP | 677332 A2 | 10/1995 |
| EP | 259796 B1 | 1/1996 |
| EP | 692713 A1 | 1/1996 |

(List continued on next page.)

OTHER PUBLICATIONS

Knox, "Theoretical Aspects of LC with Packed and Open Small–Bors Columns," *Journal of Chromatographic Science* 18:453–461 (1980).

(List continued on next page.)

*Primary Examiner*—Nikita Wells
(74) *Attorney, Agent, or Firm*—Holme Roberts & Owen LLP

(57) ABSTRACT

A droplet/electrospray device and a liquid chromatography-electrospray system are disclosed. The droplet/electrospray device comprises a substrate defining a channel between an entrance orifice on an injection surface and an exit orifice on an ejection surface, a nozzle defined by a portion recessed from the ejection surface surrounding the exit orifice, and an electrode for application of an electric potential to the substrate to optimize and generate droplets or an electrospray. A plurality of these electrospray devices can be used in the form of an array of miniaturized nozzles. The liquid chromatography-electrospray device comprises a separation substrate defining an introduction channel between an entrance orifice and a reservoir and a separation channel between the reservoir and an exit orifice, the separation channel being populated with separation posts perpendicular to the fluid flow. A cover substrate is bonded to the separation substrate to enclose the reservoir and the separation channel adjacent the cover substrate. The exit orifice of the liquid chromatography device is homogeneously interfaced with the entrance orifice of the electrospray device to form an integrated single system. Procedures for fabrication of the electrospray devices of the present invention are also disclosed.

11 Claims, 59 Drawing Sheets

U.S. PATENT DOCUMENTS

| | | |
|---|---|---|
| 3,921,916 A | 11/1975 | Bassous |
| 4,007,464 A | 2/1977 | Bassous et al. |
| 4,056,324 A | 11/1977 | Göhde |
| 4,092,166 A | 5/1978 | Olsen et al. |
| 4,209,696 A | 6/1980 | Fite |
| 4,356,722 A | 11/1982 | Bunce et al. |
| 4,366,118 A | 12/1982 | Bunce et al. |
| 4,369,664 A | 1/1983 | Bunce et al. |
| 4,403,234 A | 9/1983 | Miura et al. |
| 4,437,103 A | 3/1984 | Ikeda |
| 4,459,267 A | 7/1984 | Bunce et al. |
| 4,480,259 A | 10/1984 | Kruger et al. |
| 4,489,259 A | 12/1984 | White et al. |
| 4,490,728 A | 12/1984 | Vaught et al. |
| 4,590,482 A | 5/1986 | Hay et al. |
| 4,593,728 A | 6/1986 | Whitehead et al. |
| 4,683,042 A | 7/1987 | Scott |
| 4,708,782 A | 11/1987 | Andresen et al. |
| 4,728,392 A | 3/1988 | Miura et al. |
| 4,733,823 A | 3/1988 | Waggener et al. |
| 4,842,701 A | 6/1989 | Smith et al. |
| 4,879,097 A | 11/1989 | Whitehead et al. |
| 4,891,120 A | 1/1990 | Sethi et al. |
| 4,908,112 A | 3/1990 | Pace |
| 4,983,038 A | 1/1991 | Ohki et al. |
| 4,999,493 A | 3/1991 | Allen et al. |
| 5,015,845 A | 5/1991 | Allen et al. |
| 5,110,745 A | 5/1992 | Kricka et al. |
| 5,126,022 A | 6/1992 | Soane et al. |
| 5,132,012 A | 7/1992 | Miura et al. |
| 5,162,650 A | 11/1992 | Bier et al. |
| 5,180,480 A | 1/1993 | Manz |
| 5,182,366 A | 1/1993 | Huebner et al. |
| 5,245,185 A | 9/1993 | Busch et al. |
| 5,269,900 A | 12/1993 | Jorgenson et al. |
| 5,283,036 A | 2/1994 | Hofmann et al. |
| 5,294,426 A | 3/1994 | Sekine et al. |
| 5,296,114 A | 3/1994 | Manz |
| 5,296,375 A | 3/1994 | Kricka et al. |
| 5,302,533 A | 4/1994 | Kricka |
| 5,304,487 A | 4/1994 | Wilding et al. |
| 5,306,621 A | 4/1994 | Kricka |
| 5,316,680 A | 5/1994 | Frechet et al. |
| 5,328,578 A | 7/1994 | Gordon |
| 5,331,159 A | 7/1994 | Apffel, Jr. et al. |
| 5,332,481 A | 7/1994 | Guttman |
| 5,334,310 A | 8/1994 | Frechet et al. |
| 5,338,427 A | 8/1994 | Sharde et al. |
| 5,349,186 A | 9/1994 | Ikonomou et al. |
| 5,374,834 A | 12/1994 | Geis et al. |
| 5,376,252 A | 12/1994 | Ekstrom et al. |
| 5,387,329 A | 2/1995 | Foos et al. |
| 5,401,376 A | 3/1995 | Foos et al. |
| 5,401,963 A | 3/1995 | Sittler |
| 5,415,841 A | 5/1995 | Dovichi et al. |
| 5,421,980 A | 6/1995 | Guttman |
| 5,423,964 A | 6/1995 | Smith et al. |
| 5,427,946 A | 6/1995 | Kricka et al. |
| 5,429,734 A | 7/1995 | Gajar et al. |
| 5,431,807 A | 7/1995 | Frechet et al. |
| 5,445,324 A | 8/1995 | Berry et al. |
| 5,453,185 A | 9/1995 | Frechet et al. |
| 5,481,110 A | 1/1996 | Krishnaswamy et al. |
| 5,486,335 A | 1/1996 | Wilding et al. |
| 5,493,115 A | 2/1996 | Deinzer et al. |
| 5,495,108 A | 2/1996 | Apffel, Jr. et al. |
| 5,498,392 A | 3/1996 | Wilding et al. |
| 5,501,883 A | 3/1996 | Ishikawa et al. |
| 5,501,893 A | 3/1996 | Laermer et al. |
| 5,505,832 A | 4/1996 | Laukien et al. |
| 5,512,131 A | 4/1996 | Kumar et al. |
| 5,512,451 A | 4/1996 | Kricka |
| 5,523,566 A | 6/1996 | Fuerstenau et al. |
| 5,536,939 A | 7/1996 | Freidhoff et al. |
| 5,541,408 A | 7/1996 | Sittler |
| 5,563,639 A | 10/1996 | Cameron et al. |
| 5,572,023 A | 11/1996 | Caprioli |
| 5,608,217 A | 3/1997 | Franzen et al. |
| 5,640,010 A | 6/1997 | Twerenbold |
| 5,641,400 A | 6/1997 | Kaltenbach et al. |
| 5,644,131 A | 7/1997 | Hansen |
| 5,647,979 A | 7/1997 | Liao et al. |
| 5,652,427 A | 7/1997 | Whitehouse et al. |
| 5,705,813 A | 1/1998 | Apffel et al. |
| 5,716,825 A | 2/1998 | Hancock et al. |
| 5,747,815 A | 5/1998 | Young et al. |
| 5,750,988 A | 5/1998 | Apffel et al. |
| 5,779,868 A | 7/1998 | Parce et al. |
| 5,789,746 A | 8/1998 | Kato et al. |
| 5,800,692 A | 9/1998 | Naylor et al. |
| 5,804,022 A | 9/1998 | Kaltenbach et al. |
| 5,856,082 A | 1/1999 | Aebersold et al. |
| 5,872,010 A | 2/1999 | Karger et al. |
| 5,876,957 A | 3/1999 | Douglas et al. |
| 5,877,495 A | 3/1999 | Takada et al. |
| 5,917,184 A | 6/1999 | Carson et al. |
| 5,917,185 A | 6/1999 | Yeung et al. |
| 5,969,351 A | 10/1999 | Nabeshima et al. |
| 5,969,353 A | 10/1999 | Hsieh |
| 5,972,187 A | 10/1999 | Parce et al. |
| 5,993,633 A | 11/1999 | Smith et al. |
| 5,994,696 A | 11/1999 | Tai et al. |
| 6,005,245 A | 12/1999 | Sakairi et al. |
| 6,007,775 A | 12/1999 | Yager |
| 6,032,876 A | 3/2000 | Bertsch et al. |
| 6,060,705 A | 5/2000 | Whitehouse et al. |
| 6,066,848 A | 5/2000 | Kassel et al. |
| 6,068,749 A | 5/2000 | Karger et al. |
| 6,110,343 A | 8/2000 | Ramsey et al. |
| 6,114,693 A | 9/2000 | Hirabayashi et al. |
| 6,171,875 B1 | 1/2001 | Silverbrook |
| 6,245,227 B1 | 6/2001 | Moon et al. |
| 6,394,942 B2 | 5/2002 | Moon et al. |
| 6,417,510 B2 | 7/2002 | Moon et al. |
| 6,432,311 B2 | 8/2002 | Moon et al. |
| 6,454,938 B2 | 9/2002 | Moon et al. |
| 6,461,516 B2 | 10/2002 | Moon et al. |
| 6,464,866 B2 | 10/2002 | Moon et al. |
| 6,596,988 B2 * | 7/2003 | Corso et al. ............. 250/288 |
| 6,627,882 B2 * | 9/2003 | Schultz et al. ............. 250/288 |
| 6,633,031 B1 * | 10/2003 | Schultz et al. ............. 250/288 |
| 2001/0001455 A1 | 5/2001 | Moon et al. |
| 2001/0001460 A1 | 5/2001 | Moon et al. |
| 2001/0037979 A1 | 11/2001 | Moon et al. |
| 2002/0123153 A1 | 9/2002 | Moon et al. |
| 2002/0158027 A1 | 10/2002 | Moon et al. |
| 2002/0172618 A1 | 11/2002 | Moon et al. |
| 2002/0172619 A1 | 11/2002 | Moon et al. |

FOREIGN PATENT DOCUMENTS

| | | |
|---|---|---|
| EP | 0 637 998 B1 | 7/1996 |
| EP | 0 639 223 B1 | 7/1996 |
| EP | 565027 B1 | 3/1997 |
| EP | 860858 A1 | 8/1998 |
| EP | 588952 B1 | 9/1999 |
| EP | 964428 A2 | 12/1999 |
| EP | 966022 A2 | 12/1999 |
| GB | 2260282 | 4/1993 |
| GB | 2287356 A | 9/1995 |
| WO | WO 92/03720 | 3/1992 |
| WO | WO 93/22053 | 11/1993 |

| WO | WO 93/22055 | 11/1993 |
| WO | WO 96/04547 | 2/1996 |
| WO | WO 96/14933 | 5/1996 |
| WO | WO 96/14934 | 5/1996 |
| WO | WO 96/15269 | 5/1996 |
| WO | WO 97/04297 | 2/1997 |
| WO | WO 00/15321 | 3/2000 |
| WO | WO 01/50499 A1 | 7/2001 |
| WO | WO 01/53819 A1 | 7/2001 |

OTHER PUBLICATIONS

Alexander et al., "Development of a Nano–electrospray Mass Spectrometry Source for Nanoscale Liquid Chromatography and Sheathless Capillary Electrophoresis," *Rapid Communications in Mass Spectrometry* 12:1187–1191 (1998).

Dole et al., "Molecular Beams of Macroions," *The Journal of Chemical Physics* 49:2240–2249 (1968).

Yamashita et al., "Electrospray Ion Source. Another Variation on the Free–Jet Theme," *The Journal of Physical Chemistry* 88(20):4451–4459 (1984).

David P.H. Smith, "The Electrohydrodynamic Atomization of Liquids," *IEEE Transactions on Industry Applications* IA–22(3):527–535 (1980).

Harrison et al., "Micromachining a Miniaturized Capillary Electrophoresis–Based Chemical Analysis System on a Chip," *Science* 261:895–897 (1993).

Jacobson et al., "Open Channel Electrochromatography on a Microchip," *Anal. Chem.* 66:2369–2373 (1994).

Kumer et al., "Integrated Microchip Device with Electrokinetically Controlled Solvent Mixing for Isocratio and Gradient Elution in Micellar Electrokinetic Chromatography," *Anal. Chem.* 69:5165–5171 (1997).

He et al., "Fabrication of Nanocolumns for Liquid Chromatography," *Anal. Chem.* 70:3790–3797 (1998).

Wilm et al., "Electrospray and Taylor–ConeTheory, Dole's Beam of Macromolecules at Last?" *International Journal of Mass Spectrometry and Ion Processes* 136:167–180 (1994).

Gale et al., "Small volume and Low Flow–rate Electrospray Ionization Mass Spectrometry of Aqueous Samples," *Rapid Communications in Mass Spectrometry* , 7:1017–1021 (1993).

Ramsey et al., "Generating Electrospray from Microchip Devices Using Electroosmotic Pumping," *Anal. Chem.* 69:1174–1178 (1997).

Xue et al., "Multichannel Microchip Electrospray Mass Spectrometry," *Anal. Chem.* 69:426–490 (1997).

Dasai et al., "A MEMS Electrospray Nozzle for Mass Spectroscopy," 1997 Int. Conference on Solid State Sensors and Actuators, Chicago, pp. 927–930 (Jun. 16–19, 1997).

Jacobson et al., "High–Speed Separations on a Microchip," *Anal. Chem.* 66:1114–1118 (1994).

Wang et al., "Polymer–Based Electrospray Chips for Mass Spectrometry," Twelfth IEEE International Conference on Micro Electro Mechanical Systems, Orlando, Florida, pp. 523–528 (1999).

Laermer et al., "Bosch Deep Silicon Etching: Improving Uniformity and Etch Rate for Advanced Mems Applications," Twelfth IEEE International Conference on Micro Electro Mechanical Systems, Orlando, Florida, pp. 211–216 (1999).

Wilm, et al., "Analytical Properties of the Nanoelectrospray Ion Source," *Anal. Chem.*, 68:1–8 (1996).

*Electrospray Ionization Mass Spectrometry: Fundamentals, Instrumentation, and Applications*, ed. R.B. Cole, ISBN 0–471–14564–5, New York, New YorkJohn Wiley & Sons, Inc., pp. 3–63 (1997).

Figeys et al., "A Microfabricated Device for Rapid Protein Identification by Microelectrospray Ion Trap Mass Spectrometry," *Anal. Chem.*, 69:3153–3160 (1997).

Vanhoutte et al., "Development of a Nanoscale Liquid Chromatography/Electrospray Mass Spectrometry Methodology for the Detection and Identification of DNA Adducts," *Anal. Chem.*, 69:3161–3168 (1997).

Beavis et al., "Off–Line Coupling of a Microbore High–Performance Liquid Chromatograph to a Secondary Ion Time–of–Flight Mass Spectrometry," *Anal. Chem.*, 62:1259–1264 (1990).

Burggraf et al., "Synchronized Cyclic Capillary Electrophoresis—A Novel Approach to Ion Separation in Solutions," *J. High Resol. Chromatogr.*, 16:594–596 (1993).

Cheng et al., "Chip PCR. II. Investigation of Different PCR Amplification Systems in Microfabricated Silicon–Glass Chips," *Nucleic Acids Res.*, 24(2):380–385 (1996).

Chu et al., "Affinity Capillary Electrophoresis—Mass Spectrometry for Screening Combinatorial Libraries," *J. Am. Chem. Soc.*, pp. 7827–7835 (1996).

Cowen et al., "As On–Chip Miniature Liquid Chromatography System: Design, Construction and Characterization," *Micro Total Analysis Systems*, pp. 295–298 (1995).

Davis et al., "A Microscale Electrospray Interface for On–Line, Capillary Liquid Chromatography/Tandem Mass Spectrometry of Complex Peptide Mixtures," *Anal. Chem.*, 67:4549–4556 (1993).

Deml et al., "Electric Sample Splitter for Capillary Zone Electrophoresis," *J. Chromatogr.*, 320:159–165 (1985).

Doherty et al., "Rapid On–Line Analysis Using a Micromachined Gas Chromatograph Coupled to a Bench–Top Quadrupole Mass Spectrometer," *LC–GC*, 12(11):846–850 (1994).

Effenhauser et al., "High–Speed Separation of Antisense Oligonucleotides on a Micromachined Capillary Electrophoresis Device," *Anal. Chem.*, 66:2949–2953 (1994).

Effenhauser et al., "Glass Chips for High–Speed Capillary Electrophoresis Separations with Submicrometer Plane Heights," *Anal. Chem.*, 65:2637–2642 (1993).

Effenhauser et al., "Manipulation of Sample Fractions on a Capillary Electrophoresis Chip," *Anal. Chem.*, 67(13):2284–2287 (1995).

Elwenspoek et al., "Silicon Microstructures for Fluid Handling," *Analysis Magazine*, pp. 1–4 (1994).

Emmett et al., "Micro–Electrospray Mass Spectrometry: Ultra–High–Sensitivity Analysis of Peptides and Proteins," *J. Am. Soc. Mass Spectrom.*, 5:605–613 (1994).

Fan et al., "Micromachining of Capillary Electrophoresis Injectors and Separators on Glass Chips and Evaluation of Flow at Capillary Intersections," *Anal. Chem.*, 66:177–184 (1994).

Fang et al., "On–Line Time–of–Flight Mass Spectrometric Analysis of Peptides Separated by Capillary Electrophoresis," *Anal. Chem.*, 66:3696–3701 (1994).

Figueros et al., "High–Performance Immobilized–Metal Affinity Chromatography of Proteins on Iminodiacetic Acid Silica–Based Bonded Phases," *J. Chromatogr.* 371:335–352 (1986).

Harrison et al., "Rapid Separation of Fluorescein Derivatives Using a Micromachined Capillary Electrophoresis System," *Analytica Chimica Acta*, 283:361–366 (1993).

Harrison et al., "Capillary Electrophoresis and Sample Injection Systems Integrated on a Planar Glass Chip," *Anal. Chem.* 64(17):1926–1932 (1992).

Harrison et al., "Towards Miniaturized Electrophoresis and Chemical Analysis Systems on Silicon: An Alternative to Chemical Sensors," *Sensors and Actuators B*, 10:107–116 (1993).

Jacobsen et al., "Microchip Electrophoresis With Sample Stacking," *Electrophoresis*, 16:481–486 (1995).

Jacobson et al., "Fused Quartz Substrates for Microchip Electrophoresis," *Anal. Chem.*, 67:2059–2063 (1996).

Jacobson et al., "Microchip Capillary Electrophoresis with an Integrated Postcolumn Reactor," *Anal. Chem.*, 66:3472–3476 (1994).

Jacobson et al., "Effects of Injection Schemes and Column Geometry on the Performance of Microchip Electrophoresis Devices," *Anal. Chem.*, 66:1107–1113 (1994).

Jacobson et al., "Integrated Microdevice for DNA Restriction Fragment Analysis," *Anal. Chem.*, 68(5):720–723 (1996).

Jacobson et al., "Precolumn Reactions with Electrophoretic Analysis Integrated on a Microchip," *Anal. Chem.*, 66:4127–4132 (1994).

Jameson et al., "Micro Vials on a Silicon Wafer for Sample Introduction in Capillary Electrophoresis," *J. Chromatoer.*626:310–314 (1992).

Ko et al., "Semiconductor Integrated Circuit Technology and Micromachining," pp. 109–168—undated.

Körner et al., "Nano Electrospray Combined with a Quadrupole Ion Trap for the Analysis of Peptides and Protein Digests," *J. Am. Soc. Mass. Spectrom.*, 7:150–156 (1996).

Koutny et al., "Microchip Electrophoretic Immunoassay for Serum Cortisol," *Anal. Chem.*, 68:18–22 (1996).

Kriger et al., "Durable Gold–Coated Fused Silica Capillaries for Use in Electrospray Mass Spectrometry," *Anal. Chem.*, 67:385–389 (1995).

Manz et al., "Micromachining of Monocrystalline Silicon and Glass for Chemical Analysis Systems," *Trends in Anal. Chem.*, 10(5):144–149 (1991).

Manz et al., "Planar Chips Technology for Miniaturization and Integration of Separation Techniques Into Monitoring Systems," *J. Chromatogr.*, 593:253–258 (1992).

Manz et al., "Planar Chips Technology for Miniaturization of Separation Systems: A Developing Perspective in Chemical Monitoring," *Advances in Chromagotraphy*, pp. 1–66 (1993).

Manz et al., "Design of an Open–Tubular Column Liquid Chromatograph Using Silicon Chip Technology," *Sensors and Actuators*, B1:249–255 (1990).

Manz et al., "Miniaturization of Separation Techniques Using Planar Chip Technology," *J. High Resol. Chromatoer.*, 16:433–436 (1993).

Manz et al., "Planar Chip Technology for Capillary Electrophoresis," *Presenius J. Anal. Chem.*, 348:567–571 (1994).

Moore et al., "Microchip Separations of Neural Species Via Micellar Electrokinetic Capillary Chromatography," *Anal. Chem.*, 67:4184–4189 (1995).

Nichols et al., "CE–MS for Industrial Applications Using a Liquid Junction With Ion–Spray and CF–FAB Mass Spectrometry," *LC–GC* 10(9):676–686 (1992).

Ocvirk et al., "High Performance Liquid Chromatography Partially Integrated Onto a Silicon Chip," *Anal. Meth. Instrumen.*, 2(2):74–82 (1995).

Olivares et al., "On–Line Mass Spectrometric Detection for Capillary Zone Electrophoresis," *Anal. Chem.*, 59:1230–1232 (1987).

Overon et al., "Development of a Temperture Programmed Microchip, High Resolution Gas Chromatograph/Mass Spectrometer for Volatile Organic Compound Analysis," pp. 395–398.

Petersen, "Biomedical Applications of MEMS," *IEEE*, pp. 239–242 (1996).

Raymond et al., "Continuous Sample Pretreatment Using a Free–Flow Electrophoresis Devices Integrated Onto a Silicon Chip," *Anal. Chem.*, 66:2858–2865 (1994).

Roeraade, "Nano–Sized Systems for Bioanalysis," Eighth International Symposium on High Performance Capillary Electrophoresis, pp. 3, 19, 68 (1996) (abstract).

Seiler et al., "Electroosmotic Pumping and Valveless Control of Fluid Flow Within a Manifold of Capillaries on a Glass Chip," *Anal. Chem.*, 66(20):3485–3491 (1994).

Seiler et al., "Planar Glass Chips for Capillary Electrophoresis: Repetitive Sample Injection, Quantitation, and Separation Efficiency," *Anal. Chem.*, 65:1481–1488 (1993).

Shoffner et al., "Chip PCR. I. Surface Passivation of Microfabricated Silicon–Glass Chips for PCR," *Nucleic Acids Res.*, 24(2):375–379 (1996).

Sjolander et al., "Integrated Fluid Handling System for Biomolecular Interaction Analysis," *Anal. Chem.*, 63(20):2338–2345 (1991).

Smith et al., "Improved Electrospray Ionization Interface for Capillary Zone Electrophoresis–Mass Spectrometry," *Anal. Chem.*, 60:1948–1952 (1988).

Valaskovic et al., "Automole–Sensitivity Electrospray Source for Large–Molecule Mass Spectrometry," *Anal. Chem.*, 67:3802–3805 (1995).

Wahl et al., "Sheathless Capillary Electrophoresis–Electrospray Ionization Mass–Spectrometry Using 10 $\mu$m I.D. Capillaries: Analyses of Trytpic Digests of Cytochrome c," *J. Chromatogr. A*, 659:217–222 (1994).

Whitehouse et al., "Electrospray Interface for Liquid Chromatographs and Mass Spectrometers," *Anal. Chem.*, 57:675–679 (1985).

Woolley et al., "Ultra–High–Speed DNA Sequencing Using Capillary Electrophoresis Chips," *Anal. Chem.*, 67:3676–3680 (1995).

Woolley et al., "Ultra–High–Speed DNA Fragment Separations Using Microfabricated Capillary Array Electrophoresis Chips," *Proc. Natl. Acad. Sci. USA*, 91:11348–11352 (1994).

Yoshida et al., "Direct Measurement of Mass Fragmentograms for Eluents From a Micro–Liquid Chromatograph Using an Improved Nebulizing Interface," *J. HRC&CC*, 3:16–20 (1980).

Smith et al., "New Developments in Microscale Separations and Mass Spectrometry for Biomonisoring: Capillary Electrophoresis and Electrospray Ionization Mass Spectrometry," *J. Toxicol. and Environ. Health*, 40:147–158 (1993).

Andrea et al., "Micro–Electrospray: Zeptomole/Attomole per Microtiter Sensitivity for Peptides," *J. Am. Soc. Mass Spectrom.*, 5:867–869 (1994).

Angell et al., "Silicon Micromechanical Devices," *Scientific American*, 248(4):44–55 (1983).

Beavis et al., "Automated Dry Fraction Collection for Microbore High–Performance Liquid Chromatography–Mass Spectrometry," *J. Chromatography*, 359:489–497 (1986).

\* cited by examiner

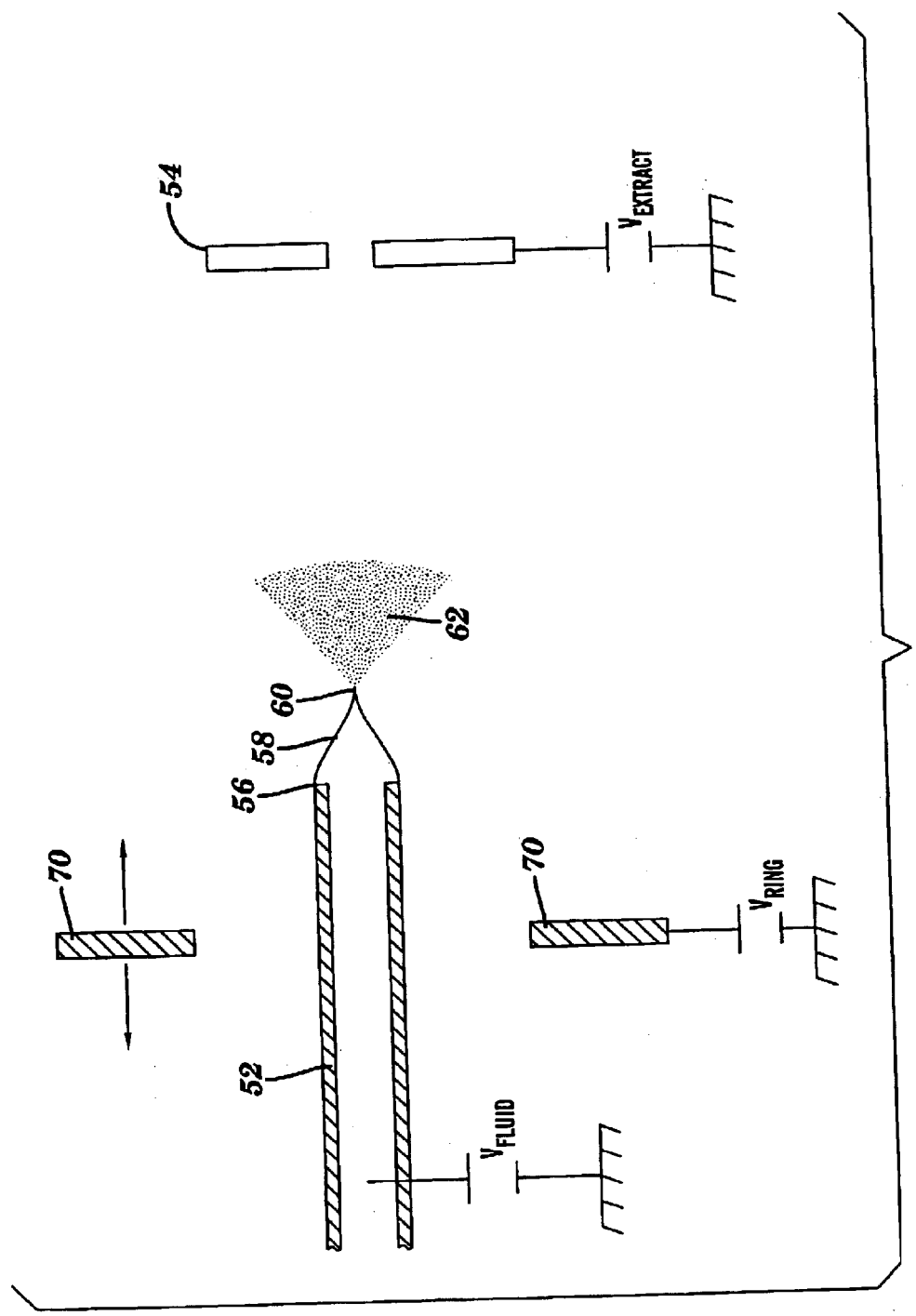

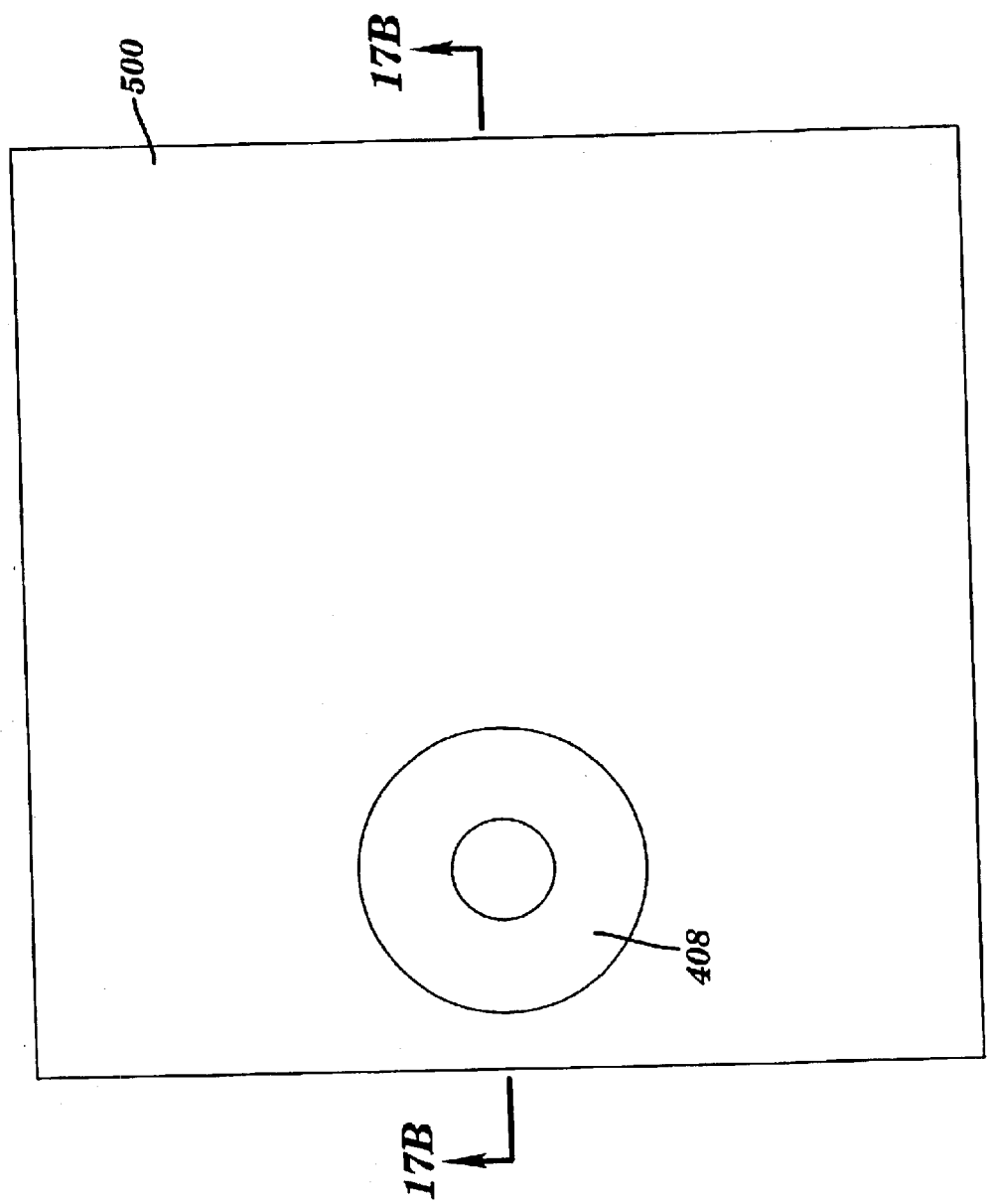

INTEGRATED MONOLITHIC MICROFABRICATED DISPENSING NOZZLE AND LIQUID CHROMATOGRAPHY-ELECTROSPRAY SYSTEM AND METHOD

This application is a division of U.S. patent application Ser. No. 09/468,535, filed Dec. 20, 1999 now U.S. Pat. No. 6,633,031.

This application claims the benefit of U.S. Provisional Patent Application Serial No. 60/122,972, filed Mar. 2, 1999.

FIELD OF THE INVENTION

The present invention relates generally to an integrated miniaturized fluidic system fabricated using microelectromechanical systems (MEMS) technology, particularly to an integrated monolithic microfabricated dispensing nozzle capable of dispensing fluids in the form of droplets or as an electrospray of the fluid.

BACKGROUND OF THE INVENTION

New trends in drug discovery and development are creating new demands on analytical techniques. For example, combinatorial chemistry is often employed to discover new lead compounds, or to create variations of a lead compound. Combinatorial chemistry techniques can generate thousands of compounds (combinatorial libraries) in a relatively short time (on the order of days to weeks). Testing such a large number of compounds for biological activity in a timely and efficient manner requires high-throughput screening methods which allow rapid evaluation of the characteristics of each candidate compound.

The compounds in combinatorial libraries are often tested simultaneously against a molecular target. For example, an enzyme assay employing a colorimetric measurement may be run in a 96-well plate. An aliquot of enzyme in each well is combined with tens of compounds. An effective enzyme inhibitor will prevent development of color due to the normal enzyme reaction, allowing for rapid spectroscopic (or visual) evaluation of assay results. If ten compounds are present in each well, 960 compounds can be screened in the entire plate, and one hundred thousand compounds can be screened in 105 plates, allowing for rapid and automated biological screening of the compounds.

The quality of the combinatorial library and the compounds contained therein is used to assess the validity of the biological screening data. Confirmation that the correct molecular weight is identified for each compound or a statistically relevant number of compounds along with a measure of compound purity are two important measures of the quality of a combinatorial library. Compounds can be analytically characterized by removing a portion of solution from each well and injecting the contents into a separation device such as liquid chromatography or capillary electrophoresis instrument coupled to a mass spectrometer. Assuming that such a method would take approximately 5 minutes per analysis, it would require over a month to analyze the contents of 105 96-well plates, assuming the method was fully automated and operating 24 hours a day. Even larger well-plates containing 384 and 1536 wells are being integrated into the screening of new chemical entities imposing even greater time constraints on the analytical characterization of these libraries.

Recent technological developments in combinatorial chemistry, molecular biology, and new microchip chemical devices have created the need for new types of dispensing devices. Applications in combinatorial chemistry require robust sample delivery systems that are chemically inert and distribute less than microliter amounts of liquid in high-density formats. The systems need to be highly reproducible and have overall quick dispensing times. Current dispensing technology utilizes serial injection schemes. The use of serial dispensers will be inherently limited due to their slows overall distribution times as the move to high-density formats progresses. For example, for combinatorial chemistry applications, to synthesize a library of 1 million discrete compounds, each composed of 4 monomers, a total of 4×106 dispensing steps would be required. If each dispensing step required 3 seconds (considering dispense time, rinsing, and, location positioning), the total time to dispense all of the reagents would be 12×106 seconds, or 3333 hours, or 139 days. Thus, for high-density formats, dispensing must be conducted in parallel. In order for parallel dispensing to work in high-density formats, the dispensing device must be small enough to allow all dispensing units to be simultaneously positioned within a corresponding receiving well. This requires the dispenser to be relatively small. As high density formats reach greater than 10,000 wells, dispensing devices will need to be spaced within 100 $\mu$m or less. In addition, in order for the dispenser to be practical, the device must dispense small quantities of liquid ($10^{-9}$ to $10^{-12}$ L), and only require small volumes to operate.

Piezoelectric dispensing units have also been used for dispensing small amounts of liquid for microdevices. However, piezoelectric dispensers suffer from several problems. Currently, the closest spacing of individual dispensers is 330 $\mu$m in an array of four. Due to the current piezoelectric design and fabrication, the number of dispensers that can be positioned adjacent to one another is limited because of downstream device features. Additionally, sample requirements may be quite high even though the dispensing volume is small.

Enormous amounts of genetic sequence data are being generated through new DNA sequencing methods. This wealth of new information is generating new insights into the mechanism of disease processes. In particular, the burgeoning field of genomics has allowed rapid identification of new targets for drug discovery. Determination of genetic variations between individuals has opened up the possibility of targeting drugs to individuals based on the individual's particular genetic profile. Testing for cytotoxicity, specificity, and other pharmaceutical characteristics could be carried out in high-throughput assays instead of expensive animal testing and clinical trials. Detailed characterization of a potential drug or lead compound early in the drug development process thus has the potential for significant savings both in time and expense.

Development of viable screening methods for these new targets will often depend on the availability of rapid separation and analysis techniques for analyzing the results of assays. For example, an assay for potential toxic metabolites of a candidate drug would need to identify both the candidate drug and the metabolites of that candidate. An assay for specificity would need to identify compounds that bind differentially to two molecular targets such as a viral protease and a mammalian protease.

It would, therefore, be advantageous to provide a method for efficient proteomic screening in order to obtain the pharmacokinetic profile of a drug early in the evaluation process. An understanding of how a new compound is absorbed in the body and how it is metabolized can enable prediction of the likelihood for an increased therapeutic effect or lack thereof.

Given the enormous number of new compounds that are being generated daily, an improved system for identifying molecules of potential therapeutic value for drug discovery is also critically needed. Accordingly, there is a critical need for high-throughput screening and identification of compound-target reactions in order to identify potential drug candidates.

Liquid chromatography (LC) is a well-established analytical method for separating components of a fluid for subsequent analysis and/or identification. Traditionally, liquid chromatography utilizes a separation column, such as a cylindrical tube with dimensions 4.6 mm inner diameter by 25 cm length, filled with tightly packed particles of 5 µm diameter. More recently, particles of 3 µm diameter are being used in shorter length columns. The small particle size provides a large surface area that can be modified with various chemistries creating a stationary phase. A liquid eluent is pumped through the LC column at an optimized flow rate based on the column dimensions and particle size. This liquid eluent is referred to as the mobile phase. A volume of sample is injected into the mobile phase prior to the LC column. The analytes in the sample interact with the stationary phase based on the partition coefficients for each of the analytes. The partition coefficient is defined as the ratio of the time an analyte spends interacting with the stationary phase to the time spent interacting with the mobile phase. The longer an analyte interacts with the stationary phase, the higher the partition coefficient and the longer the analyte is retained on the LC column. The diffusion rate for an analyte through a mobile phase (mobile-phase mass transfer) also affects the partition coefficient. The mobile-phase mass transfer can be rate limiting in the performance of the separation column when it is greater than 2 µm (Knox, J. H. J. *J. Chromatogr. Sci.* 18:453–461 (1980)). Increases in chromatographic separation are achieved when using a smaller particle size as the stationary phase support.

The purpose of the LC column is to separate analytes such that a unique response for each analyte from a chosen detector can be acquired for a quantitative or qualitative measurement. The ability of a LC column to generate a separation is determined by the dimensions of the column and the particle size supporting the stationary phase. A measure of the ability of LC columns to separate a given analyte is referred to as the theoretical plate number N. The retention time of an analyte can be adjusted by varying the mobile phase composition and the partition coefficient for an analyte. Experimentation and a fundamental understanding of the partition coefficient for a given analyte determine which stationary phase is chosen.

To increase the throughput of LC analyses requires a reduction in the dimensions of the LC column and the stationary phase particle dimensions. Reducing the length of the LC column from 25 cm to 5 cm will result in a factor of 5 decrease in the retention time for an analyte. At the same time, the theoretical plates are reduced 5-fold. To maintain the theoretical plates of a 25 cm length column packed with 5 µm particles, a 5 cm column would need to be packed with 1 µm particles. However, the use of such small particles results in many technical challenges.

One of these technical challenges is the backpressure resulting from pushing the mobile phase through each of these columns. The backpressure is a measure of the pressure generated in a separation column due to pumping a mobile phase at a given flow rate through the LC column. For example, the typical backpressure of a 4.6 mm inner diameter by 25 cm length column packed with 5 µm particles generates a backpressure of 100 bar at a flow rate of 1.0 mL/min. A 5 cm column packed with 1 µm particles generates a back pressure 5 times greater than a 25 cm column packed with 5 µm particles. Most commercially available LC pumps are limited to operating pressures less than 400 bar and thus using an LC column with these small particles is not feasible.

Detection of analytes separated on an LC column has traditionally been accomplished by use of spectroscopic detectors. Spectroscopic detectors rely on a change in refractive index, ultraviolet and/or visible light absorption, or fluorescence after excitation with a suitable wavelength to detect the separated components. Additionally, the effluent from an LC column may be nebulized to generate an aerosol which is sprayed into a chamber to measure the light scattering properties of the analytes eluting from the column. Alternatively, the separated components may be passed from the liquid chromatography column into other types of analytical instruments for analysis. The volume from the LC column to the detector is minimized in order to maintain the separation efficiency and analysis sensitivity. All system volume not directly resulting from the separation column is referred to as the dead volume or extra-column volume.

The miniaturization of liquid separation techniques to the nano-scale involves small column internal diameters (<100 µm i.d.) and low mobile phase flow rates (<300 nL/min). Currently, techniques such as capillary zone electrophoresis (CZE), nano-LC, open tubular liquid chromatography (OTLC), and capillary electrochromatography (CEC) offer numerous advantages over conventional scale high performance liquid chromatography (HPLC). These advantages include higher separation efficiencies, high-speed separations, analysis of low volume samples, and the coupling of 2-dimensional techniques. One challenge to using miniaturized separation techniques is detection of the small peak volumes and a limited number of detectors that can accommodate these small volumes. However, coupling of low flow rate liquid separation techniques to electrospray mass spectrometry results in a combination of techniques that are well suited as demonstrated in J. N. Alexander IV, et al., *Rapid Commun. Mass Spectrom,* 12:1187–91 (1998). The process of electrospray at flow rates on the order of nanoliters per minute has been referred to as "nanoelectrospray".

Capillary electrophoresis is a technique that utilizes the electrophoretic nature of molecules and/or the electroosmotic flow of fluids in small capillary tubes to separate components of a fluid. Typically, a fused silica capillary of 100 µm inner diameter or less is filled with a buffer solution containing an electrolyte. Each end of the capillary is placed in a separate fluidic reservoir containing a buffer electrolyte. A potential voltage is placed in one of the buffer reservoirs and a second potential voltage is placed in the other buffer reservoir. Positively and negatively charged species will migrate in opposite directions through the capillary under the influence of the electric field established by the two potential voltages applied to the buffer reservoirs. Electroosmotic flow is defined as the fluid flow along the walls of a capillary due to the migration of charged species from the buffer solution under the influence of the applied electric field. Some molecules exist as charged species when in solution and will migrate through the capillary based on the charge-to-mass ratio of the molecular species. This migration is defined as electrophoretic mobility. The electroosmotic flow and the electrophoretic mobility of each component of a fluid determine the overall migration for each fluidic component. The fluid flow profile resulting from electroosmotic flow is flat due to the reduction in frictional drag along the walls of the separation channel. This results in improved separation efficiency compared to liquid chromatography where the flow profile is parabolic resulting from pressure driven flow.

Capillary electrochromatography is a hybrid technique that utilizes the electrically driven flow characteristics of electrophoretic separation methods within capillary columns packed with a solid stationary phase typical of liquid chromatography. It couples the separation power of reversed-phase liquid chromatography with the high efficiencies of capillary electrophoresis. Higher efficiencies are obtainable for capillary electrochromatography separations over liquid chromatography, because the flow profile resulting from electroosmotic flow is flat due to the reduction in frictional drag along the walls of the separation channel when compared to the parabolic flow profile resulting from pressure driven flows. Furthermore, smaller particle sizes can be used in capillary electrochromatography than in liquid chromatography, because no backpressure is generated by electroosmotic flow. In contrast to electrophoresis, capillary electrochromatography is capable of separating neutral molecules due to analyte partitioning between the stationary and mobile phases of the column particles using a liquid chromatography separation mechanism.

Microchip-based separation devices have been developed for rapid analysis of large numbers of samples. Compared to other conventional separation devices, these microchip-based separation devices have higher sample throughput, reduced sample and reagent consumption, and reduced chemical waste. The liquid flow rates for microchip-based separation devices range from approximately 1–300 nanoliters (nL) per minute for most applications. Examples of microchip-based separation devices include those for capillary electrophoresis ("CE"), capillary electrochromatography ("CEC") and high-performance liquid chromatography ("HPLC") include Harrison et al., *Science* 261:859–97 (1993); Jacobson et al., *Anal. Chem.* 66:1114–18 (1994). Jacobson et al., *Anal. Chem.* 66:2369–73 (1994), Kutter et al., *Anal. Chem.* 69:5165–71 (1997) and He et al., *Anal. Chem.* 70:3790–97 (1998). Such separation devices are capable of fast analyses and provide improved precision and reliability compared to other conventional analytical instruments.

The work of He et al., *Anal. Chem.* 70:3790–97 (1998) demonstrates some of the types of structures that can be fabricated in a glass substrate. This work shows that co-located monolithic support structures (or posts) can be etched reproducibly in a glass substrate using reactive ion etching (RIE) techniques. Currently, anisotropic RIE techniques for glass substrates are limited to etching features that are 20 $\mu$m or less in depth. This work shows rectangular 5 $\mu$m by 5 $\mu$m width by 10 $\mu$m in depth posts and stated that deeper structures were difficult to achieve. The posts are also separated by 1.5 $\mu$m. The posts supports the stationary phase just as with the particles in LC and CEC columns. An advantage to the posts over conventional LC and CEC is that the stationary phase support structures are monolithic with the substrate and therefore, immobile.

He et. al., also describes the importance of maintaining a constant cross-sectional area across the entire length of the separation channel. Large variations in the cross-sectional area can create pressure drops in pressure driven flow systems. In electrokinetically driven flow systems, large variations in the cross-sectional area along the length of a separation channel can create flow restrictions that result in bubble formation in the separation channel. Since the fluid flowing through the separation channel functions as the source and carrier of the mobile solvated ions, formation of a bubble in a separation channel will result in the disruption of the electroosmotic flow.

Electrospray ionization provides for the atmospheric pressure ionization of a liquid sample. The electrospray process creates highly-charged droplets that, under evaporation, create ions representative of the species contained in the solution. An ion-sampling orifice of a mass spectrometer may be used to sample these gas phase ions for mass analysis. A schematic of an electrospray system 50 is shown in FIG. 1A. An electrospray is produced when a sufficient electrical potential difference $V_{spray}$ is applied between a conductive or partly conductive fluid exiting a capillary 52 and an extracting electrode 54 to generate a concentration of electric field lines emanating from the tip or end of a capillary 56. When a positive voltage $V_{spray}$ is applied to the tip of the capillary relative to an extracting electrode, such as one provided at the ion-sampling orifice of a mass spectrometer, the electric field causes positively-charged ions in the fluid to migrate to the surface of the fluid at the tip of the capillary. When a negative voltage $V_{spray}$ is applied to the tip of the capillary relative to an extracting electrode, such as one provided at the ion-sampling orifice to the mass spectrometer, the electric field causes negatively-charged ions in the fluid to migrate to the surface of the fluid at the tip of the capillary.

When the repulsion force of the solvated ions on the surface of the fluid exceeds the surface tension of the fluid being electrosprayed, a volume of the fluid is pulled into the shape of a cone, known as a Taylor cone 58, which extends from the tip of the capillary 56. A liquid jet 60 extends from the tip of the Taylor cone and becomes unstable and generates charged-droplets 62. These small charged droplets are drawn toward the extracting electrode 54. The small droplets are highly-charged and solvent evaporation from the droplets results in the excess charge in the droplet residing on the analyte molecules in the electrosprayed fluid. The charged molecules or ions are drawn through the ion-sampling orifice of the mass spectrometer for mass analysis. This phenomenon has been described, for example, by Dole et al., *Chem. Phys.* 49:2240 (1968) and Yamashita et al., *J. Phys. Chem.* 88:4451 (1984). The potential voltage required to initiate an electrospray is dependent on the surface tension of the solution as described by, for example, Smith, *IEEE Trans. Ind. Appl.* 1986, IA-22:527–35 (1986). Typically, the electric field is on the order of approximately $10^6$ V/m. The physical size of the capillary and the fluid surface tension determines the density of electric field lines necessary to initiate electrospray.

When the repulsion force of the solvated ions is not sufficient to overcome the surface tension of the fluid exiting the tip of the capillary, large poorly charged droplets are formed as shown in FIG. 1B. Fluid droplets 64 are produced when the electrical potential difference $V_{droplet}$ applied between a conductive or partly conductive fluid exiting a capillary 52 and an electrode is not sufficient to overcome the fluid surface tension to form a Taylor cone.

*Electrospray Ionization Mass Spectrometry: Fundamentals. Instrumentation, and Applications*, edited by R. B. Cole, ISBN 0-471-14564-5, John Wiley & Sons, Inc., New York summarizes much of the fundamental studies of electrospray. Several mathematical models have been generated to explain the principals governing electrospray. Equation 1 defines the electric field $E_c$ at the tip of a capillary of radius $r_c$ with an applied voltage $V_c$ at a distance d from a counter electrode held at ground potential:

$$E_c = \frac{2V_c}{r_c \ln(4d/r_c)} \quad (1)$$

The electric field $E_{on}$ required for the formation of a Taylor cone and liquid jet of a fluid flowing to the tip of this capillary is approximated as:

$$E_{on} \approx \left(\frac{2\gamma\cos\theta}{\varepsilon_0 r_c}\right)^{1/2} \quad (2)$$

where $\gamma$ is the surface tension of the fluid, $\theta$ is the half-angle of the Taylor cone and $\varepsilon_0$ is the permittivity of vacuum. Equation 3 is derived by combining equations 1 and 2 and approximates the onset voltage $V_{on}$ required to initiate an electrospray of a fluid from a capillary:

$$V_{on} \approx \left(\frac{r_c\gamma\cos\theta}{2\varepsilon_0}\right)^{1/2} \ln(4d/r_c) \quad (3)$$

The graph of FIG. 1C shows curves for onset voltages of 500, 750 and 1000 V as related to surface tension of a fluid undergoing electrospray from the tip of a capillary with a given outer diameter. The distance of the capillary tip from the counter-electrode was fixed at 2 mm. Combinations of fluid surface tension and capillary diameters that fall below the curves will generate a stable electrospray using a given onset voltage. As can be seen by examination of equation 3, the required onset voltage is more dependent on the capillary radius than the distance from the counter-electrode.

It would be desirable to define an electrospray device that could form a stable electrospray of all fluids commonly used in CE, CEC, and LC. The surface tension of solvents commonly used as the mobile phase for these separations range from 100% aqueous ($\gamma=0.073$ N/m) to 100% methanol ($\gamma=0.0226$ N/m). FIG. 1C indicates that as the surface tension of the electrospray fluid increases, a higher onset voltage is required to initiate an electrospray for a fixed capillary diameter. As an example, a capillary with a tip diameter of 14 $\mu$m is required to electrospray 100% aqueous solutions with an onset voltage of 1000 V. The work of M. S. Wilm et al., *Int. J. Mass Spectrom. Ion Processes* 136:167–80 (1994), first demonstrates nanoelectrospray from a fused-silica capillary pulled to an outer diameter of 5 $\mu$m at a flow rate of 25 nL/min. Specifically, a nanoelectrospray at 25 nL/min was achieved from a 2 $\mu$m inner diameter and 5 $\mu$m outer diameter pulled fused-silica capillary with 600–700 V at a distance of 1–2 mm from the ion-sampling orifice of an electrospray equipped mass spectrometer.

Electrospray in front of an ion-sampling orifice of an API mass spectrometer produces a quantitative response from the mass spectrometer detector due to the analyte molecules present in the liquid flowing from the capillary. One advantage of electrospray is that the response for an analyte measured by the mass spectrometer detector is dependent on the concentration of the analyte in the fluid and independent of the fluid flow rate. The response of an analyte in solution at a given concentration would be comparable using electrospray combined with mass spectrometry at a flow rate of 100 $\mu$L/min compared to a flow rate of 100 nL/min. D.C. Gale et al., *Rapid Commun. Mass Spectrom.* 7:1017 (1993) demonstrate that higher electrospray sensitivity is achieved at lower flow rates due to increased analyte ionization efficiency.

Attempts have been made to manufacture an electrospray device for microchip-based separations. Ramsey et al., *Anal. Chem.* 69:1174–78 (1997) describes a microchip-based separations device coupled with an electrospray mass spectrometer. Previous work from this research group including Jacobson et al., *Anal. Chem.* 66:1114–18 (1994) and Jacobson et al., *Anal. Chem.* 66:2369–73 (1994) demonstrate impressive separations using on-chip fluorescence detection. This more recent work demonstrates nanoelectrospray at 90 nL/min from the edge of a planar glass microchip. The microchip-based separation channel has dimensions of 10 $\mu$m deep, 60 $\mu$m wide, and 33 mm in length. Electroosmotic flow is used to generate fluid flow at 90 nL/min. Application of 4,800 V to the fluid exiting the separation channel on the edge of the microchip at a distance of 3–5 mm from the ion-sampling orifice of an API mass spectrometer generates an electrospray. Approximately 12 nL of the sample fluid collects at the edge of the microchip before the formation of a Taylor cone and stable nanoelectrospray from the edge of the microchip. The volume of this microchip-based separation channel is 19.8 nL. Nanoelectrospray from the edge of this microchip device after capillary electrophoresis or capillary electrochromatography separation is rendered impractical since this system has a dead-volume approaching 60% of the column (channel) volume. Furthermore, because this device provides a flat surface, and, thus, a relatively small amount of physical asperity for the formation of the electrospray, the device requires an impractically high voltage to overcome the fluid surface tension to initiate an electrospray.

Xue, Q. et al., *Anal. Chem.* 69:426–30 (1997) also describes a stable nanoelectrospray from the edge of a planar glass microchip with a closed channel 25 $\mu$m deep, 60 $\mu$m wide, and 35–50 mm in length. An electrospray is formed by applying 4,200 V to the fluid exiting the separation channel on the edge of the microchip at a distance of 3–8 mm from the ion-sampling orifice of an API mass spectrometer. A syringe pump is utilized to deliver the sample fluid to the glass microchip at a flow rate of 100 to 200 nL/min. The edge of the glass microchip is treated with a hydrophobic coating to alleviate some of the difficulties associated with nanoelectrospray from a flat surface that slightly improves the stability of the nanoelectrospray. Nevertheless, the volume of the Taylor cone on the edge of the microchip is too large relative to the volume of the separation channel, making this method of electrospray directly from the edge of a microchip impracticable when combined with a chromatographic separation device.

T. D. Lee et. al., 1997 *International Conference on Solid-State Sensors and Actuators* Chicago, pp. 927–30 (Jun. 16–19, 1997) describes a multi-step process to generate a nozzle on the edge of a silicon microchip 1–3 $\mu$m in diameter or width and 40 $\mu$m in length and applying 4,000 V to the entire microchip at a distance of 0.25–0.4 mm from the ion-sampling orifice of an API mass spectrometer. Because a relatively high voltage is required to form an electrospray with the nozzle positioned in very close proximity to the mass spectrometer ion-sampling orifice, this device produces an inefficient electrospray that does not allow for sufficient droplet evaporation before the ions enter the orifice. The extension of the nozzle from the edge of the microchip also exposes the nozzle to accidental breakage. More recently, T. D. Lee et.al., in 1999 *Twelfth IEEE International Micro Electro Mechanical Systems Conference* (Jan. 17–21, 1999), presented this same concept where the electrospray component was fabricated to extend 2.5 mm beyond the edge of the microchip to overcome this phenomenon of poor electric field control within the proximity of a surface.

In all of the above-described devices, generating an electrospray from the edge of a microchip is a poorly controlled process. These devices do not define a nozzle and an electric field around the nozzle that is required to produce a stable and highly reproducible electrospray. In another embodiment, small segments of fused-silica capillaries are separately and individually attached to the chip's edge. This process is inherently cost-inefficient and unreliable, imposes space constraints in chip design, and is therefore unsuitable for manufacturing.

Thus, it is also desirable to provide an electrospray device with controllable spraying and a method for producing such a device that is easily reproducible and manufacturable in high volumes.

U.S. Pat. No. 5,501,893 to Laermer et. al., reports a method of anisotropic plasma etching of silicon (Bosch process) that provides a method of producing deep vertical structures that is easily reproducible and controllable. This method of anisotropic plasma etching of silicon incorporates a two step process. Step one is an anisotropic etch step using a reactive ion etching (RIE) gas plasma of sulfur hexafluoride ($SF_6$). Step two is a passivation step that deposits a polymer on the vertical surfaces of the silicon substrate. This polymerizing step provides an etch stop on the vertical surface that was exposed in step one. This two step cycle of etch and passivation is repeated until the depth of the desired structure is achieved. This method of anisotropic plasma etching provides etch rates over 3 m$\mu$/min of silicon depending on the size of the feature being etched. The process also provides selectivity to etching silicon versus silicon dioxide or resist of greater than 100:1 which is important when deep silicon structures are desired. Laermer et. al., in 1999 *Twelfth IEEE International Micro Electro Mechanical Systems Conference* (Jan. 17–21, 1999), reported improvements to the Bosch process. These improvements include silicon etch rates approaching 10 $\mu$m/min, selectivity exceeding 300:1 to silicon dioxide masks, and more uniform etch rates for features that vary in size.

The electrical properties of silicon and silicon-based materials are well characterized. The use of silicon dioxide and silicon nitride layers grown or deposited on the surfaces of a silicon substrate are well known to provide electrical insulating properties. Silicon dioxide layers may be grown thermally in an oven to a desired thickness. Silicon nitride can be deposited using low pressure chemical vapor deposition (LPCVD). Metals may be further vapor deposited on these surfaces to provide for application of a potential voltage on the surface of the device. Both silicon dioxide and silicon nitride function as electrical insulators allowing the application of a potential voltage to the substrate that is different than that applied to the surface of the device. An important feature of a silicon nitride layer is that it provides a moisture barrier between the silicon substrate, silicon dioxide and any fluid sample that comes in contact with the device. Silicon nitride prevents water and ions from diffusing through the silicon dioxide layer to the silicon substrate which may cause an electrical breakdown between the fluid and the silicon substrate. Additional layers of silicon dioxide, metals and other materials may further be deposited on the silicon nitride layer to provide chemical functionality to silicon-based devices.

The present invention is directed to overcoming the deficiencies in prior electrospray systems.

SUMMARY OF THE INVENTION

The present invention relates to an electrospray device which comprises a substrate having an injection surface and an ejection surface opposing the injection surface with the substrate being an integral monolith. An entrance orifice is positioned on the injection surface, while an exit orifice is on the ejection surface. A channel extends between the entrance orifice and the exit orifice. A recess surrounds the exit orifice and is positioned between the injection surface and the ejection surface. The electrospray device has voltage application system consisting essentially of a first electrode attached to the substrate to impart a first potential to the substrate and a second electrode to impart a second potential, where the first and the second electrodes are positioned to define an electric field surrounding the exit orifice. This device can be used in conjunction with systems for processing droplet/sprays, methods of generating an electrospray, a method of mass spectrometeric analysis; and a method of liquid chromatographic analysis.

Another aspect of the present invention is directed to an electrospray device which includes a capillary tube having a passage for conducting fluids through the capillary tube and connecting an entrance orifice and an exit orifice, a first electrode circumscribing the capillary tube proximate the exit orifice, and a second electrode to impart a second potential. The first and the second electrodes are positioned to define an electric field surrounding the exit orifice.

Another aspect of the present invention relates to a method of producing an electrospray device which includes providing a substrate having opposed first and second surfaces, each coated with a photoresist. The photoresist on the first surface is exposed to an optical image to form a pattern is the form of a spot on the first surface. The photoresist on the first surface where the pattern is removed to form a hole in the photoresist. Material is removed from the substrate coincident with the hole in the photoresist on the first surface to form a channel extending through the photoresist on the first surface and through the substrate up to the photoresist on the second surface. The photoresist on the second surface is exposed to an image to form an annular pattern circumscribing an extension of the channel through the photoresist on the second surface. The photoresist on the second surface having the annular pattern is then removed, and, next, the material from the substrate coincident with the removed annular pattern in the phototresist on the second surface is removed to form an annular recess extending partially into the substrate. All coatings from the first and second surfaces of the substrate are removed to form the electrospray device.

Another aspect of the present invention relates to a method of producing an electrospray device. This method includes providing a substrate having opposed first and second surfaces, each coated with a photoresist. The photoresist is exposed on the first surface to an image to form a pattern in the form of at least 3 substantially aligned spots on the first surface. The photoresist on the first surface is removed where the pattern is to form 3 holes in the photoresist corresponding to where the spots in the photoresist were. Material from the substrate coincident with the removed pattern in the photoresist on the first surface is then removed to form a central channel aligned with and between two outer channels. The channels extend through the photoresist on the first surface and into the substrate. The central channel has a diameter which is less than that of the outer channels such that the central channel extends farther from the second surface of the substrate than the outer channels which extend up to the photoresist on the the second surface. The photoresist on the second surface is exposed to an image which forms an annular pattern circumscribing a spot, where the spot is coincident with an extension of the central channel through the photoresist on the second surface and a portion of the substrate. The photoresist on the second surface is removed where the annular pattern circumscribing the spot is. Material from the substrate coincident with the removed pattern in the photoresist on the second surface is then removed. This forms an annular recess extending partially into the substrate and circumscribing the central channel which extends through the substrate and the photoresist on the first and second surfaces. All coatings from the first and second surfaces of the substrate are then removed. All surfaces of the substrate are then coated with an insulating material to form the electrospray device.

Another aspect of the present invention relates to a method of forming a liquid separation device. This method involves providing a substrate having opposed first and second surfaces, each coated with a photoresist. The photoresist is exposed on the first surface to an image to form a pattern in the form of a plurality of spots on the first surface. The photoresist on the first surface where the pattern is is removed to form a plurality of holes in the photoresist corresponding to where the spots in the photoresist were. Material from the substrate coincident with where the pattern in the photoresist on the first surface has been removed is then removed. This forms a large reservoir proximate a first end of the substrate and a plurality of smaller holes closer to a second opposite end of the substrate than the reservoir. The reservoir and holes extend through the photoresist on the first surface and partially into the substrate. The smaller holes and the surfaces of the reservoir are filled with a coating, and a further photoresist layer is applied over the coating on the surfaces of the reservoir, the filled holes, and the photoresist on the first surface. The further photoresist is exposed to an image to form a pattern in the form of spots, with one spot coincident with what was the reservoir and the other spot being closer to the second end of the substrate than the filled holes. The further photoresist is removed where the pattern is to form holes corresponding to where the spots in the photoresist were. Material is removed from the substrate coincident with where the pattern in the further photoresist has been removed to form a pair of channels. A first channel extends through what was the reservoir up to the photoresist on the second surface. A second channel extends through the substrate up to the photoresist on the second surface at a location closer to the second end of the substrate than the filled holes. All coatings from the first and second surfaces of the substrate are removed, and all surfaces of the substrate are coated with an insulating material to form the liquid separation device.

Another aspect of the present invention relates to a system for processing droplets/sprays of fluid which includes an electrospray device. The electrospay device contains a substrate having an injection surface and an ejection surface opposing the injection surface. The substrate comprises an entrance orifice on the injection surface, an exit orifice on the ejection surface, a channel extending between the entrance orifice and the exit orifice, and a recess extending into the ejection surface and surrounding the exit orifice. The system further includes a device to provide fluid to the electrospray device which includes a fluid passage, a fluid reservoir in fluid communication with the fluid passage, a fluid inlet to direct fluid entering the device into the fluid reservoir, and a fluid outlet to direct fluid from the fluid passage to the entrance orifice of the electrospray device. The cross-sectional area of the entrance orifice of the electrospray device is equal to or less than the cross-sectional area of the fluid passage.

The present invention achieves a significant advantage in terms of high-throughput distribution and apportionment of massively parallel channels of discrete chemical entities in a well-controlled, reproducible method. An array of dispensing nozzles is disclosed for application in inkjet printing. When combined with a miniaturized liquid chromatography system and method, the present invention achieves a significant advantage in comparison to a conventional system.

The present invention insulates a fluid introduced to the electrospray device from the silicon substrate of the device. This insulation is in the form of silicon dioxide and silicon nitride layers contained on the surfaces of the electrospray device. These insulating layers allow for independent application of a voltage to the fluid introduced to the electrospray device and the voltage applied to the substrate. The independent voltage application to the fluid and substrate allow for control of the electric field around the exit orifice of the nozzle on the ejection surface of the electrospray device independent of the need for any additional electrodes or voltages. This, combined with the dimensions of the nozzle formed from the ejection surface of the electrospray device and the fluid surface tension, determine the electric field and voltages required for the formation of droplets or an electrospray from this invention.

The electrospray device of the present invention can be integrated with microchip-based devices having atmospheric pressure ionization mass spectrometry (API-MS) instruments. By generating an electric field at the tip of a nozzle, which exists in a planar or near planar geometry with the ejection surface of a substrate, fluid droplets and an electrospray exiting the nozzle on the ejection surface are efficiently generated. When a nozzle exists in this co-planar or near planar geometry, the electric field lines emanating from the tip of the nozzle will not be enhanced if the electric field around the nozzle is not defined and controlled.

Control of the electric field at the tip of a nozzle formed from a substrate for the efficient formation of droplets and electrospray from a microchip is an important aspect of the present invention. This was determined using a fused-silica capillary 52 pulled to an outer diameter of approximately 20 μm and inserted through a ring electrode 70 with a 1 mm diameter as shown in FIG. 2. FIG. 2A shows a plan view of the capillary/ring electrode experiment. FIG. 2B shows a cross-sectional view of the capillary/ring electrode experiment. The capillary tip 56 is inserted up to 5 mm through the ring electrode 70 in front of an ion-sampling orifice 54 of a mass spectrometer equipped with an electrospray ion source. A voltage of 700 V is applied to an aqueous fluid $V_{fluid}$ flowing to the capillary tip at a flow rate of 50 nL/min. The ring electrode 70 is mounted on an XYZ stage to allow the ring electrode to be moved slowly forward to the point at which the capillary tip 56 is co-planar with the ring electrode 70 as shown in FIGS. 2C and 2D. The voltage applied to the ring electrode $V_{ring}$ is variable. The voltage applied to the ion-sampling orifice 54 is 80 V. When the fluid voltage and the ring electrode voltage are maintained at 700 V in the co-planar geometry, the electrospray is disrupted and no longer forms an electrospray. Depending on the $V_{fluid}/V_{ring}$ ratio for a fixed distance from a counter electrode 54, fluidic droplets can be controllably dispensed from the capillary tip as shown in FIG. 2C. In this case, minimally-charged, larger droplets are formed with the droplet diameter dependent on the electric field established by the $V_{fluid}/V_{ring}$ ratio, fluid surface tension, fluid conductivity, capillary tip diameter and distance from a counter electrode. Application of a voltage of 0 V to the ring electrode 70 results in the formation of a stable electrospray once again as shown in FIG. 2D. FIG. 2D shows a Taylor cone 58, liquid jet 60 and plume of highly-charged droplets 62.

The response of the analyte measured by the mass spectrometer detector increases beyond that of a capillary with no ring electrode present upon increasing the ring electrode voltage to 350 V. A $V_{fluid}/V_{ring}$ ratio of less than approximately two for a fixed distance from a counter electrode reduces the electric field at the capillary tip to the point where a stable electrospray is no longer sustainable and larger droplet formation is observed. These results indicate that an important feature of an integrated monolithic device designed for droplet formation or electrospray is control of the electric field around the orifice of a nozzle in a co-planar or near planar geometry.

The present invention provides a microchip-based electrospray device for producing reproducible, controllable and robust nanoelectrospray of a liquid sample. The electrospray device is designed to enhance the electric field emanating from a nozzle etched from a surface of a monolithic silicon substrate. This is accomplished by providing insulating layers of silicon dioxide and silicon nitride, for example, for independent application of a potential voltage to a fluid exiting at the tip of the nozzle from a potential voltage applied to the substrate sufficient to cause an electrospray of the fluid. The enhanced electric field combined with the physical asperity of the nozzle allow for the formation of an electrospray of fluids at flow rates as low as a few nanoliters per minute. The large electric field, on the order of $10^6$ V/m or greater and generated by the potential difference between the fluid, and the substrate is thus applied directly to the fluidic cone rather than uniformly distributed in space.

To generate an electrospray, fluid may be delivered to the through-substrate channel of the electrospray device by, for example, a capillary, micropipette or microchip. The fluid is subjected to a potential voltage $V_{fluid}$ via an electrode provided on the injection surface and isolated from the surrounding surface region and the substrate. A potential voltage $V_{substrate}$ may also be applied to the silicon substrate the magnitude of which is preferably adjustable for optimization of the electrospray characteristics. The fluid flows through the channel and exits from the nozzle in the form of a Taylor cone, liquid jet, and very fine, highly charged fluidic droplets. It is the relative electric potential difference between the fluid and substrate voltages that affect the electric field. This invention provides a method of controlling the electric field at the tip of a nozzle to achieve the desired electric field for the application.

The method of fabricating an electrospray device in accordance with the present invention is also advantageous. After injection side processing is completed, the through-substrate channel is etched to a final depth, the photoresist is removed, and the substrate is subjected to an elevated temperature in an oxidizing ambient environment to grow 1–4 μm of silicon dioxide on the walls of the through-substrate channel. This layer of silicon dioxide on the walls of the through-substrate channel provides an etch-stop during further processing of the substrate to define the recessed annular region. The recessed annular region may be patterned and etched from either the injection or ejection side of the substrate when the through-substrate channel is etched through the entire silicon substrate to the silicon dioxide etch stop on the ejection side of the substrate. If the through-substrate channel is not etched completely through the substrate, the recessed annular region is etched from the ejection side of the substrate. The recessed annular region may be patterned and etched to form the silicon dioxide nozzle for injection side processing or for ejection side processing.

This method does not require high alignment accuracy of features from the injection and ejection side processing to define the nozzle wall thickness thus simplifying the method. This method allows nozzles of decreasing size to be reproducibly manufactured and does not require the through-substrate channel to be etched completely through the substrate. The silicon dioxide layer that is grown on the walls of the through-substrate channel determines the wall thickness of the nozzles using this method. The desired nozzle size and use of the electrospray device determines which method is preferred. This fabrication sequence confers superior mechanical stability to the fabricated electrospray device by etching the features of the electrospray device from a monocrystalline silicon substrate without any need for assembly. Further, use of a visible alignment mark as described in the fabrication sequence of this device allows for alignment of injection side and ejection side features to better than 1 μm. This allows for overall nozzle dimensions that are smaller than previously achieved that use prior disclosed alignment schemes using infrared light. Control of the lateral extent and shape of the recessed annular region provides the ability to modify and control the electric field between the electrospray device and an extracting electrode.

This fully integrated monolithic electrospray device may be coupled with a miniaturized monolithic chromatography or other liquid sample handing devices. In particular, the electrospray device used as a means of producing a fluidic cone for spectroscopic detection including laser induced fluorescence, ultraviolet absorption, and evaporative light scattering and mass spectrometry detection. An excitation source provides a light beam. A detector detects the emission or absorbance or light scattering properties of the analytes in the fluidic Taylor cone.

The microchip-based electrospray device of the present invention provides minimal extra-column dispersion as a result of a reduction in the extra-column volume and provides efficient, reproducible, reliable and rugged formation of an electrospray. This electrospray device is perfectly suited as a means of electrospray of fluids from microchip-based separation devices. The design of this electrospray device is also robust such that the device can be readily mass-produced in a cost-effective, high-yielding process.

BRIEF DESCRIPTION OF THE DRAWINGS

FIGS. 2A to D show an electrospray system and the effect of the position of the capillary tip relative to the ring electrode on the droplet diameter of the spray.

FIG. 3C is a cross-sectional view taken along line 3C—3C of FIG. 3B. FIG. 3I is a perspective view of the injection side of the electrospray device of FIG. 3H.

FIG. 5B is taken along line 5B—5B of FIG. 5A.

FIGS. 17A–17D show another embodiment of an electrospray side fabrication sequence of an integrated liquid chromatography-electrospray device.

DETAILED DESCRIPTION OF THE INVENTION

Figure 1A:
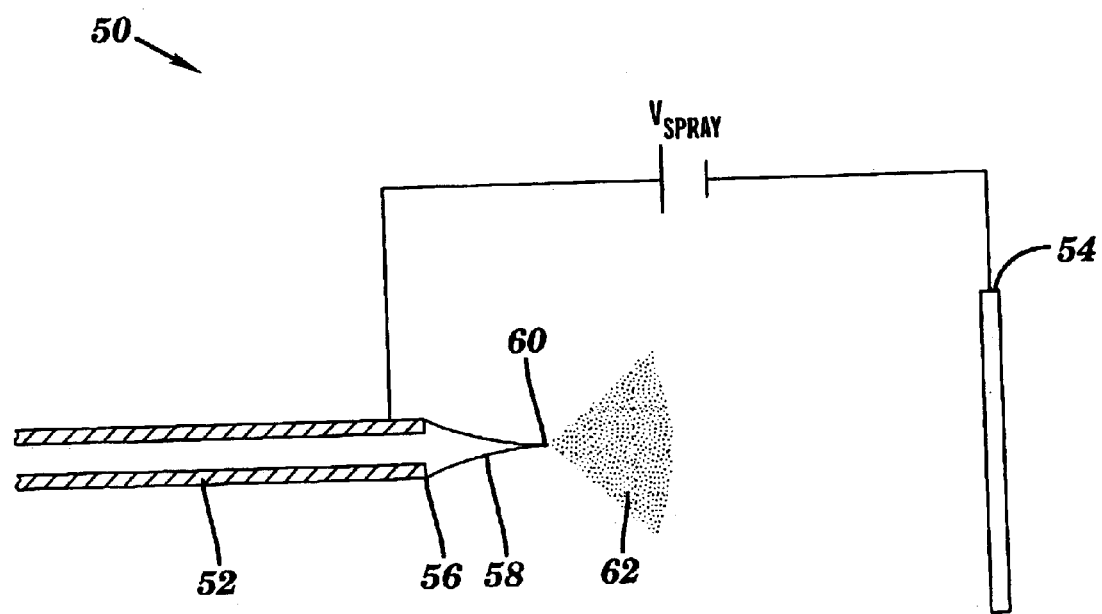
FIG. 1A shows a schematic of an electrospray system emitting small charged droplets.
Figure 1B:
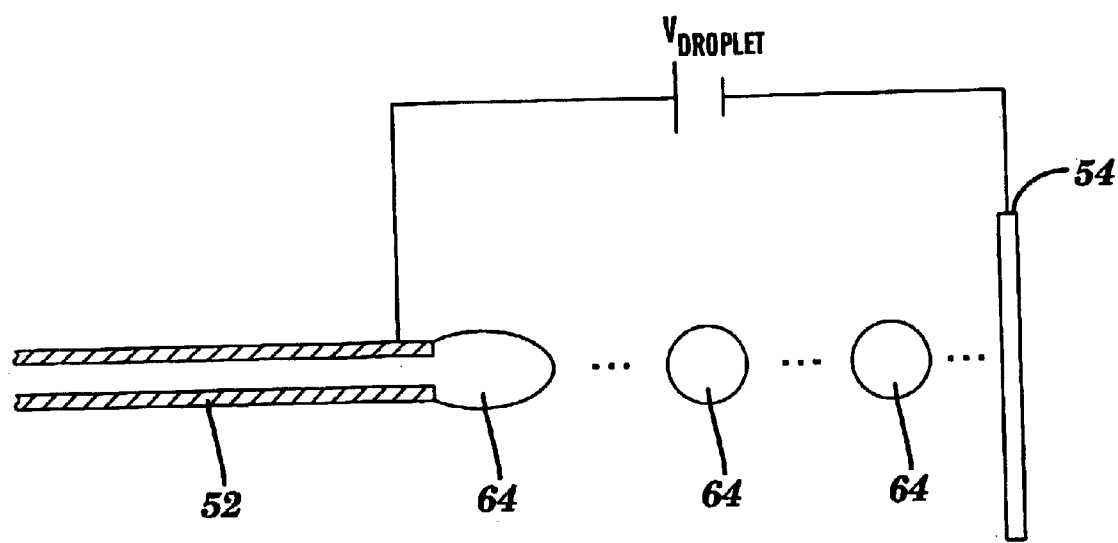
FIG. 1B shows a schematic of an electrospray system emitting poorly charged droplets.
Figure 1C:
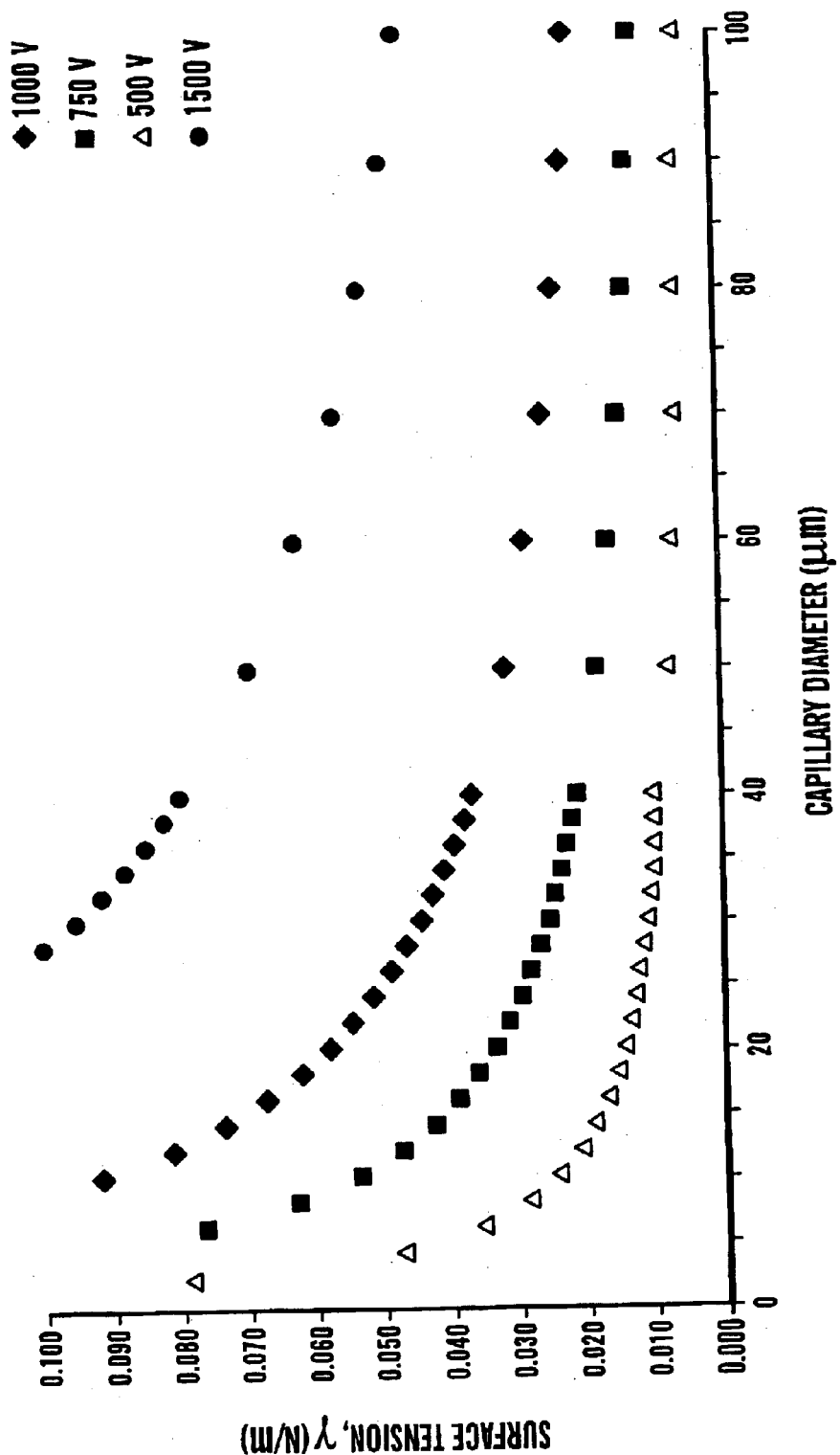
FIG. 1C shows a graph plotting the surface tension of a solution versus the capillary tip diameter for onset voltages of 500, 750, 1000, and 1500 volts and a 2 mm distance between the capillary tip and counterelectrode of an electrospray system.
Figure 2A:
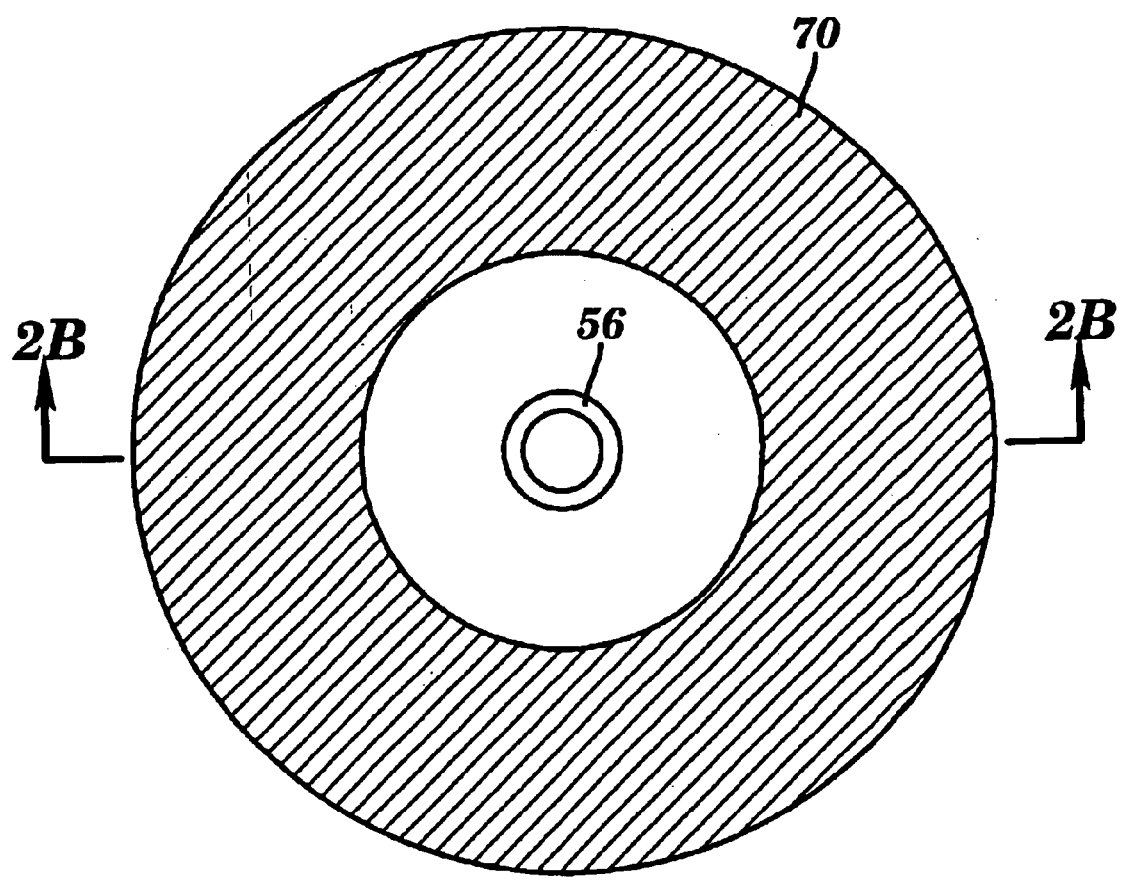
Figure 2C:
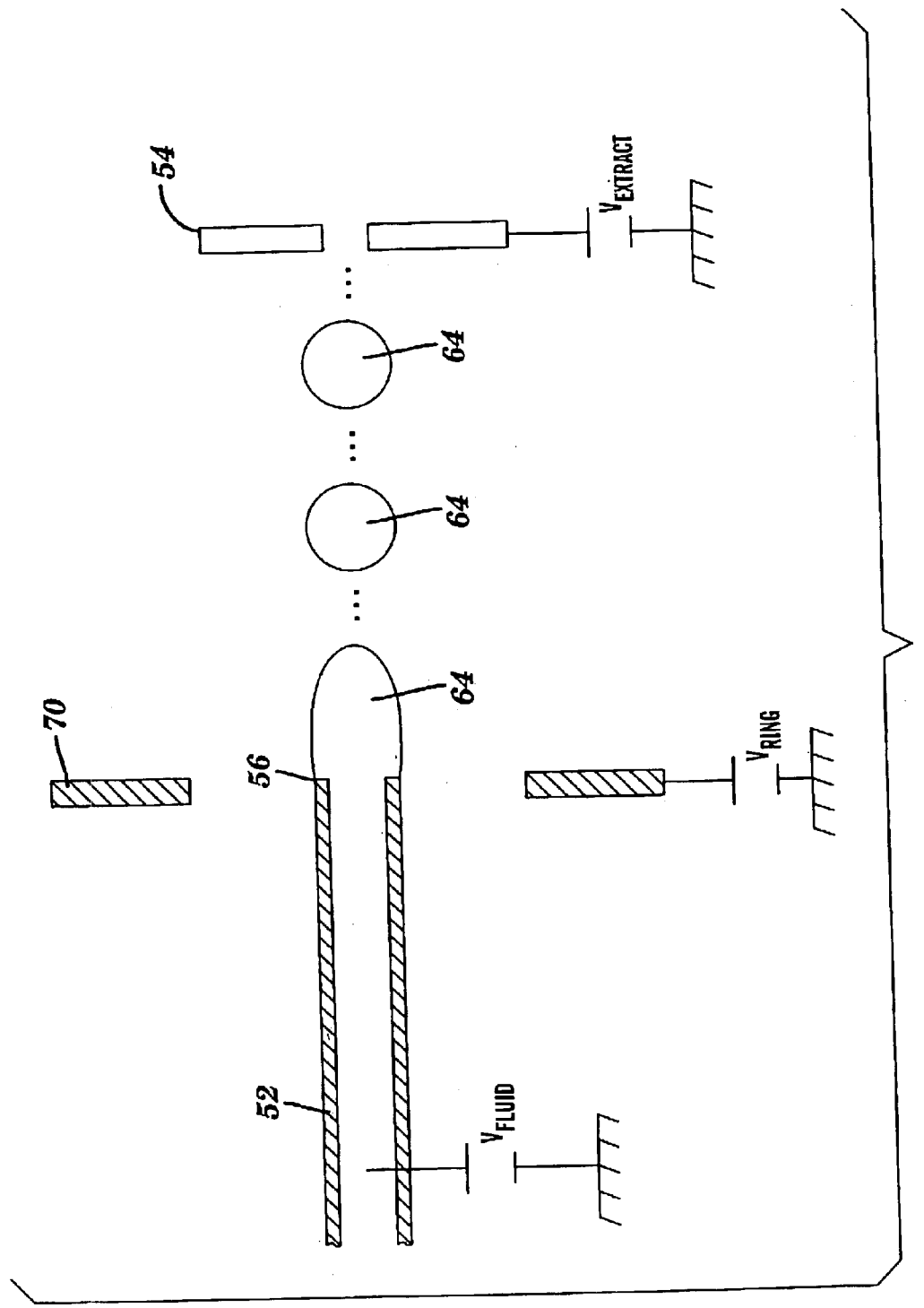
Figure 2D:
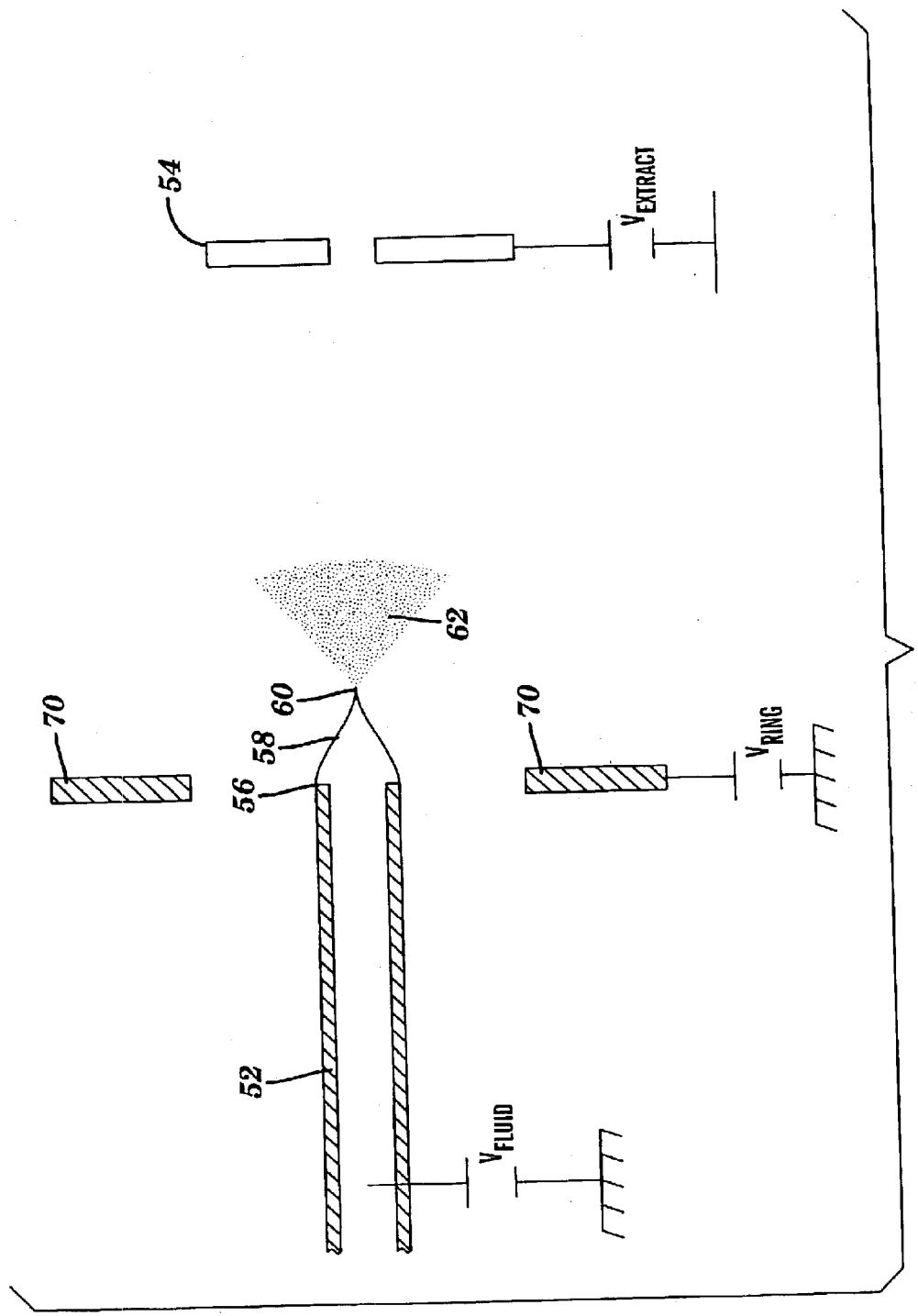
Figure 3A:
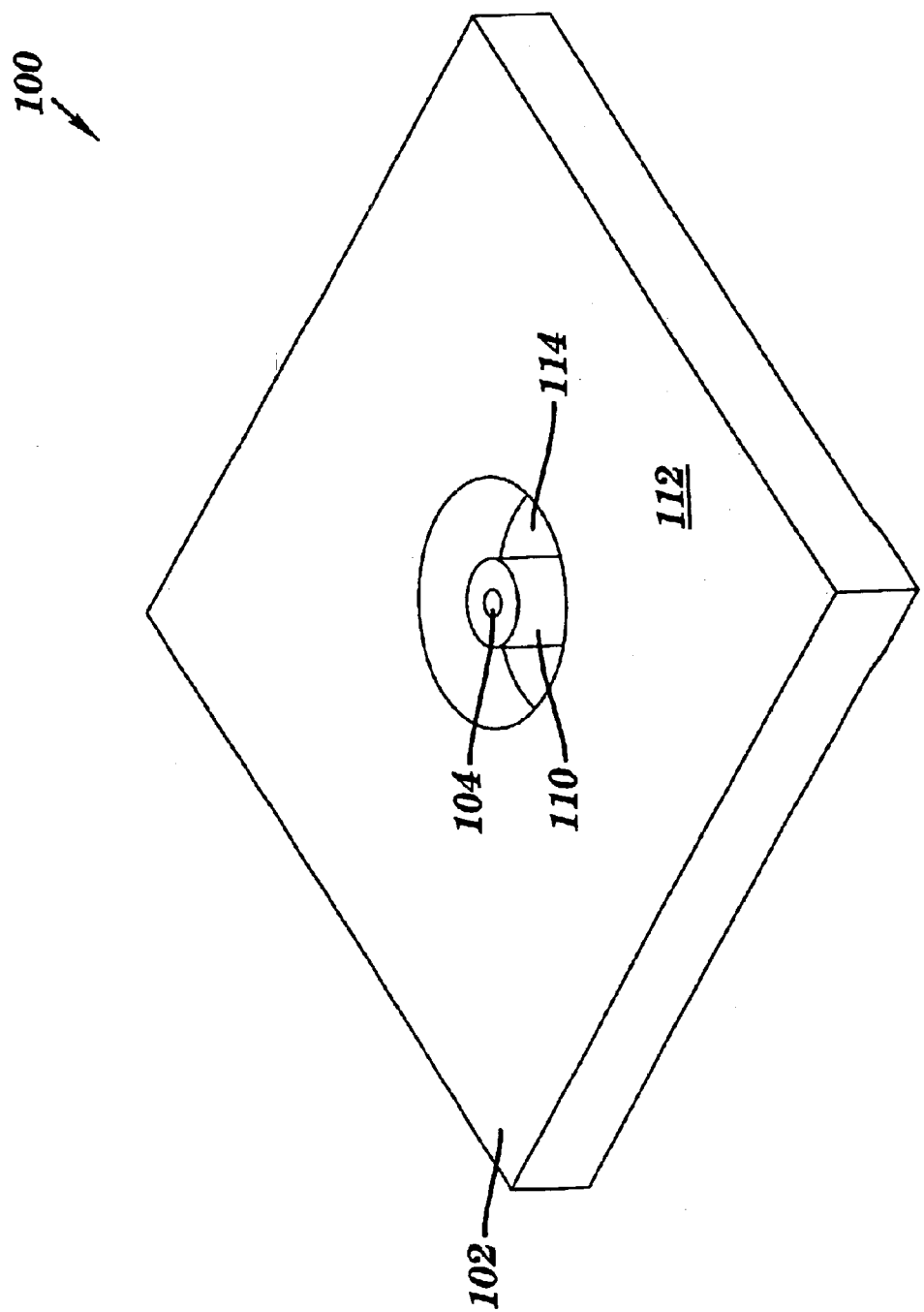
FIGS. 3A to C show, respectively, a perspective view, a plan view, and a cross-sectional view of an electrospray device in accordance with the present invention.
Figure 3B:
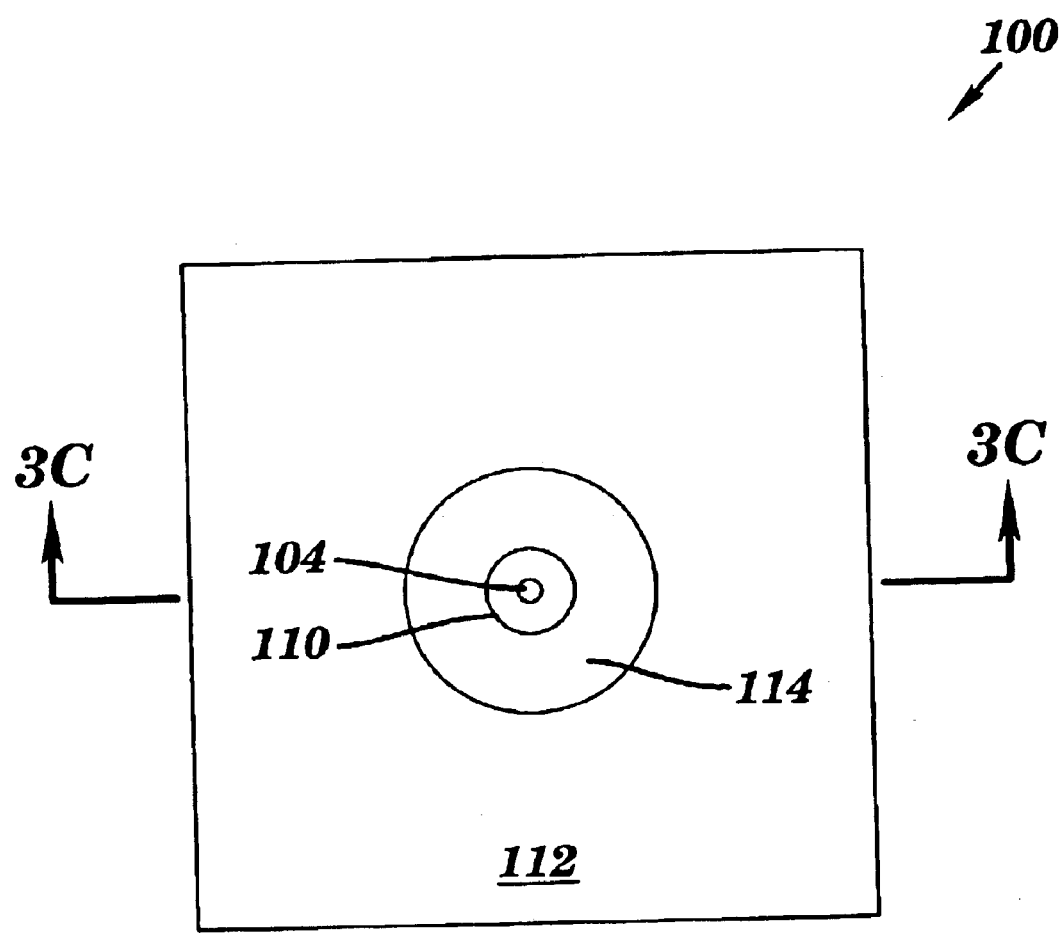
Figure 3C:
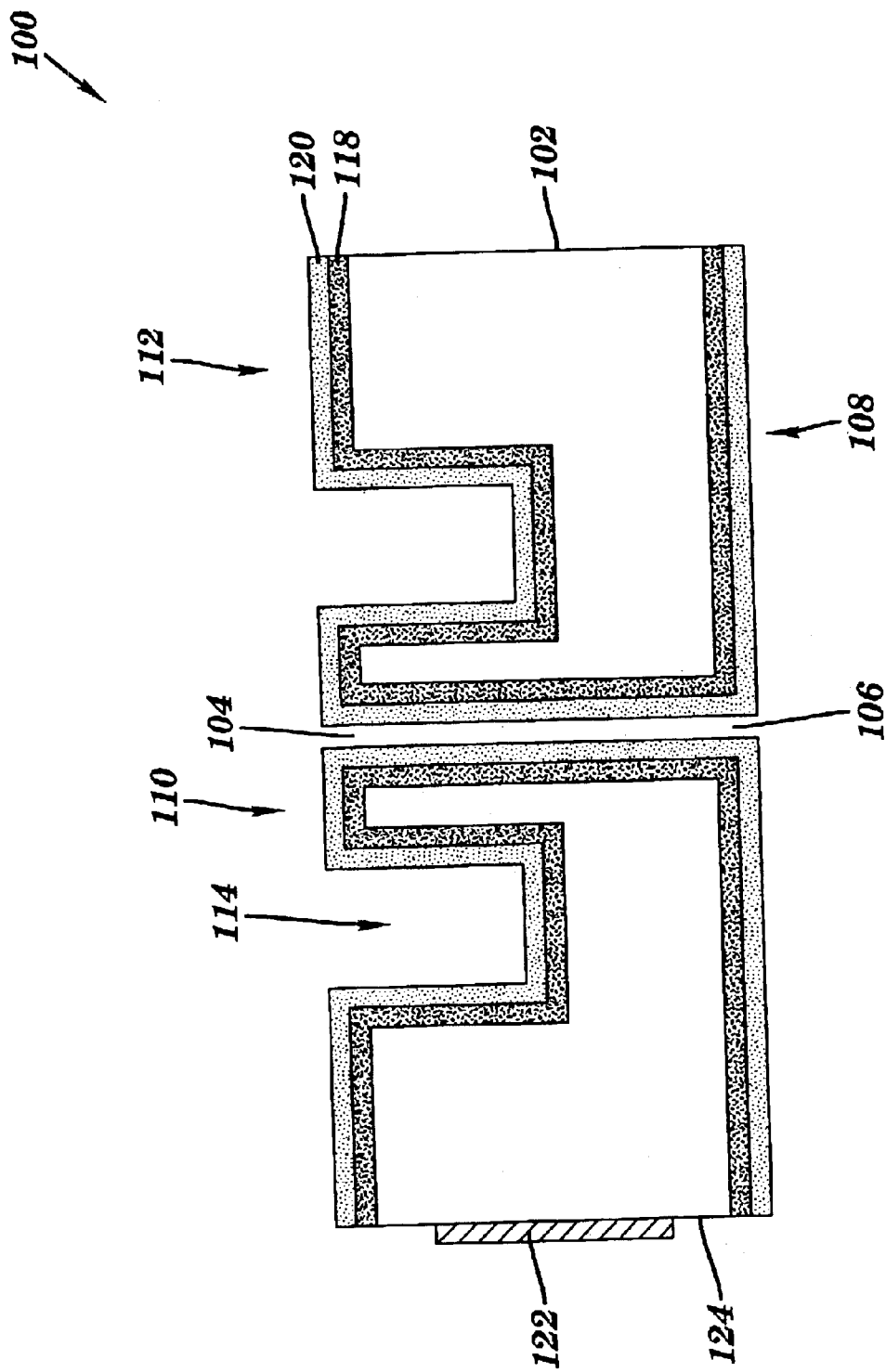

FIGS. 3A, 3B and 3C show, respectively, a perspective view, a plan view and a cross-sectional view of an electrospray device 100 of the present invention. The electrospray apparatus of the present invention generally comprises a silicon substrate, microchip or wafer 102 defining a through substrate channel 104 between an entrance orifice 106 on an injection surface 108 and a nozzle 110 on an ejection surface 112. The channel may have any suitable cross-sectional shape such as circular or rectangular. The nozzle 110 has an inner and an outer diameter and is defined by a recessed region 114. The region 114 is recessed from the ejection surface 112, extends outwardly from the nozzle 110 and may be annular. The tip of the nozzle 110 does not extend beyond and is preferably coplanar or level with the ejection surface 112 to thereby protect the nozzle 110 from accidental breakage.

Preferably, the injection surface 108 is opposite the ejection surface 112. However, the injection surface may be adjacent to the ejection surface such that the channel extending between the entrance orifice and the nozzle makes a turn within the device. In such a configuration, the electrospray device would comprise two substrates bonded together. The first substrate may define a through-substrate channel extending between a bonding surface and the ejection surface, opposite the bonding surface. The first substrate may further define an open channel recessed from the bonding surface extending from an orifice of the through-substrate channel and the injection surface such that the bonding surface of the second substrate encloses the open channel upon bonding of the first and second substrates. Alternatively, the second substrate may define an open channel recessed from the bonding surface such that the bonding surface of the first substrate encloses the open channel upon bonding of the first and second substrates. In yet another variation, the first substrate may further define a second through-substrate channel while the open channel extends between the two through-substrate channels. Thus, the injection surface is the same surface as the ejection surface.

The electrospray device 100 further comprises a layer of silicon dioxide 118 and a layer of silicon nitride 120 over the injection 108, ejection 112, and through-substrate channel 104 surfaces of the substrate 102. An electrode 122 is in contact with the substrate 102 on the edge 124 of the silicon substrate. The silicon dioxide 118 and silicon nitride 120 formed on the walls of the channel 104 electrically isolates a fluid therein from the silicon substrate 102 and, thus, allows for the independent application and sustenance of different electrical potentials to the fluid in the channel 104 and to the silicon substrate 102. Additional layers of silicon dioxide or other materials may be further deposited to provide for any required chemical functionality to the surface of the device. The ability to independently vary the fluid and substrate potentials allows the optimization of the electrospray through modification of the electric field, as described below.

Figure 3D:
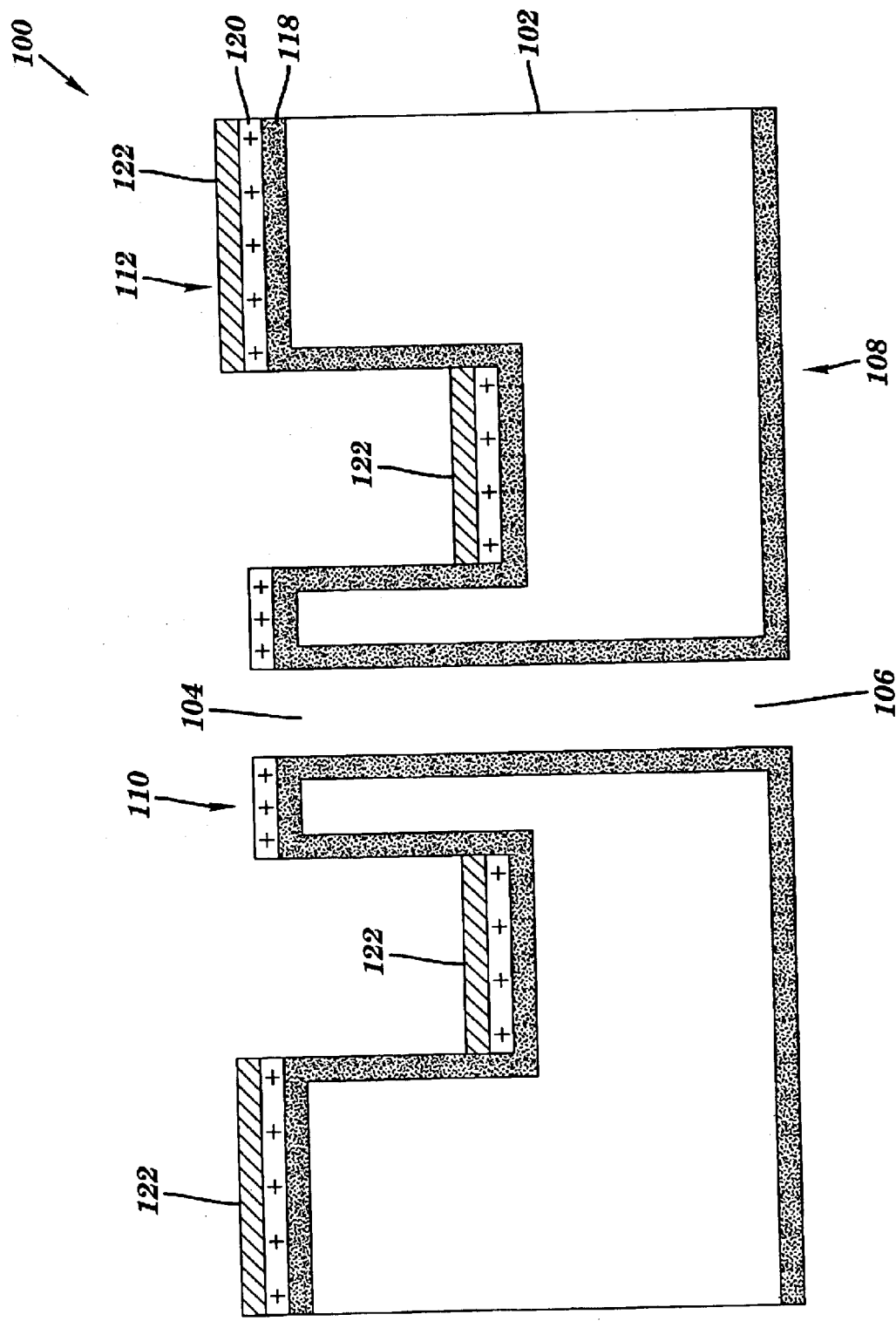
FIG. 3D shows a cross-sectional view of an alternative embodiment of an electrospray device in accordance with the present invention.

Alternatively as shown in FIG. 3D, the substrate 102 can be in electrical contact with the fluid in the through-substrate channel when appropriate for a given application. This is accomplished by selective deposition of silicon dioxide on the injection and ejection surfaces of the substrate and the through-substrate channel, followed by a selective deposition of silicon nitride 120 on the ejection surface. A region of the ejection surface 112 exterior to the nozzle 110 may provide a surface on which a conductive electrode 122 may be formed to modify the electric field between the ejection surface 112, including the nozzle tip 110, and the extracting electrode 54. In this case, the substrate potential voltage controls the electric field around the nozzle, the controlling electrodes 122 on the ejection surface 112 of the substrate 102, and the distance from the counter electrode 54.

Figure 3E:
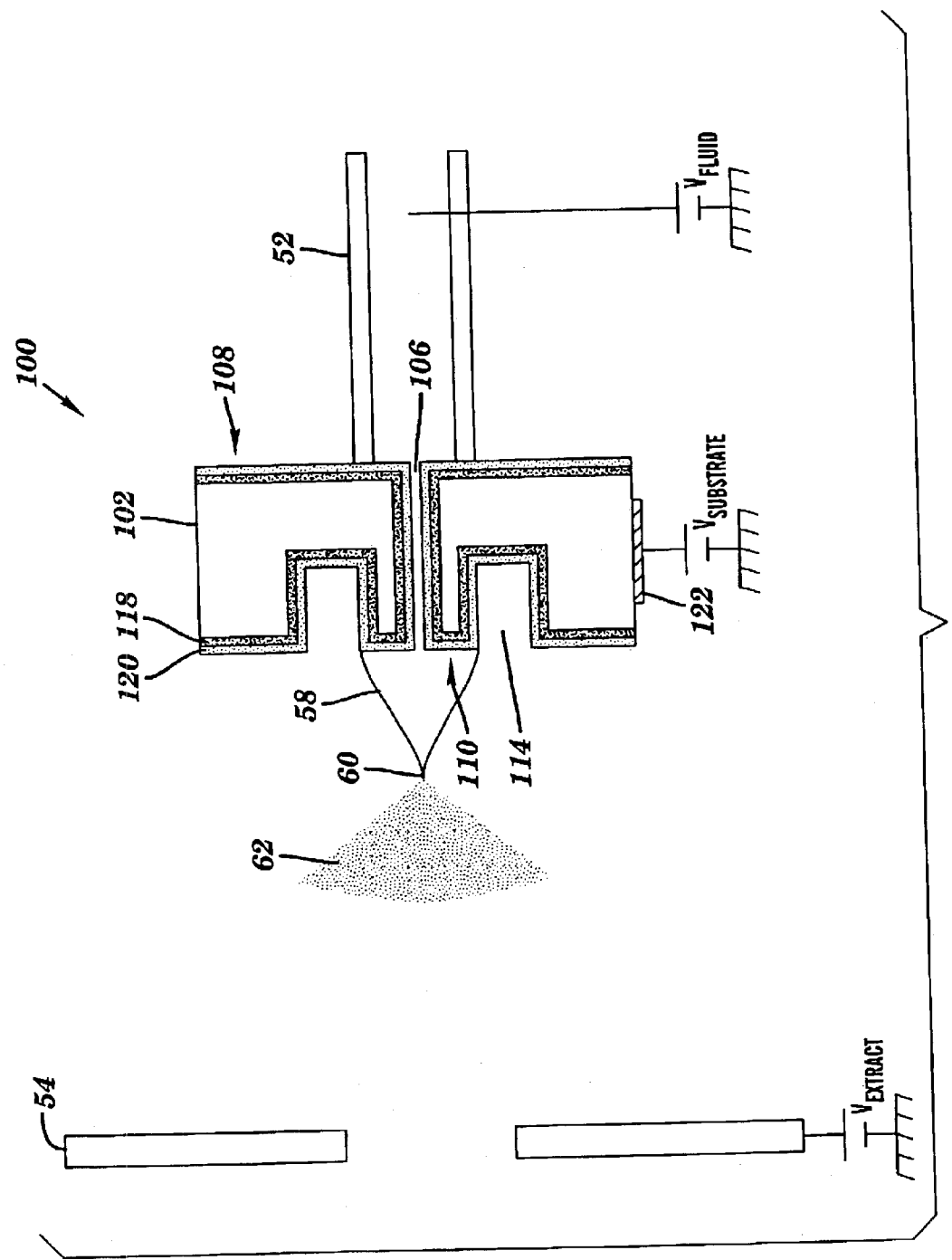
FIGS. 3E and 3F show the use of the electrospray device of the present invention to generate a fine spray and minimally charged droplets.

As shown in FIG. 3E, to generate an electrospray, fluid may be delivered to the through-substrate channel 104 of the electrospray device 100 by, for example, a capillary 52, micropipette or microchip. The fluid is subjected to a potential voltage $V_{fluid}$ via a wire positioned in the capillary 52 or via an electrode provided on the injection surface 108 and isolated from the surrounding surface region and the substrate 102. A potential voltage $V_{substrate}$ may also be applied to the electrode 122 on the edge 124 of the silicon substrate 102 the magnitude of which is preferably adjustable for optimization of the electrospray characteristics. The fluid flows through the channel 104 and exits from the nozzle 110 in the form of a Taylor cone 58, liquid jet 60, and very fine, highly charged fluidic droplets 62. The electrode 54 may be held at a potential voltage $V_{extract}$ such that the highly-charged fluidic droplets are attracted toward the extracting electrode 54 under the influence of an electric field.

In one embodiment, the nozzle 110 may be placed up to 10 mm from the ion-sampling orifice of an API mass spectrometer that may function as the extracting electrode 54. A potential voltage $V_{fluid}$ ranging from approximately 500–1000 V, such as 700 V, is applied to the fluid. A potential voltage of the substrate $V_{substrate}$ of less than half of the fluid potential voltage $V_{fluid}$, or 0–350 V, is applied to the substrate to enhance the electric field strength at the tip of the nozzle 110. The extracting electrode 54 may be held at or near ground potential $V_{extract}$ (0 V). Thus, a nanoelectrospray of a fluid introduced to the electrospray device 100 is attracted toward the extracting electrode 54.

The nozzle 110 provides the physical asperity to promote the formation of a Taylor cone and efficient electrospray of a fluid. The nozzle 110 also forms a continuation of and serves as an exit orifice of the through-substrate channel 104. The recessed region 114 serves to physically isolate the nozzle 110 from the ejection surface 112. The present invention allows the optimization of the electric field lines emanating from the fluid exiting the nozzle 110 through independent control of the potential voltage $V_{fluid}$ of the fluid and the potential voltage $V_{substrate}$ of the substrate.

Dimensions of the electrospray device 100 can be determined according to various factors such as the specific application, the layout design as well as the upstream and/or downstream device to which the electrospray device 100 is interfaced or integrated. Further, the dimensions of the channel and nozzle may be optimized for the desired flow rate of the fluid sample. The use of reactive-ion etching techniques allows for the reproducible and cost effective production of small diameter nozzles, for example, a 2 µm inner diameter and 5 µm outer diameter.

In one currently preferred embodiment, the silicon substrate 102 of the electrospray device 100 is approximately 250–300 µm in thickness and the cross-sectional area of the through-substrate channel 104 is less than approximately 2,500 µm². Where the channel 104 has a circular cross-sectional shape, the channel 104 and the nozzle 110 have an inner diameter of up to 50 µm, more preferably up to 30 µm; the nozzle 110 has an outer diameter of up to 60 µm, more preferably up to 40 µm: and nozzle 110 has a height of (and the recessed portion 114 has a depth of) up to 100 µm. The recessed portion 114 preferably extends up to 300 µm outwardly from the nozzle 110. The silicon dioxide layer 118 has a thickness of approximately 1–4 µm, preferably 1–3 µm. The silicon nitride layer 120 has a thickness of approximately less than 2 µm.

Figure 3F:
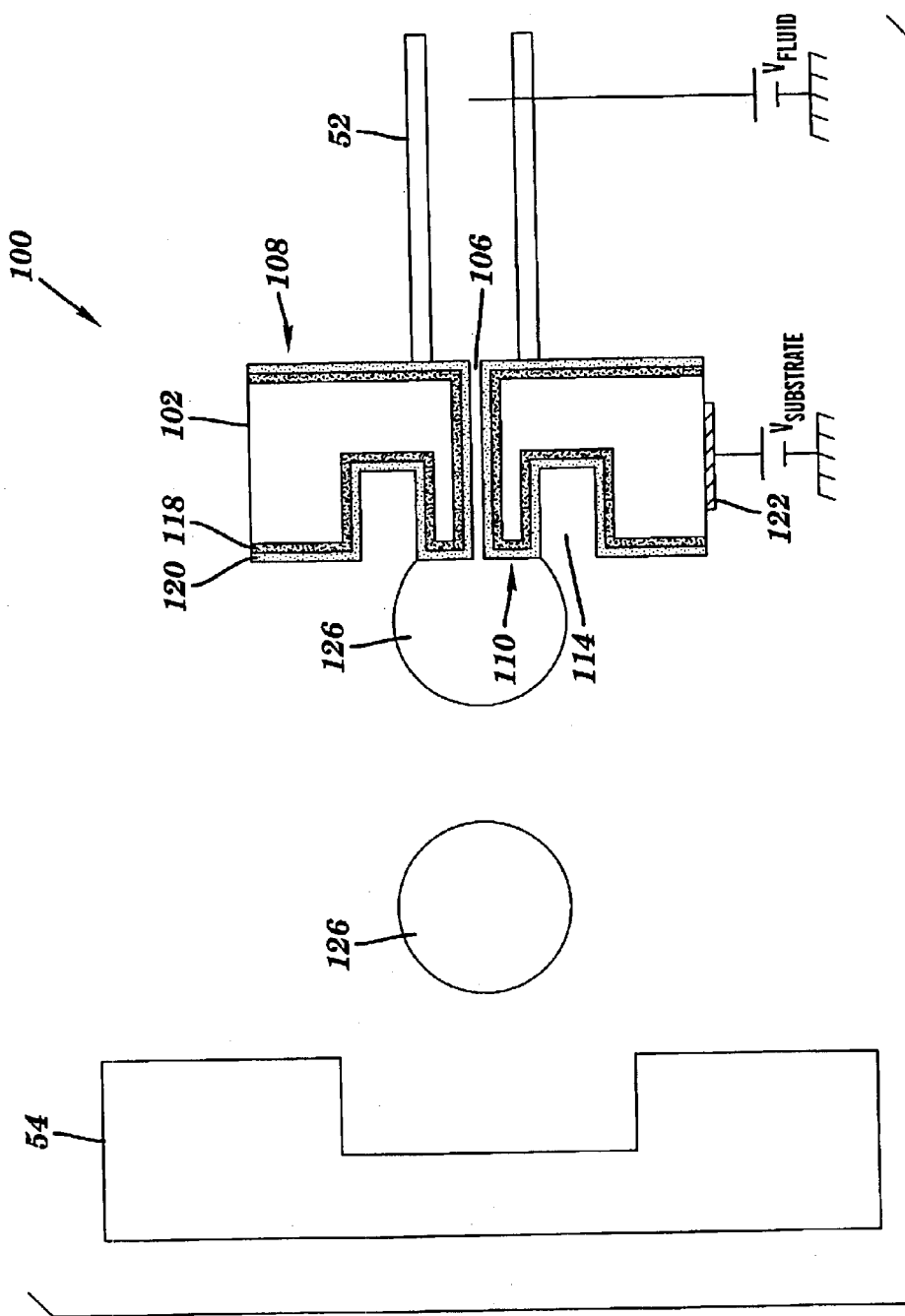

Furthermore, the electrospray device may be operated to produce larger, minimally-charged droplets 126 as shown in FIG. 3F. This is accomplished by decreasing the electric field at the nozzle exit to a value less than that required to generate an electrospray of a given fluid. Adjusting the ratio of the potential voltage $V_{fluid}$ of the fluid and the potential voltage $V_{substrate}$ of the substrate controls the electric field. A $V_{fluid}/V_{substrate}$ ratio approximately less than 2 is required for droplet formation. The droplet diameter in this mode of operation is dependent on the nozzle diameter, electric field strength, and fluid surface tension. This mode of operation is ideally suited for conveyance and/or apportionment of a multiplicity of discrete amounts of fluids, and may find use in such devices as ink jet printers and equipment and instruments requiring controlled distribution of fluids.

Figure 3G:
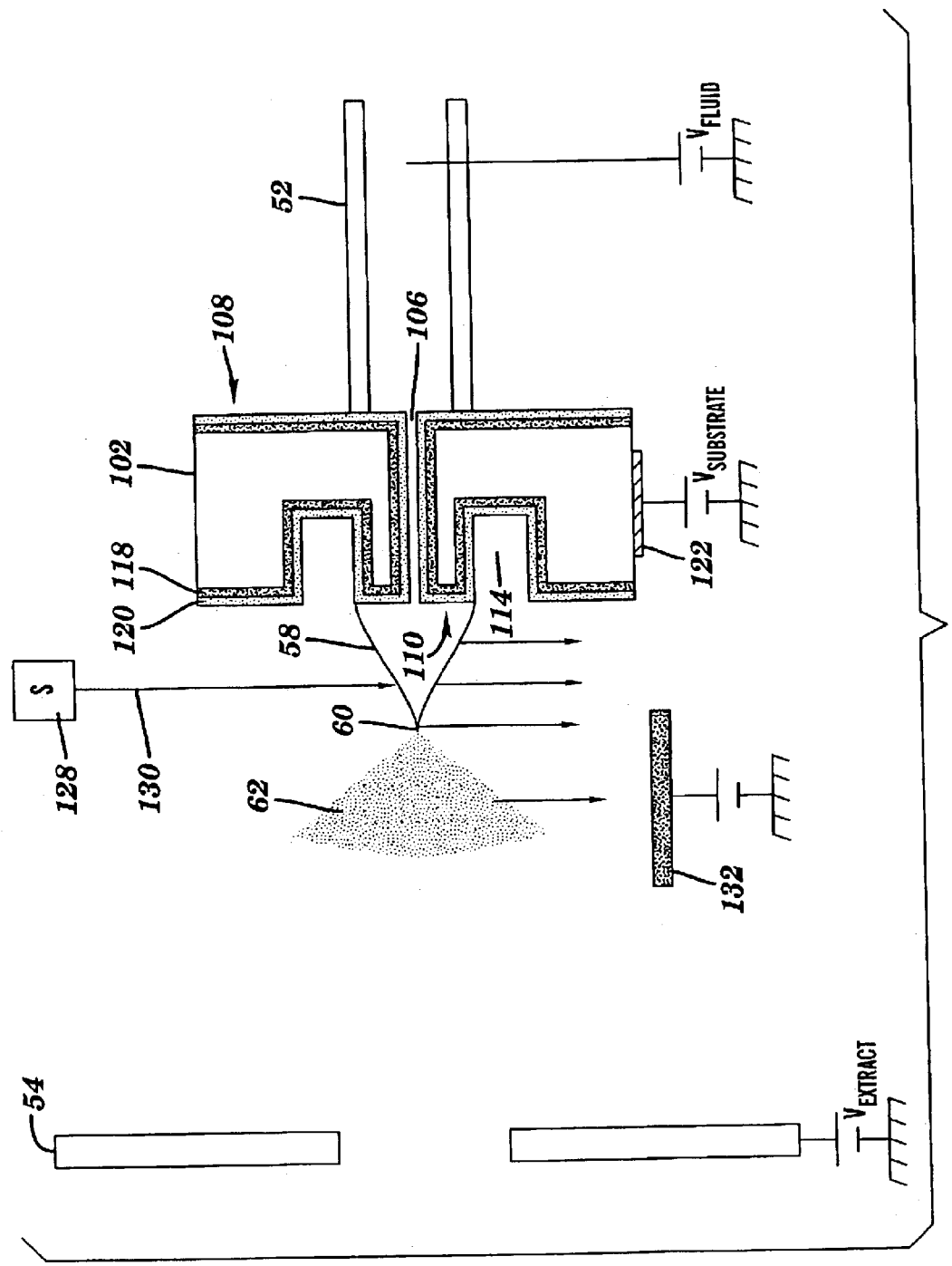
FIG. 3G shows the use of the electrospray device of the present invention in conjunction with a minaturized monolithic chromatography or other liquid sample handling device.

This fully integrated monolithic electrospray device may be coupled with a miniaturized monolithic chromatography or other liquid sample handing devices. FIG. 3G shows this electrospray device used as a means of producing a fluidic cone for spectroscopic detection including laser induced fluorescence, ultraviolet absorption, and evaporative light scattering and mass spectrometry detection. An excitation source 128 provides a light beam 130. A detector 132 detects the emission or absorbance or light scattering properties of the analytes in the fluidic Taylor cone 58, liquid jet 60, or highly-charged droplets 62.

Figure 3H:
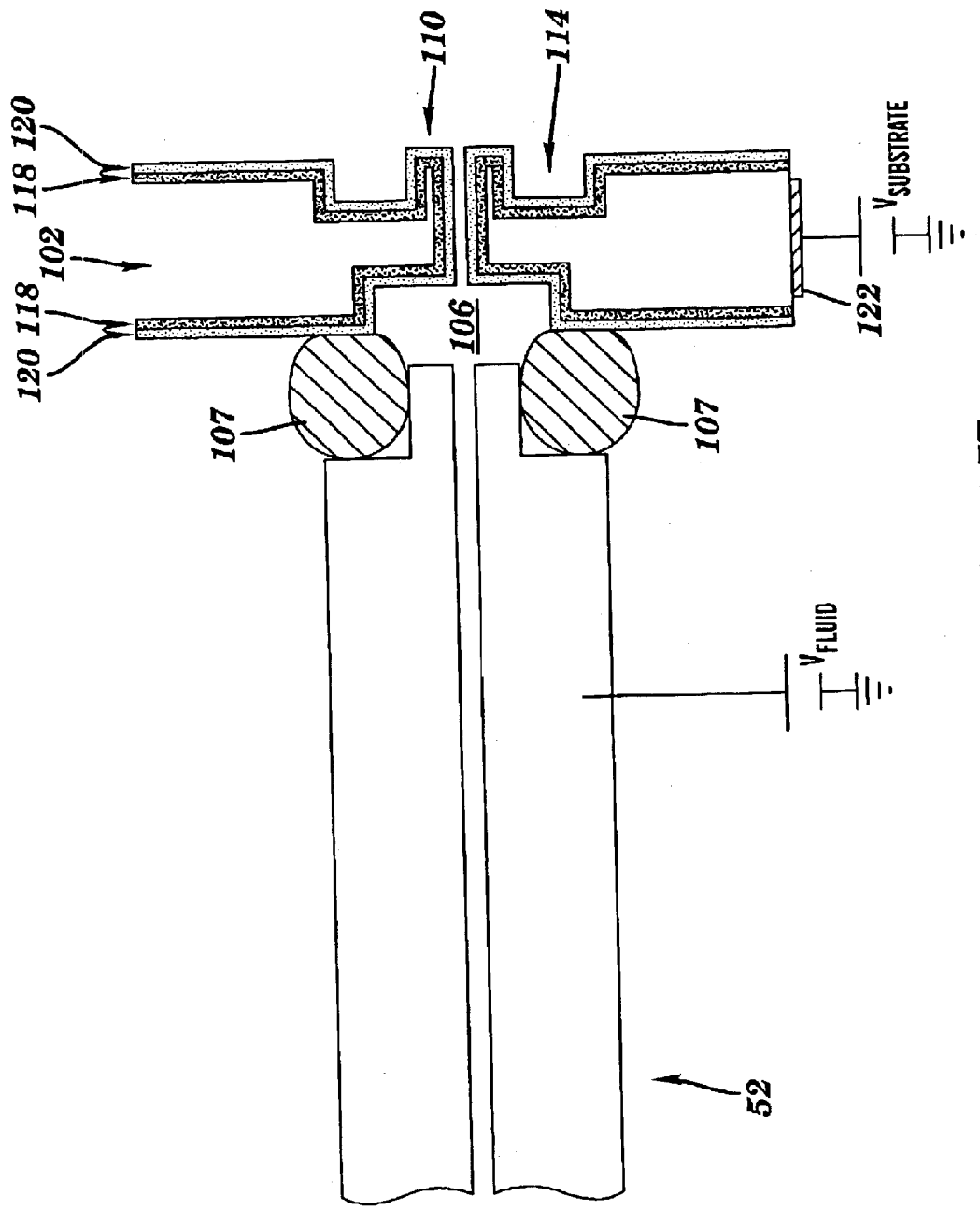
FIG. 3H is a cross-sectional view showing the electrospray device of the present invention coupled with a fluidic probe.
Figure 31:
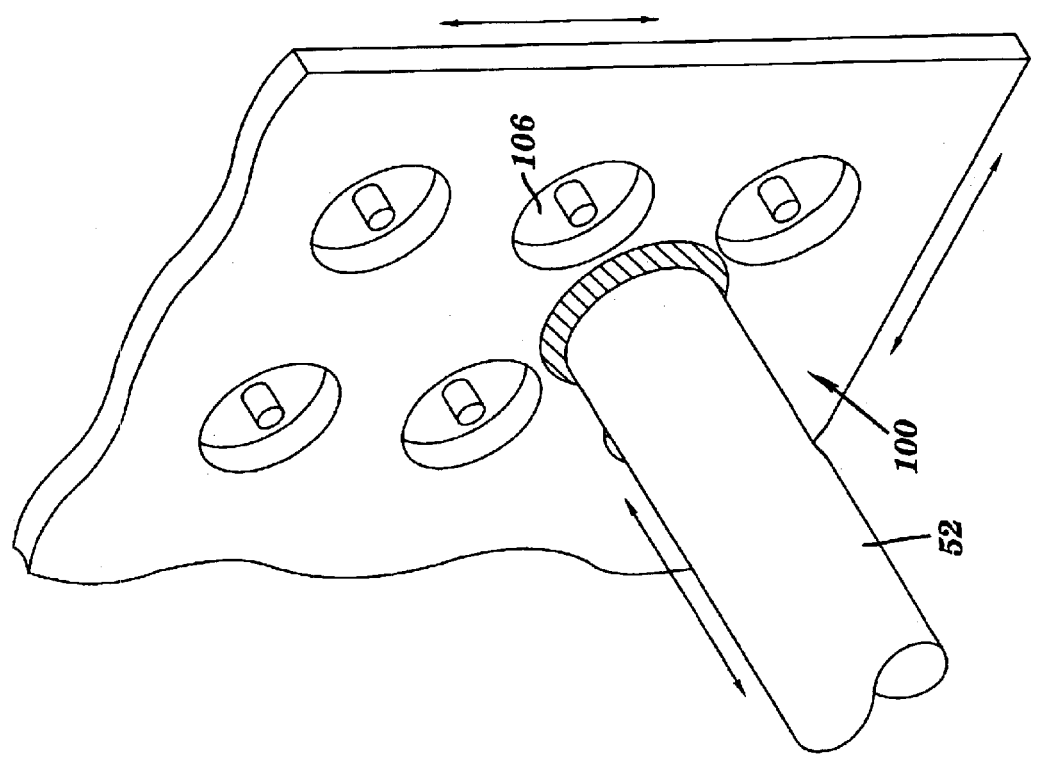

FIG. 3H shows the use of the electrospray device of the present invention interfaced with a liquid sample handling device showing a means of sealing the liquid handling device to the injection side of the present invention. The figure shows an O-ring seal 107 between the liquid sample handling device 52 and the electrospray device 110. FIG. 3I shows an array of electrospray devices 106 fabricated on a monolithic substrate 100 and interfacing to a liquid sample handling device 52. More than one liquid sample handling device could be interfaced with an array of electrospray devices. Only one is shown for clarity.

Figure 4A:
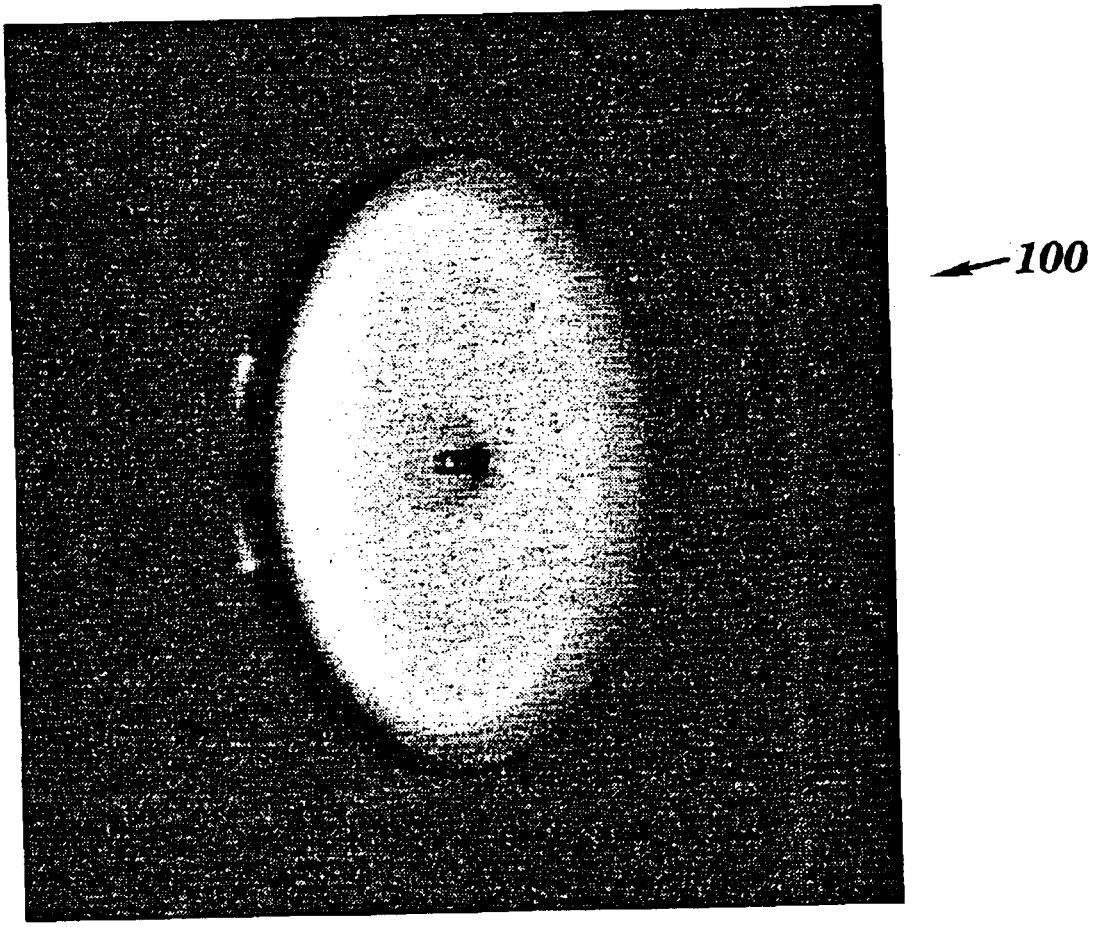
FIG. 4A is a photograph showing an electrospray device in accordance with the present invention.
Figure 4B:
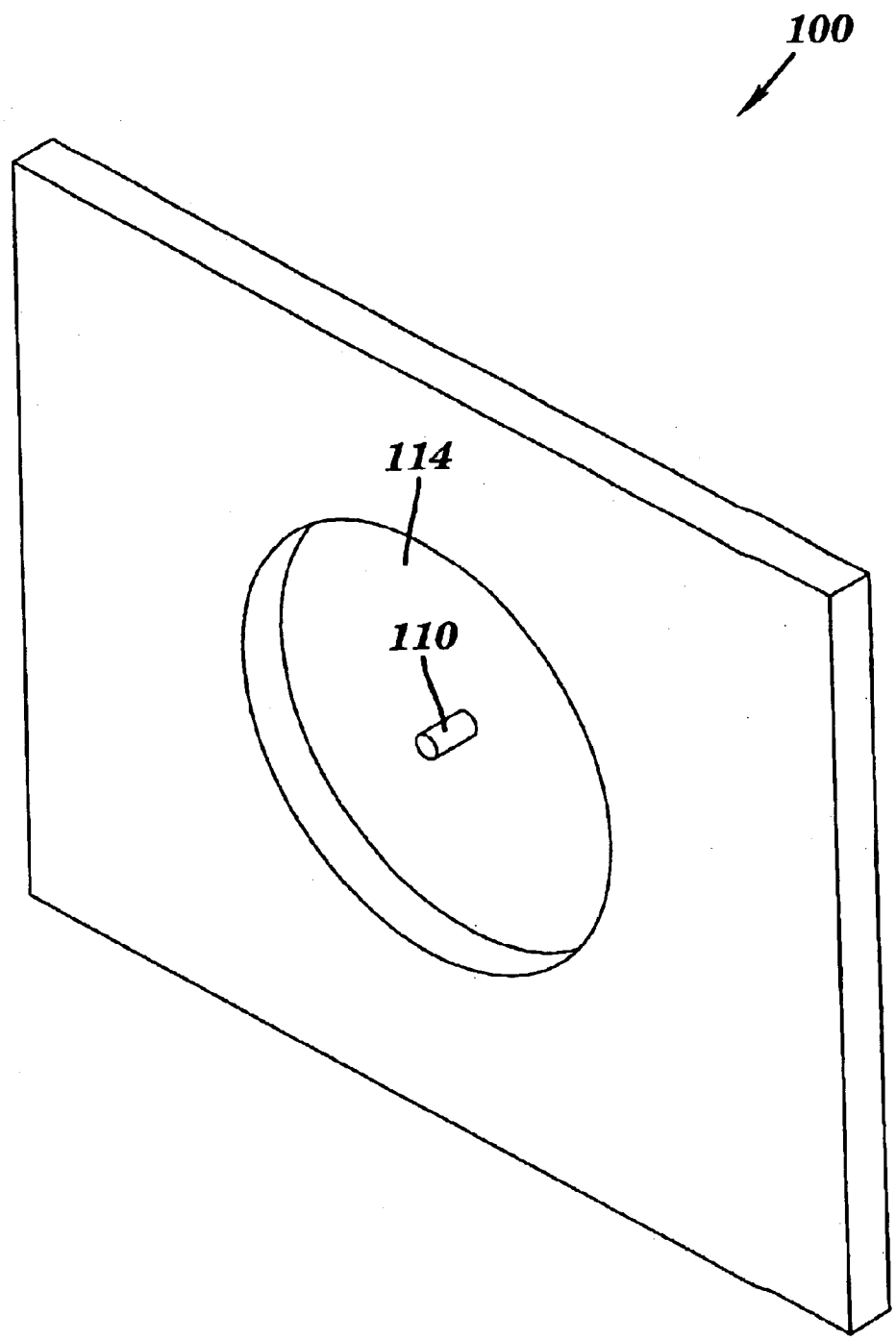
FIG. 4B is a perspective view of an electrospray device in accordance with the present invention.
Figure 4C:
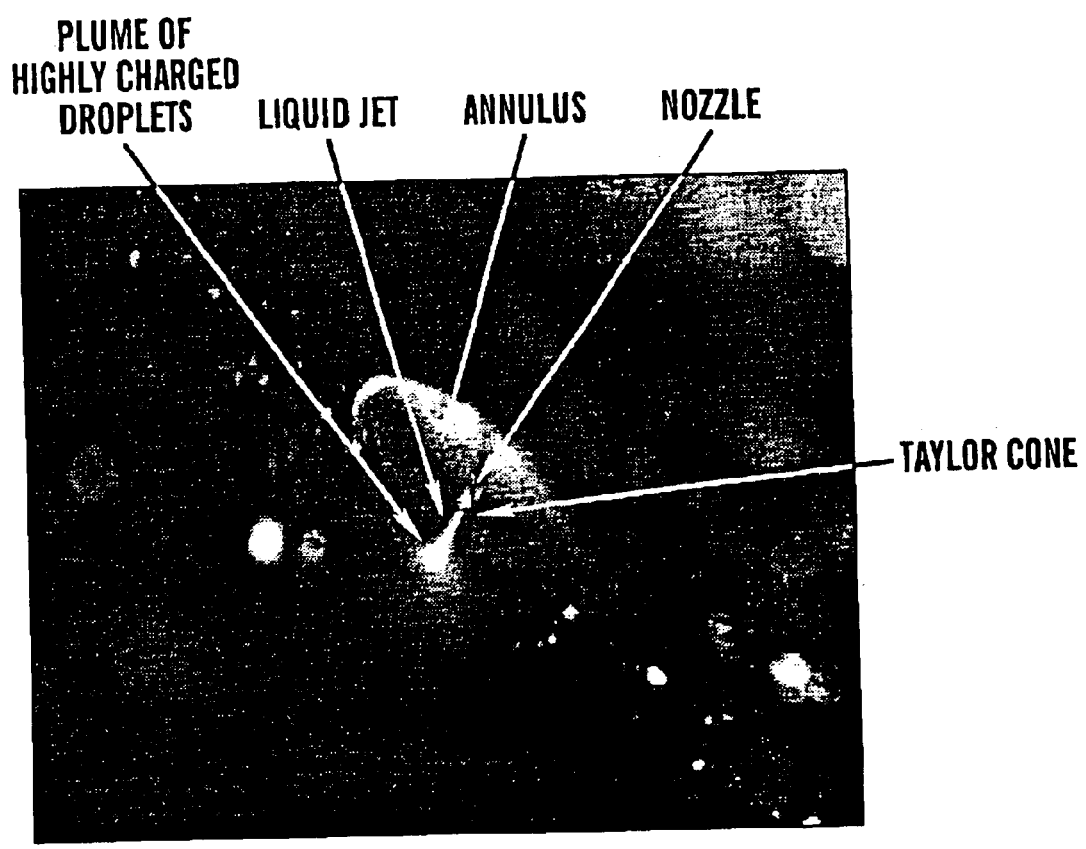
FIG. 4C shows a perspective view of an electrospray device in accordance with the present invention generating an electrospray.

FIG. 4A shows a perspective view picture (approximately 80 times magnified) of an electrospray device 100 consisting of a nozzle etched in a silicon substrate. FIG. 4B is a perspective view on an electrospray device in accordance with the present invention. Nozzle 110 has a 20 µm outer diameter and 15 µm inner diameter (through-substrate channel) with a height of 70 µm. The nozzle walls are 2.5 µm in thickness. The recessed annular region 114 has a radius of 300 µm. The substrate 102 has a thickness of 254 µm. FIG. 4C shows a perspective view picture of an electrospray device generating an electrospray. In this figure, a 50% water:50% methanol solution containing 500 ng/mL of reserpine is being introduced to the injection side 108 of the through-substrate channel 104 as shown in FIG. 3G. The fluid flow is controlled using a syringe pump set at a flow rate of 100 nL/min. A fluid voltage of 700 V is applied to a stainless steel capillary 52 (not shown) with the substrate held at zero V. The counter electrode 54 (not shown) is an ion-sampling orifice of a Micromass LCT time-of-flight mass spectrometer held at 80 V. The nozzle is approximately 5 mm from the ion-sampling orifice of the mass spectrometer. Labeled in FIG. 4C is a real Taylor cone emanating from a nozzle, a liquid jet, a plume of highly-charged droplets and a recessed annular region.

Figure 4D:
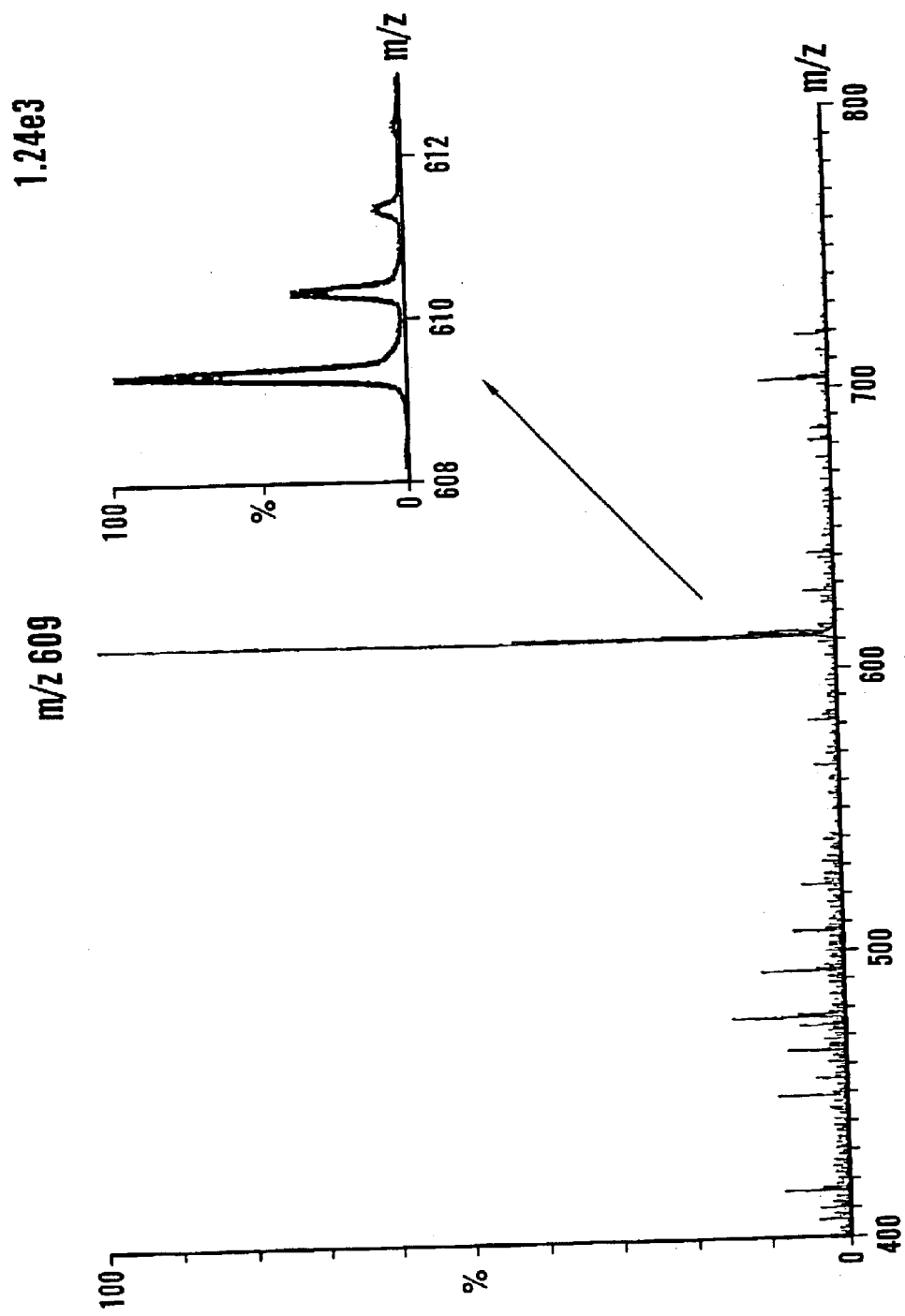
FIG. 4D is a mass spectrum of a Resperine solution sprayed from the electrospray device of the present invention.
Figure 4E:
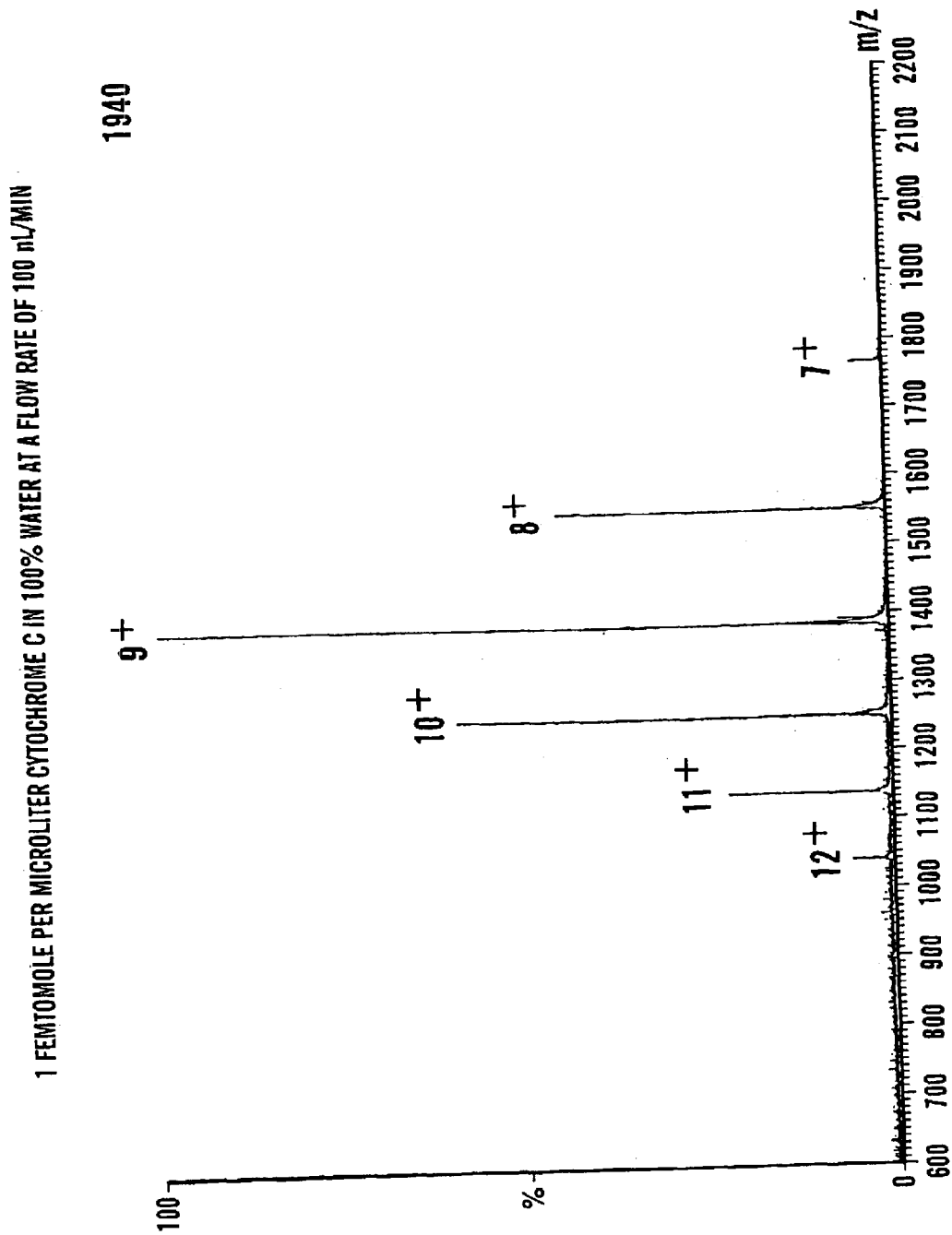
FIG. 4E is a mass spectrum of 1 nM of Cytochrome C solution sprayed from the electrospray device of the present invention.
Figure 4F:
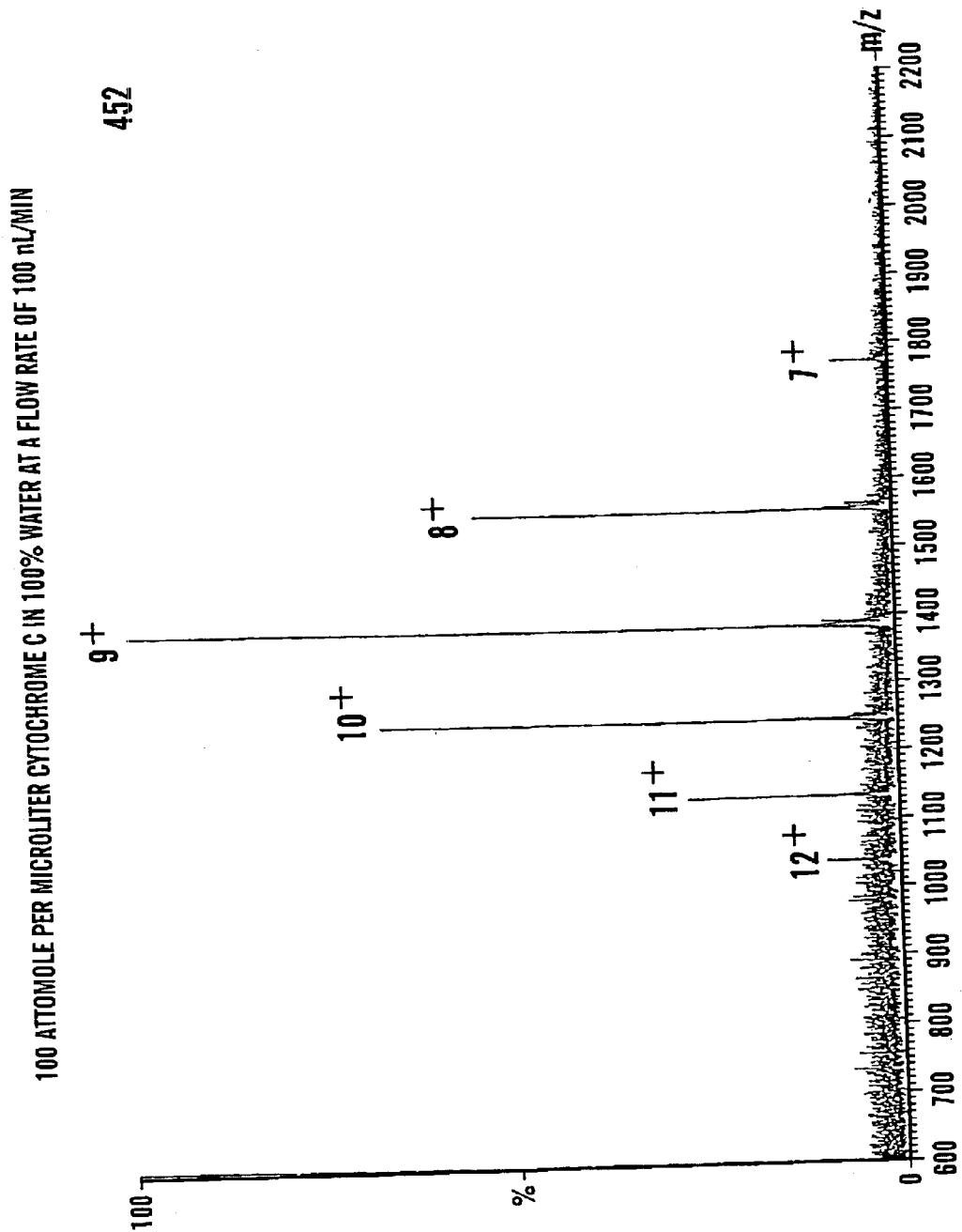
FIG. 4F is a mass spectrum of 0.1 nM of Cytochrome C solution sprayed from the electrospray device of the present invention.

FIG. 4D shows the electrospray mass spectrum acquired from the electrospray shown in FIG. 4C for the Reserpine solution. Reserpine has a molecular weight of 608 Da. Electrospray in positive ion mode results in the protonation of the molecular molecule resulting in an ion at m/z 609. A region of the m/z range from 608 to 613 is inserted to show the separation of the isotopes of reserpine. FIG. 4E shows the electrospray mass spectrum acquired from the electrospray of a 1 nM (1 femtomole per microliter) solution of Cytochrome C in 100% water. The solution flow rate is 100 nL/min with a fluid voltage of 1350 V and a substrate voltage of zero V. The mass spectrum shows the multiple-charge distribution characteristic of large biomolecules from electrospray ionization (peaks are labeled with the respective charge state). FIG. 4F shows the electrospray mass spectrum acquired from the electrospray of a 0.1 nM (100 attomole per microliter) solution of Cytochrome C in 100% water at a flow rate of 100 nL/min.

The electrospray device of the present invention generally comprises a silicon substrate material defining a channel between an entrance orifice on an injection surface and a nozzle on an ejection surface (the major surface) such that the electrospray generated by the device is generally perpendicular to the ejection surface. The nozzle has an inner and an outer diameter and is defined by an annular portion recessed from the ejection surface. The annular recess extends radially from the outer diameter. The tip of the nozzle is co-planar or level with and does not extend beyond the ejection surface. Thus, the nozzle is protected against accidental breakage. The nozzle, the channel, and the recessed portion are etched from the silicon substrate by reactive-ion etching and other standard semiconductor processing techniques.

All surfaces of the silicon substrate preferably have insulating layers to electrically isolate the liquid sample from the substrate and the ejection and injection surfaces from each other such that different potential voltages may be individually applied to each surface and the liquid sample. The insulating layer generally consists of a silicon dioxide layer combined with a silicon nitride layer. The silicon nitride layer provides a moisture barrier against water and ions from penetrating through to the substrate causing electrical breakdown between a fluid moving in the channel and the substrate. The electrospray apparatus further comprises at least one controlling electrode electrically contacting the substrate for the application of an electric potential to the substrate.

In another embodiment, all surfaces of the silicon substrate have insulating layers thereon to electrically isolate all surfaces of the substrate from each other such that different potential voltages may be individually applied to each surface and the liquid. The insulating layer is selectively removed from the tip of the nozzle therefore, making an electrical contact between the tip of the nozzle and the substrate. Fluid exiting the nozzle will be at the potential voltage applied to the substrate. A layer of conductive metal may be selectively deposited on the ejection surface of the substrate to provide for enhancement of the electric field at the tip of the nozzle. Alternatively, this electrode may be removed from the substrate altogether and reside in close proximity to the ejection surface of the substrate to enhance the electric field emanating from the tip of the nozzle when held at an appropriate voltage. One advantage to this design is that the insulating layer on the surface of the silicon substrate no longer determines the maximum difference in the voltage applied to the fluid relative to the substrate used to enhance the electric field at the tip of the nozzle. This will allow for higher potential voltages to be applied to the fluid and, therefore, provide greater flexibility in the optimization of the electrospray.

Preferably, the nozzle, channel and recess are etched from the silicon substrate by reactive-ion etching and other standard semiconductor processing techniques. The injection-side features, through-substrate fluid channel, ejection-side features, and controlling electrodes are formed monolithically from a monocrystalline silicon substrate—i.e., they are formed during the course of and as a result of a fabrication sequence that requires no manipulation or assembly of separate components.

Because the electrospray device is manufactured using reactive-ion etching and other standard semiconductor processing techniques, the dimensions of such a device can be very small, for example, as small as 2 $\mu$m inner diameter and 5 $\mu$m outer diameter. Thus, a through-substrate fluid channel having, for example, 5 $\mu$m inner diameter and a substrate thickness of 250 $\mu$m only has a volume of 4.9 pL (picoliters). The micrometer-scale dimensions of the electrospray device minimize the dead volume and thereby increase efficiency and analysis sensitivity when combined with a separation device.

The electrospray device of the present invention provides for the efficient and effective formation of an electrospray. By providing an electrospray surface from which the fluid is ejected with dimensions on the order of micrometers, the electrospray device limits the voltage required to generate a Taylor cone as the voltage is dependent upon the nozzle diameter, the surface tension of the fluid, and the distance of the nozzle from an extracting electrode. The nozzle of the electrospray device provides the physical asperity on the order of micrometers on which a large electric field is concentrated. Further, the electrospray device may provide additional electrode(s) on the ejecting surface to which electric potential(s) may be applied and controlled independent of the electric potentials of the fluid and the substrate in order to advantageously modify and optimize the electric field for the purpose of focusing the gas phase ions produced by electrospray.

The microchip-based electrospray device of the present invention provides minimal extra-column dispersion as a result of a reduction in the extra-column volume and provides efficient, reproducible, reliable and rugged formation of an electrospray. This electrospray device is perfectly suited as a means of electrospray of fluids from microchip-based separation devices. The design of this electrospray device is also robust such that the device can be readily mass-produced in a cost-effective, high-yielding process.

In operation, a conductive or partly conductive liquid sample is introduced into the through-substrate channel entrance orifice on the injection surface. The liquid is held at a potential voltage, either by means of a wire within the fluid delivery channel to the electrospray device or by means of an electrode formed on the injection surface isolated from the surrounding surface region and from the substrate. The electric field strength at the tip of the nozzle is enhanced by the application of a voltage to the substrate and/or the ejection surface, preferably zero volts up to approximately less than one-half of the voltage applied to the fluid. Thus, by the independent control of the fluid/nozzle and substrate/ejection surface voltages, the electrospray device of the present invention allows the optimization of the electric field emanating from the nozzle. The electrospray device of the present invention may be placed 1–2 mm or up to 10 mm from the orifice of an atmospheric pressure ionization (API) mass spectrometer to establish a stable nanoelectrospray at flow rates as low as 20 nL/min.

The electrospray device may be interfaced or integrated downstream to a sampling device, depending on the particular application. For example, the analyte may be electrosprayed onto a surface to coat that surface or into another device for purposes of conveyance, analysis, and/or synthesis. As described above with reference to FIGS. 3A–C and 4A–C, highly charged droplets are formed at atmospheric pressure by the electrospray device from nanoliter-scale volumes of an analyte. The highly charged droplets produce gas-phase ions upon sufficient evaporation of solvent molecules which may be sampled, for example, through an ion-sampling orifice of an atmospheric pressure ionization mass spectrometer (API-MS) for analysis of the electrosprayed fluid.

Multiple Array of Electrospray Devices

One embodiment of the present invention is in the form of a multiple array of electrospray devices which allows for massive parallel processing. The multiple electrospray devices or systems fabricated by massively parallel processing on a single wafer may then be cut or otherwise separated into multiple devices or systems.

Figure 5A:
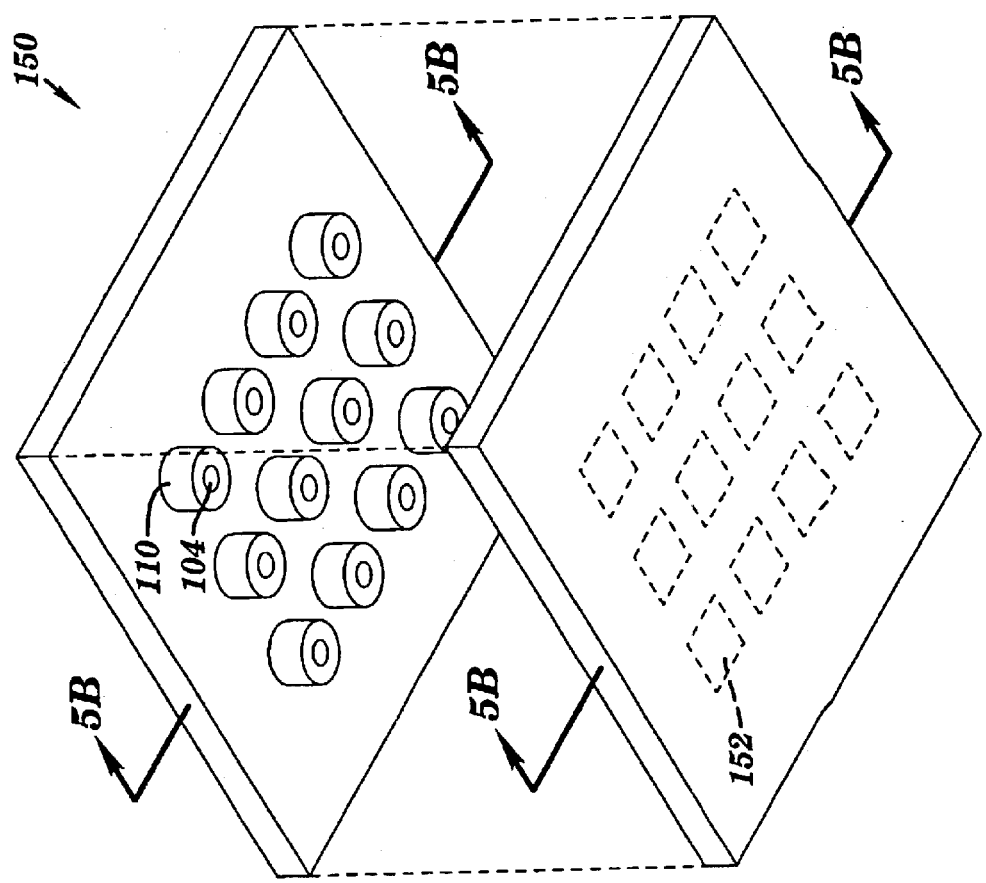
FIGS. 5A to 5B show a perspective view and a cross-sectional view, respectively, of a multiple array of electrospray devices in accordance with the present invention.
Figure 5B:
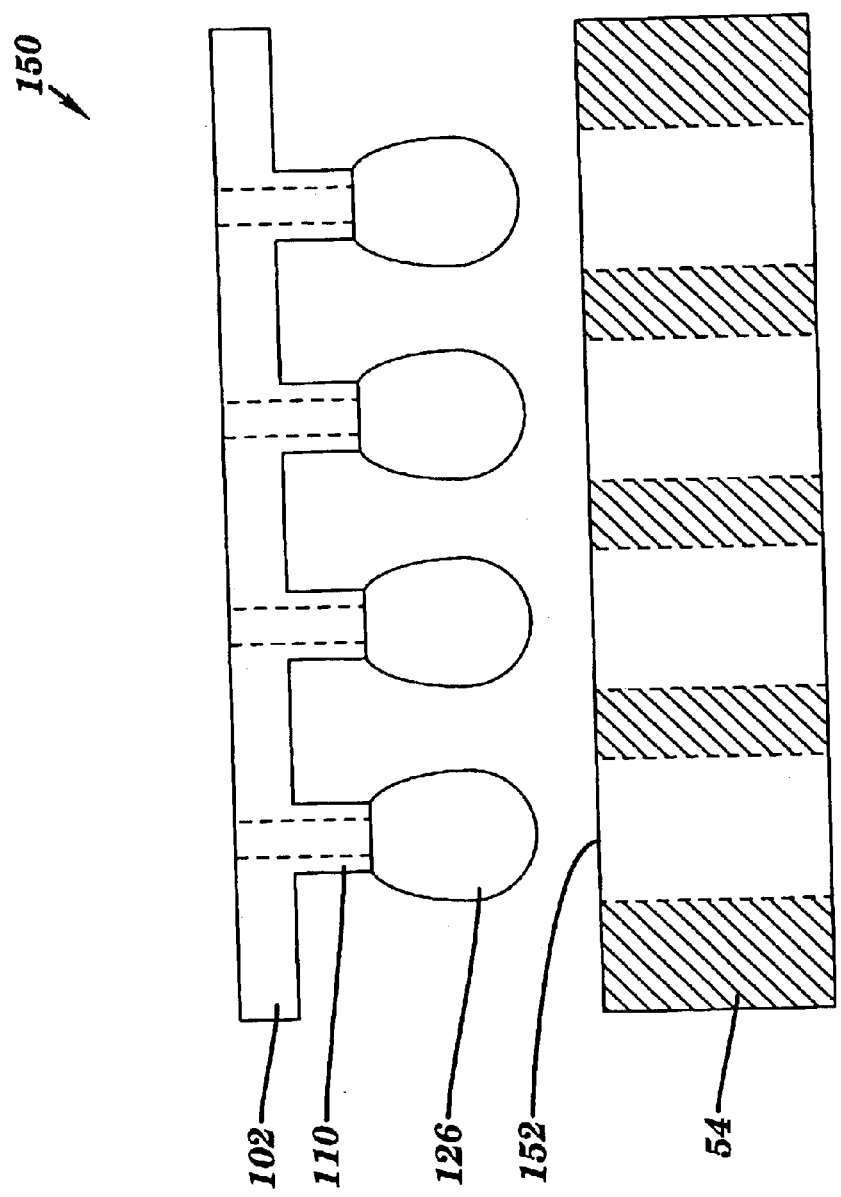

This aspect of the present invention does not have the space constraints of current piezoelectric dispensers. The nozzles (dispensers) may be positioned as close as 20 μm allowing for very high-density dispensing. For example, an array of 10,000 dispensing nozzles with a 20 μm outer diameter and a 50 μm pitch would have an area of 5 mm×5 mm. An array of 1,000,000 dispensing nozzles with a 20 μm outer diameter and a 50 μm pitch would have an area of 50 mm×50 mm (or two square inches). The number of dispensing nozzles in an array is only limited by the outer diameter of the nozzle size chosen and the required spacing for the application. FIG. 5A shows a perspective view of a 12-nozzle array aligned with an array of receiving wells 152. These receiving wells may be small volume reservoirs for performing chemical reactions for the purpose of chemical synthesis, for biological screening or may be through-substrate channels for transferring a fluid sample from one microchip device to another. FIG. 5B shows a cross-sectional view of FIG. 5A showing the array in a droplet dispensing mode and the receiving wells 152 depicted as through-substrate channels. Each nozzle 110 has a fluid droplet 126 being extracted by an electric field established between the fluid, substrate 102 and the receiving well plate 154.

The electrospray device may also serve to reproducibly distribute and deposit a sample from a mother plate to daughter plate(s) by nanoelectrospray deposition or by the droplet method. A chip-based combinatorial chemistry system comprising a reaction well block may define an array of reservoirs for containing the reaction-products from a combinatorially synthesized compound. The reaction well block further defines channels, nozzles and recessed portions such that the fluid in each reservoir may flow through a corresponding channel and exit through a corresponding nozzle in the form of droplets. The reaction well block may define any number of reservoir(s) in any desirable configuration, each reservoir being of a suitable dimension and shape. The volume of a reservoir may range from a few picoliters up to several microliters.

The reaction well block may serve as a mother plate to interface to a microchip-based chemical synthesis apparatus such that the droplet method of the electrospray device may be utilized to reproducibly distribute discreet quantities of the product solutions to a receiving or daughter plate. The daughter plate defines receiving wells that correspond to each of the reservoirs. The distributed product solutions in the daughter plate may then be utilized to screen the combinatorial chemical library against biological targets.

The electrospray device may also serve to reproducibly distribute and deposit an array of samples from a mother plate to daughter plates, for example, for proteomic screening of new drug candidates. This may be by either droplet formation or electrospray modes of operation. Electrospray device(s) may be etched into a microdevice capable of synthesizing combinatorial chemical libraries. At a desired time, a nozzle(s) may apportion a desired amount of a sample(s) or reagent(s) from a mother plate to a daughter plate(s). Control of the nozzle dimensions, applied voltages, and time provide a precise and reproducible method of sample apportionment or deposition from an array of nozzles, such as for the generation of sample plates for molecular weight determinations by matrix-assisted laser desorption/ionization time-of-flight mass spectrometry ("MALDI-TOFMS"). The capability of transferring analytes from a mother plate to daughter plates may also be utilized to make other daughter plates for other types of assays, such as proteomic screening. The $V_{fluid}/V_{substrate}$ ratio can be chosen for formation of an electrospray or droplet mode based on a particular application.

An array of electrospray devices can be configured to disperse ink for use in an ink jet printer. The control and enhancement of the electric field at the exit of the nozzles on a substrate will allow for a variation of ink apportionment schemes including the formation of submicometer, highly-charged droplets for blending of different colors of ink.

The electrospray device of the present invention can be integrated with miniaturized liquid sample handling devices for efficient electrospray of the liquid samples for detection using a mass spectrometer. The electrospray device may also be used to distribute and apportion fluid samples for use with high-throughput screen technology. The electrospray device may be chip-to-chip or wafer-to-wafer bonded to plastic, glass, or silicon microchip-based liquid separation devices capable of, for example, capillary electrophoresis, capillary electrochromatography, affinity chromatography, liquid chromatography ("LC"), or any other condensed-phase separation technique.

Figure 6A:
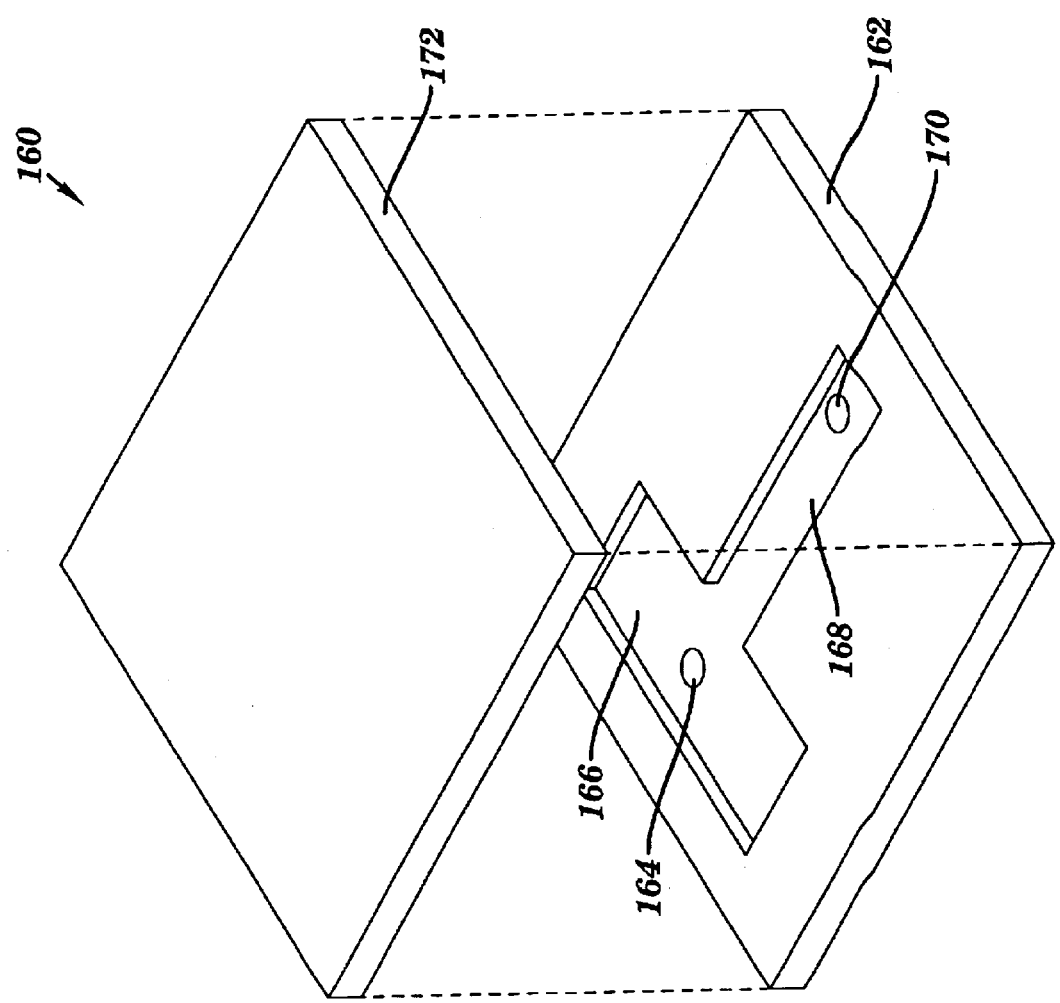
FIGS. 6A to 6B show perspective views of alternative embodiments of microchip-based liquid chromatography devices in accordance with the present invention.
Figure 6B:
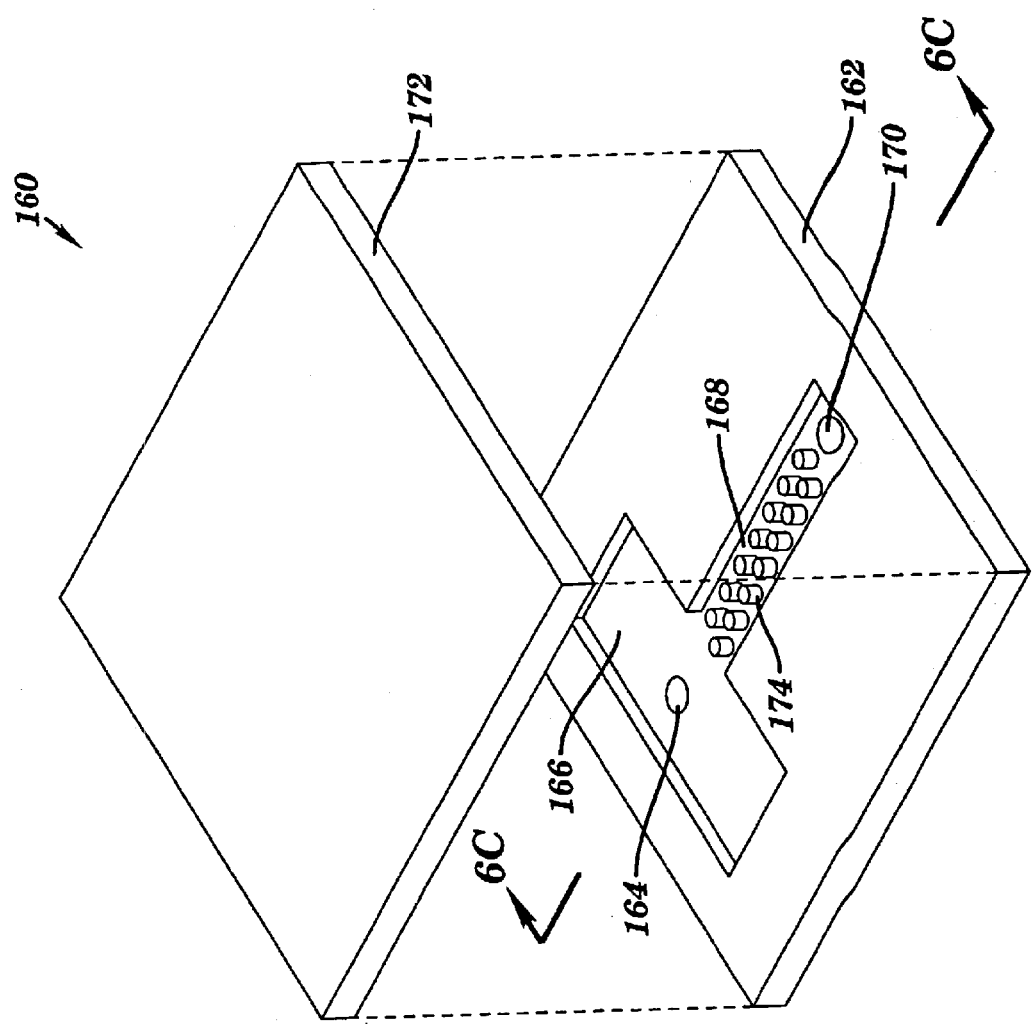

In another aspect of the invention, a microchip-based liquid chromatography device 160 may be provided as shown in FIG. 6A. The liquid chromatography device generally comprises a separation substrate 162 or wafer defining an introduction channel 164 between an entrance orifice and a reservoir 166 and a separation channel 168 between the reservoir and an exit orifice 170. A cover substrate 172 may be bonded to the separation substrate to enclose the reservoir and the separation channel adjacent to the cover substrate. The separation channel may be populated with separation posts 174 as shown in FIG. 6B extending from a side-wall of the separation channel perpendicular to the fluid flow through the separation channel. Preferably, the separation posts are coplanar or level with the surface of the separation substrate such that they are protected against accidental breakage during the manufacturing process. Component separation occurs in the separation channel where the separation posts perform the liquid chromatography function by providing a large surface area for the interaction of fluid flowing through the separation channel.

Figure 6C:
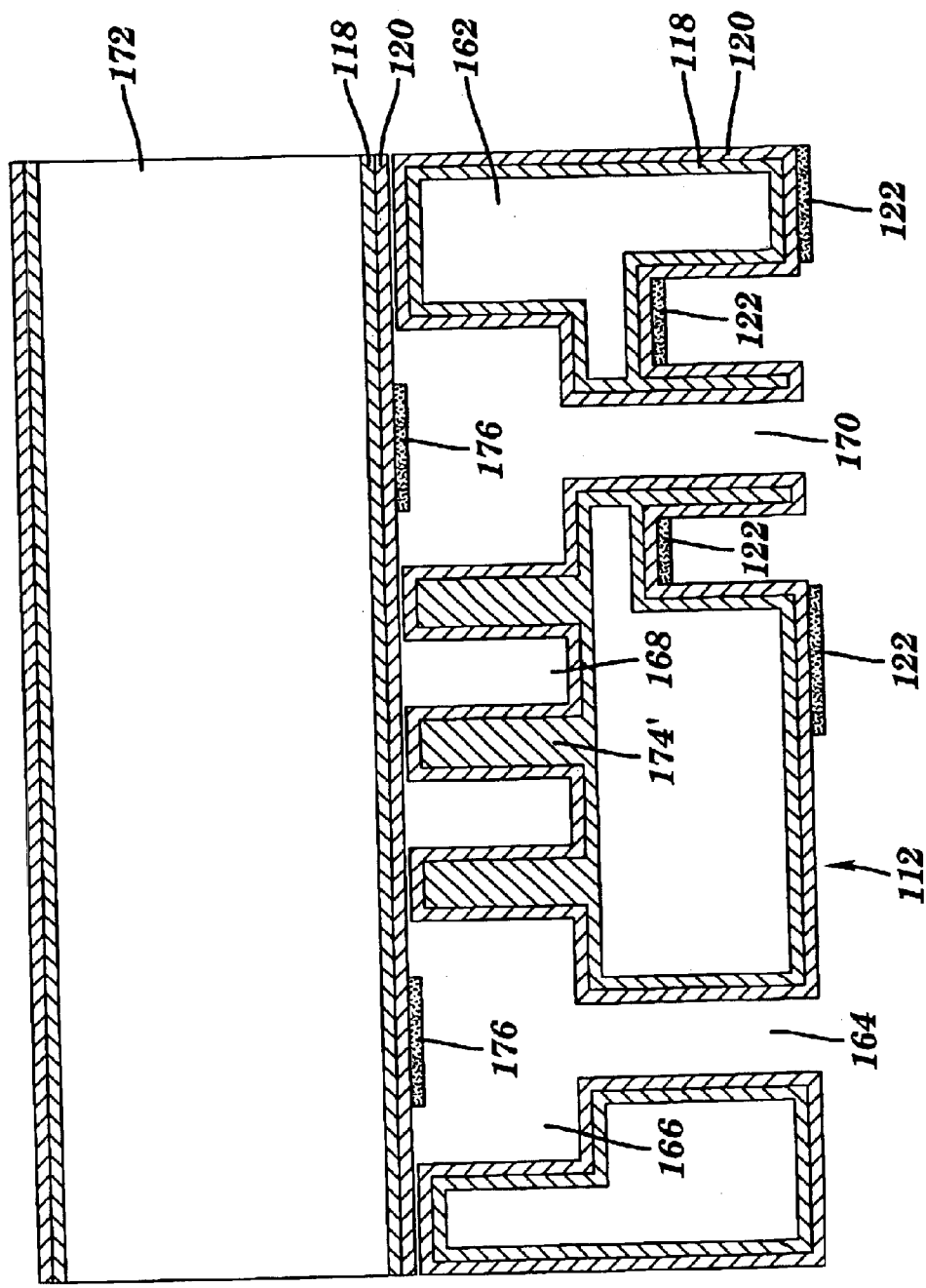
FIG. 6C is a cross-sectional view of the microchip-based liquid chromatography device of FIG. 6B taken along line 6C—6C.

The liquid chromatography device may be integrated with an electrospray device such that the exit orifice of the liquid chromatography device forms a homogenous interface with the entrance orifice of the electrospray device. This allows the on-chip delivery of fluid from the liquid chromatography device to the electrospray device to generate an electrospray. The nozzle, channel, and recessed portion of the electrospray device may be etched from the substrate of the liquid chromatography device. FIG. 6C is a cross-sectional view of FIG. 6B wherein the exit orifice 170 of the liquid chromatography device is the through-substrate channel 104 of an electrospray device. The liquid chromatography device may further comprise one or more electrodes 176 for application of electric potentials to the fluid at locations along the fluid path. The application of different electric potentials along the fluid path may facilitate the fluid flow through the fluid path using the electrophoretic properties of the fluid and chemical species contained therein. Also shown are the electrospray nozzle 110, recessed annular region 114, and the electrospray controlling electrodes 122 on the ejection surface 112 of the substrate.

The introduction 164 and separation 168 channels, the entrance and exit 170 orifices, and the separation posts 174 are preferably etched from a silicon substrate by reactive-ion etching and other standard semiconductor processing techniques. The separation posts are preferably oxidized silicon posts 174' to electrically insulate the posts and channel from the silicon substrate. A silicon dioxide layer 118 may be grown on all surfaces of the separation substrate 162. Silicon nitride 120 may be further deposited on the silicon dioxide to provide a moisture barrier and prevent diffusion of water and ions to the substrate. The surface of the silicon posts may be further chemically modified to form a stationary phase to optimize the interaction of the components of the sample fluid with the stationary separation posts.

Figure 7A:
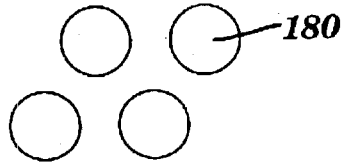
FIGS. 7A to 7F show different separation post spacings.
Figure 7B:
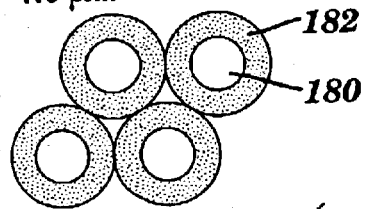
Figure 7D:
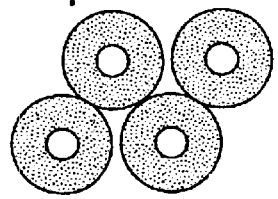
Figure 7C:
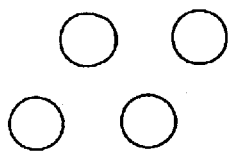
Figure 7E:
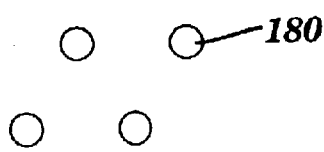
Figure 7F:
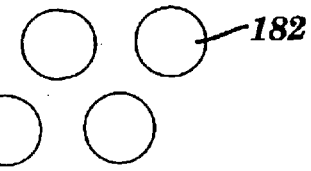

Photolithography and reactive-ion etching limit the layout design of separation post diameters and inter-post spacing to approximately 1 $\mu$m. However, because the thermal oxidation process consumes approximately 0.46 $\mu$m of silicon to form each micrometer of silicon dioxide, the thermal oxidation process results in a volumetric expansion. This volumetric expansion may be utilized to reduce the spacing between the separation posts to sub-micrometer dimensions as shown in FIG. 7. For example, if the final layout is a channel populated with 1 $\mu$m silicon dioxide posts separated by 0.5 $\mu$m, the following method may be used to generate such a device. If the layout begins with 1 $\mu$m silicon posts 180 spaced by 0.5 $\mu$m (FIG. 7A.), oxidizing the silicon posts using an elevated temperature, oxidizing furnace until the post diameters reached 1.5 $\mu$m would consume 0.12 $\mu$m of silicon (FIG. 7B.). The silicon dioxide 182 that was formed can be removed by placing the silicon substrate in a hydrofluoric acid solution. The hydrofluoric acid will selectively remove the silicon dioxide from the silicon substrate. The remaining silicon posts would now have a diameter of 0.77 $\mu$m (FIG. 7C.). If the silicon posts were oxidized to 1.44 $\mu$m diameter, 0.31 $\mu$m of silicon would be consumed (FIG. 7D.). Removal of the silicon dioxide would leave silicon posts of 0.46 $\mu$m diameter (FIG. 7E.). Complete oxidation of the 0.46 $\mu$m silicon posts 180 will result in the formation of 1 $\mu$m silicon dioxide posts 182 spaced by 0.5 $\mu$m (FIG. 7F.). Further, because the oxidation process is well-controlled, separation post dimensions, including the inter-post spacing, in the sub-micrometer regime can be formed reproducibly and in a high yielding manner.

Figure 8A:
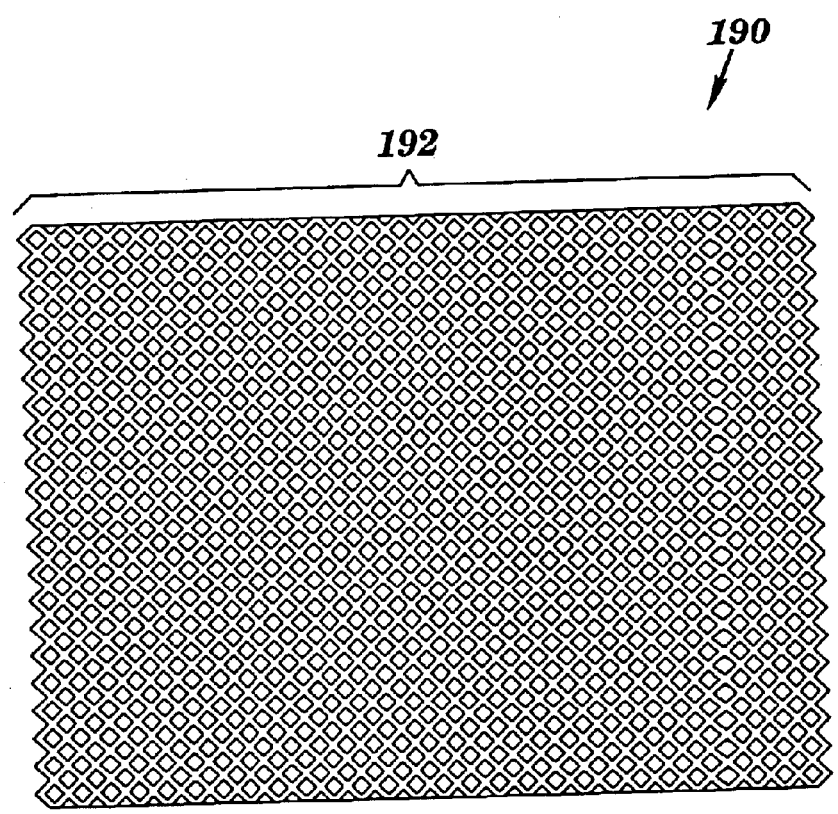
FIGS. 8A to 8B show plan views of a computer-aided layout of a channel containing spaced posts for use in a liquid chromatography device in accordance with the present invention.
Figure 8B:
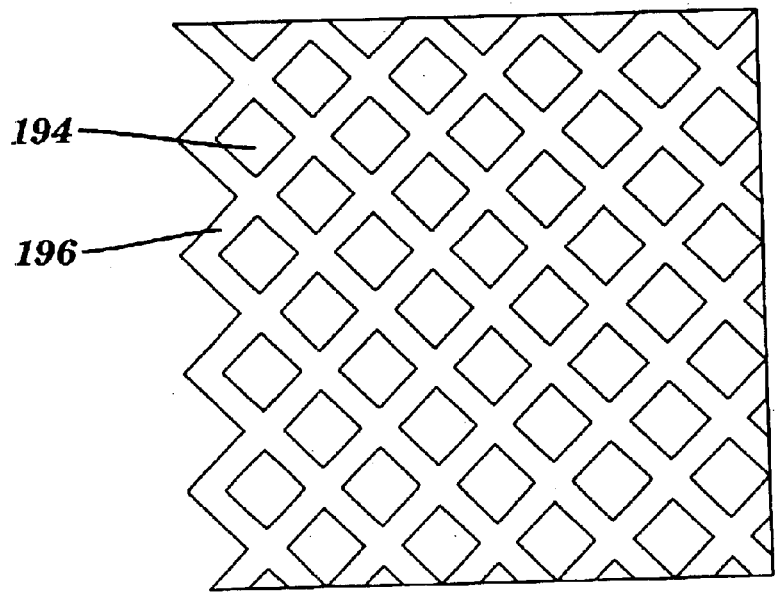

FIGS. 8A and 8B show plan views of a computer-aided design (CAD) layout 190 of a 50 $\mu$m wide channel 192 containing 1 $\mu$m silicon posts spaced by 0.5 $\mu$m. The black squares 194 represent unexposed areas of the channel while the gray 196 areas represent exposed areas of the channel. The exposed areas are removed during the silicon processing of the substrate, while the unexposed areas remain. The result of the processing is a channel etched to a depth of a few tens of micrometers containing 1 $\mu$m silicon posts spaced by 0.5 $\mu$m. The remaining silicon substrate can then be further oxidized in an oxidizing furnace to grow the silicon dioxide layer to any required thickness without affecting the completely oxidized silicon posts. Further processing of the silicon substrate such as LPCVD of silicon nitride and/or LPCVD or plasma enhanced chemical vapor deposition ("PECVD") of silicon dioxide is possible.

An array or matrix of multiple electrospray devices of the present invention may be manufactured on a single microchip as silicon fabrication using standard, well-controlled thin-film processes. This not only eliminates handling of such micro components but also allows for rapid parallel processing of functionally alike elements. The nozzles may be radially positioned, for example, about a circle having a relatively small diameter near the center of the chip. Thus, a 96 radial array of electrospray devices of the present invention may be positioned in front of an electrospray mass spectrometer with no requirement to move or reposition the microchip. This radial design provides significant advantages of time and cost efficiency, control, and reproducibility when analyzing multiple channels by electrospray mass spectrometry. The low cost of these electrospray devices allows for one-time use such that cross-contamination from different liquid samples may be eliminated.

The requirement to minimize the variations in the cross-sectional area along the length of a separation channel also applies when combining a separation device with an electrospray device. The cross-sectional area for the inner diameter of the nozzle, $\text{Nozzle}_{Area}^2$, of an electrospray device should be approximately the same as the channel cross-sectional area, $\text{Channel}_{Area}^2$. In practice, a $\text{Nozzle}_{Area}^2 / \text{Channel}_{Area}^2$ ratio less than 2 is desirable. The cross-sectional area of a separation device can be determined by calculating the percentage of cross-sectional area for a post and the separation from an adjacent post. The cross-sectional area for a given channel can then be calculated from the following equation:

$$Channel_{Area^2} = \qquad (4)$$
$$Width_{Ch} * Depth_{Ch}(1 - (Dia_{post}/(Diam_{post} + Spacing_{post})))$$

where $\text{Width}_{Ch}$ is the separation channel width, $\text{Depth}_{Ch}$ is the separation channel depth, $\text{Dia}_{post}$ is the post diameter and $\text{Spacing}_{post}$ is the post spacing. Setting the cross-sectional area of the electrospray nozzle equal to the cross-sectional area of the separation channel allows the calculation for the optimum inner diameter for the electrospray device for a particular separation channel layout. The cross-sectional area for a cylindrical nozzle, $\text{Nozzle}_{Area}^2$, is defined by equation 5:

$$Nozzle_{Area^2} = \pi r^2 = \pi (d/2)^2 \qquad (5)$$

where r is the inner radius and d is the inner diameter of the nozzle.

Setting the $\text{Nozzle}_{Area}^2$ equal to the $\text{Channel}_{Area}^2$ allows the determination of the optimum nozzle inner diameter, $\text{Nozzle}_{Inner\_Dia}$, for a given channel cross-sectional area from equation 6:

$$Nozzle_{InnerDia} = 2 * \sqrt{\frac{Channel_{Area^2}}{\pi}} \qquad (6)$$

Table 1 lists some examples of the optimum nozzle inner diameter for some examples of posts diameters and spacings for a 50 $\mu$m wide by 10 $\mu$m deep channel.

TABLE 1

Relationship between a 50 μm width by 10 μm depth channel populated with posts and the optimum electrospray nozzle inner diameter

| Post Diameter, μm | Post Spacing, μm | Channel and Nozzle Cross-sectional Areas, μm$^2$ | Electrospray Nozzle Inner Diameter μm |
|---|---|---|---|
| 1 | 0.1 | 45 | 7.6 |
| 1 | 0.2 | 83 | 10.3 |
| 1 | 0.3 | 115 | 12.1 |
| 1 | 0.4 | 143 | 13.5 |
| 1 | 0.5 | 167 | 14.6 |
| 1 | 0.8 | 222 | 16.8 |
| 1 | 1 | 250 | 17.8 |
| 1 | 1.5 | 300 | 19.5 |
| 2 | 0.1 | 24 | 5.5 |
| 2 | 0.2 | 45 | 7.6 |
| 2 | 0.3 | 65 | 9.1 |
| 2 | 0.4 | 83 | 10.3 |
| 2 | 0.5 | 100 | 11.3 |
| 2 | 0.8 | 143 | 13.5 |
| 2 | 1 | 167 | 14.6 |
| 2 | 1.5 | 214 | 16.5 |

In yet another aspect of the present invention, multiples of the liquid chromatography-electrospray system may be formed on a single chip to deliver a multiplicity of samples to a common point for subsequent sequential analysis. The multiple nozzels of the electrospray devices may be radially positioned about a circle having a relatively small diameter near the center of the single chip.

A radially distributed array of electrospray nozzles on a multi-system chip may be interfaced with an ion-sampling orifice of an electrospray mass spectrometer by positioning the nozzles near the ion-sampling orifice. A tight radial configuration of the electrospray nozzles allows the positioning thereof in close proximity to the ion-sampling orifice of an electrospray mass spectrometer. For example, 96 20 μm nozzles may be etched around a 1 mm radius circle with a separation of 65 μm.

A multi-system chip thus provides a rapid sequential chemical analysis system fabricated using microelectromechanical systems ("MEMS") technology. For example, the multi-system chip enables automated, sequential separation and injection of a multiplicity of samples, resulting in significantly greater analysis throughput and utilization of the mass spectrometer instrument for, for example, high-throughput detection of compounds for drug discovery.

Another aspect of the present invention provides a silicon microchip-based electrospray device for producing electrospray of a liquid sample. The electrospray device may be interfaced downstream to an atmospheric pressure ionization mass spectrometer ("API-MS") for analysis of the electrosprayed fluid. Another aspect of the invention is an integrated miniaturized liquid phase separation device, which may have, for example, glass, plastic or silicon substrates integral with the electrospray device.

Electrospray Device Fabrication Procedure

The electrospray device 100 is preferably fabricated as a monolithic silicon substrate utilizing well-established, controlled thin-film silicon processing techniques such as thermal oxidation, photolithography, reactive-ion etching (RIE), chemical vapor deposition, ion implantation, and metal deposition. Fabrication using such silicon processing techniques facilitates massively parallel processing of similar devices, is time- and cost-efficient, allows for tighter control of critical dimensions, is easily reproducible, and results in a wholly integral device, thereby eliminating any assembly requirements. Further, the fabrication sequence may be easily extended to create physical aspects or features on the injection surface and/or ejection surface of the electrospray device to facilitate interfacing and connection to a fluid delivery system or to facilitate integration with a fluid delivery sub-system to create a single integrated system.

Injection Surface Processing: Entrance to Through-Wafer Channel

FIGS. 9A–9E illustrate the processing steps for the injection side of the substrate in fabricating the electrospray device of the present invention. Referring to the plan and cross-sectional views, respectively, of FIGS. 9A and 9B (a cross-sectional view taken along line 9B—9B of FIG. 9A), a double-side polished silicon wafer 200 is subjected to an elevated temperature in an oxidizing environment to grow a layer or film of silicon dioxide 204 on the injection side 203 and a layer or film of silicon dioxide 206 on the ejection side 205 of the substrate 202. Each of the resulting silicon dioxide layers 204, 206 has a thickness of approximately 1–2 μm. The silicon dioxide layers 204, 206 serve as masks for subsequent selective etching of certain areas of the silicon substrate 202. The silicon dioxide layer 206 also serves as an etch stop for the through-substrate channel etch as described below.

A film of positive-working photoresist 208 is deposited on the silicon dioxide layer 204 on the injection side 203 of the substrate 200. An area of the photoresist 208 corresponding to the entrance to a through-wafer channel which will be subsequently etched is selectively exposed through a mask by an optical lithographic exposure tool passing short-wavelength light, such as blue or near-ultraviolet at wavelengths of 365, 405, or 436 nanometers.

Figure 9A:
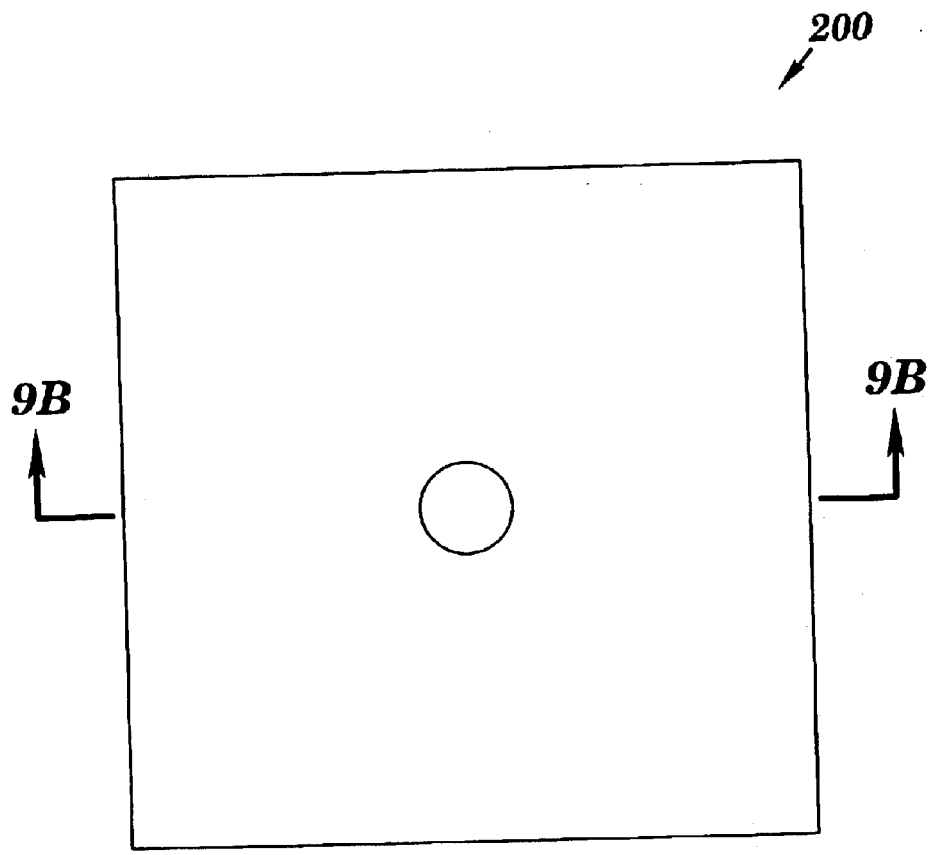
FIGS. 9A–9E show one embodiment of a fabrication sequence for the injection side of an electrospray device.
Figure 9B:
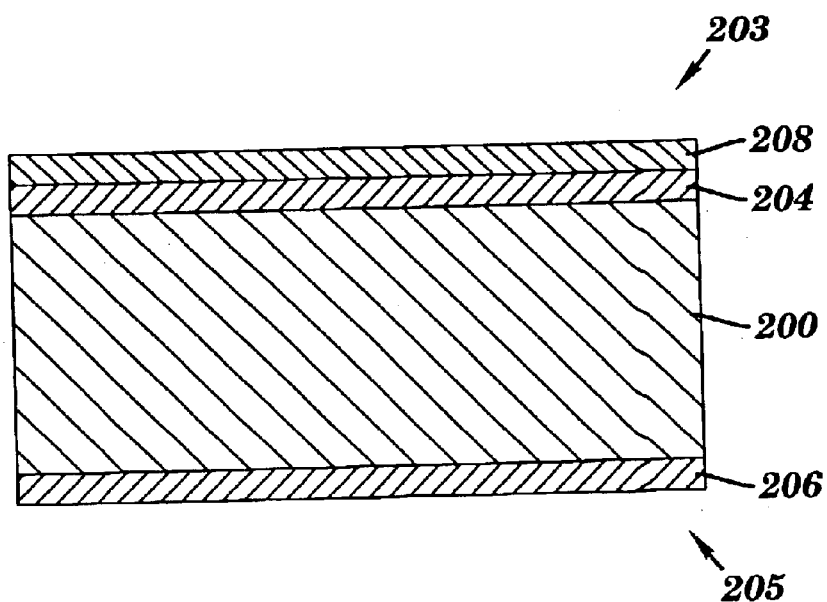
Figure 9C:
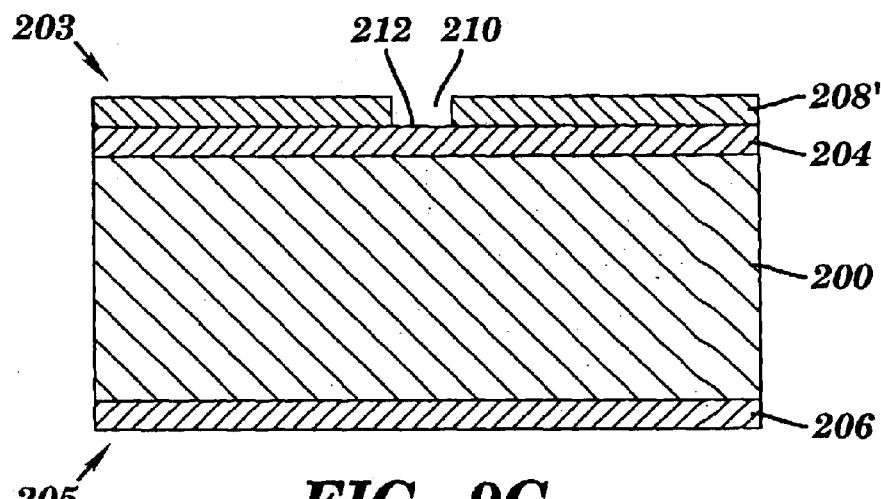
Figure 9D:
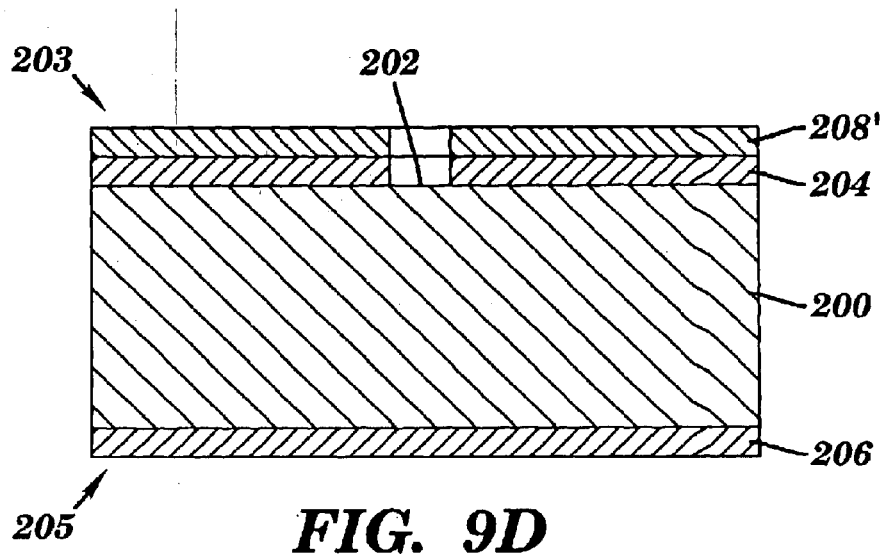

As shown in the cross-sectional views of FIGS. 9C and 9D, after development of the photoresist 208, the exposed area 210 of the photoresist is removed and open to the underlying silicon dioxide layer 204, while the unexposed areas remain protected by photoresist 208'. The exposed area 212 of the silicon dioxide layer 204 is then etched by a fluorine-based plasma with a high degree of anisotropy and selectivity to the protective photoresist 208' until the silicon substrate 202 is reached. As shown in the cross-sectional view of FIG. 9D, the remaining photoresist 208' provides additional masking during a subsequent fluorine based silicon etch to vertically etch certain patterns into the injection side 203 of the silicon substrate 200.

Figure 9E:
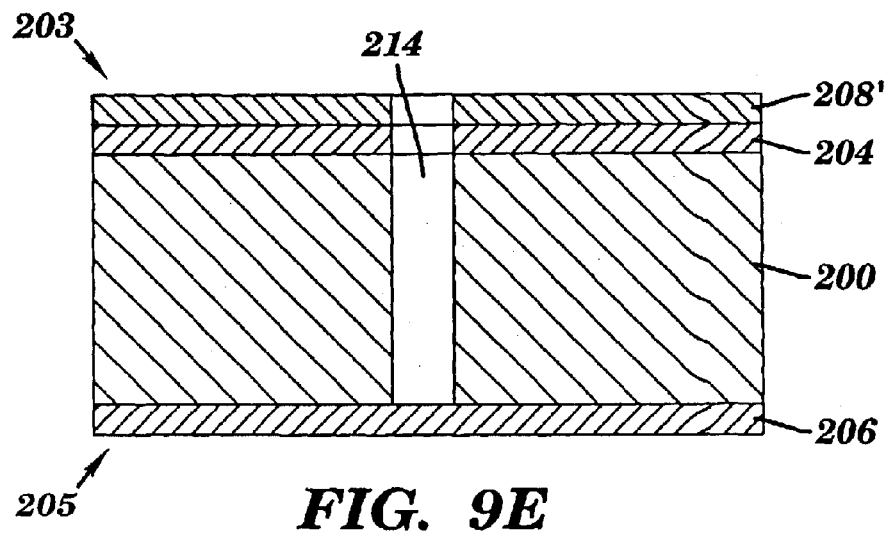

As shown in the cross-sectional view of FIG. 9E, the through-substrate channel 214 in the silicon substrate is vertically etched by another fluorine-based etch. An advantage of the fabrication process described herein is that the dimensions of the through channel, such as the aspect ratio (i.e. depth to width), can be reliably and reproducibly limited and controlled. The through-substrate channel is selectively etched through the silicon substrate until the silicon dioxide layer on the ejection surface is reached.

The through-substrate channel is used to align the ejection surface structures with the injection surface through-wafer channels. The through-substrate channel is etched through the substrate to the silicon dioxide layer 206 on the ejection side 205 of the substrate 200. This silicon dioxide layer 206 on the ejection surface serves as an etch stop for the injection surface processing. Silicon dioxide is transparent to visible light which allows the alignment of the injection side etch with the ejection side mask. This alignment scheme allows for alignment of injection and ejection side features to within 1 μm. The silicon dioxide layer on the ejection surface is still intact and provides for easy coating of resist on the ejection side for the subsequent ejection surface processing.

Ejection Surface Processing: Nozzle and Surrounding Surface Structure

FIGS. 10A–10F illustrate the processing steps for the ejection side 205 of the substrate 202 in fabricating the electrospray device 100 of the present invention. As shown in the cross-sectional view in FIG. 10B (a cross-sectional view taken along line 10B—10B of FIG. 10A), a film of positive-working photoresist 216 is deposited on the silicon dioxide layer 206 on the ejection side 205 of the substrate 202. Patterns on the ejection side 205 are aligned to those previously formed on the injection side 203 of the substrate 202 using a through-substrate alignment mark.

Figure 10A:
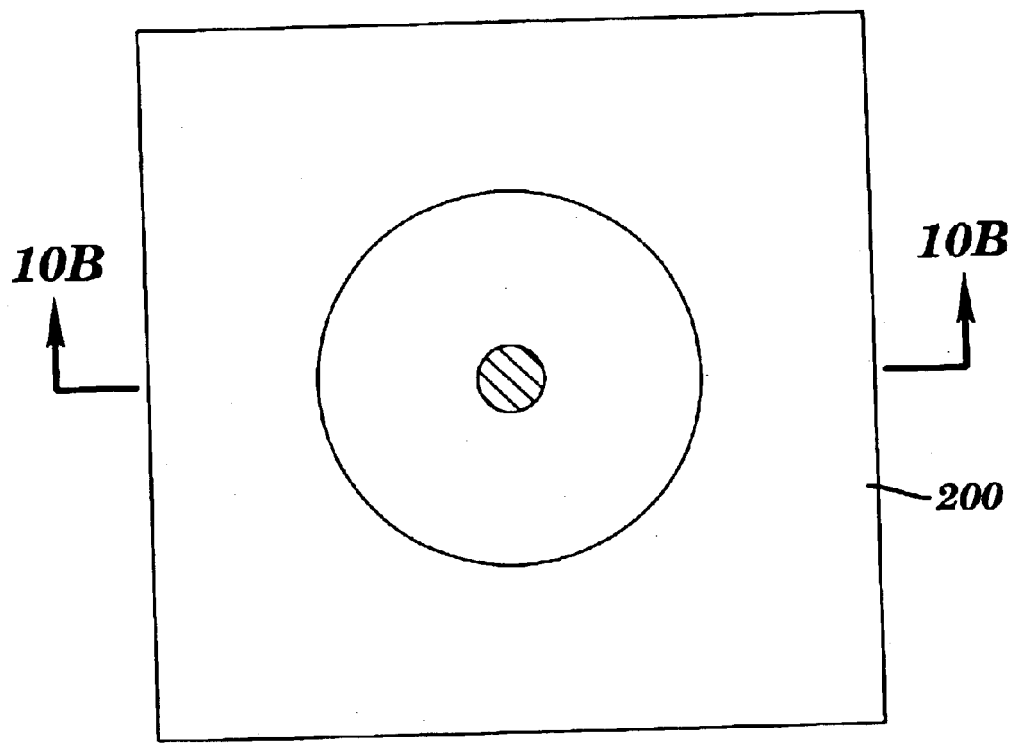
FIGS. 10A–10F show another embodiment of a fabrication sequence for the ejection side of an electrospray device.
Figure 10B:
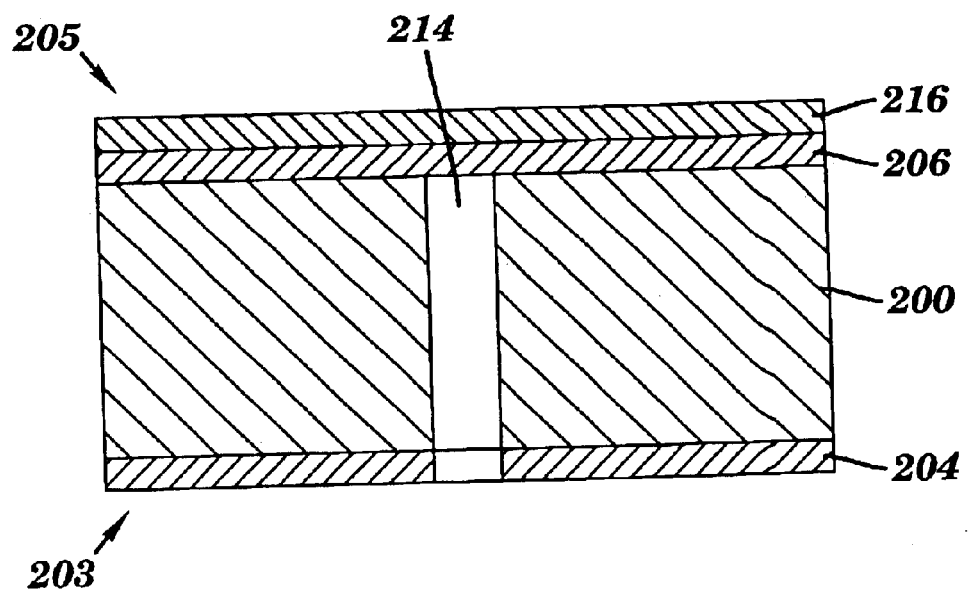
Figure 10C:
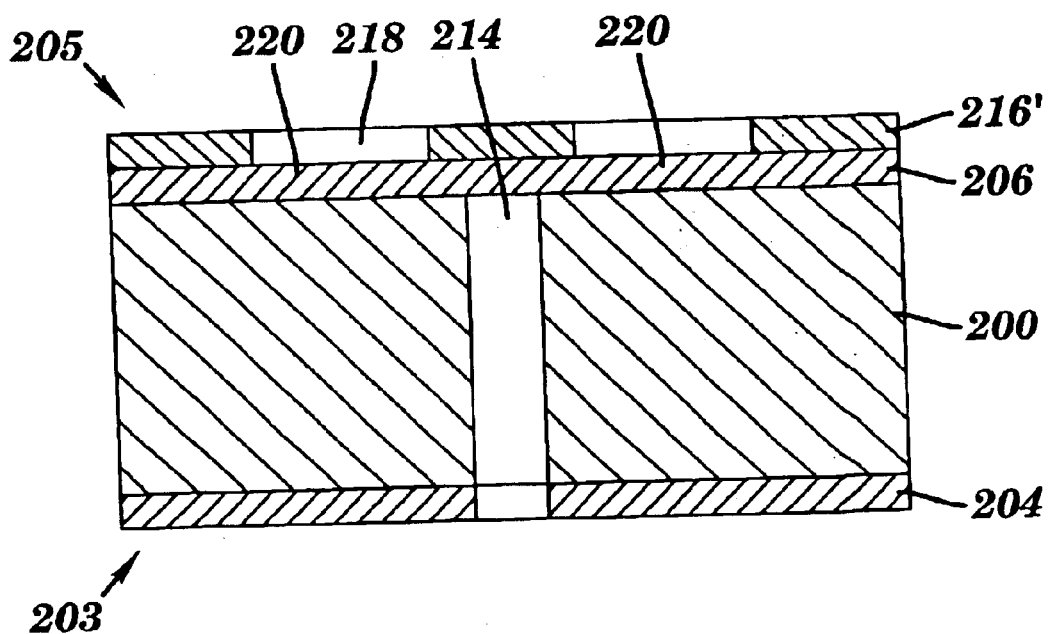
Figure 10D:
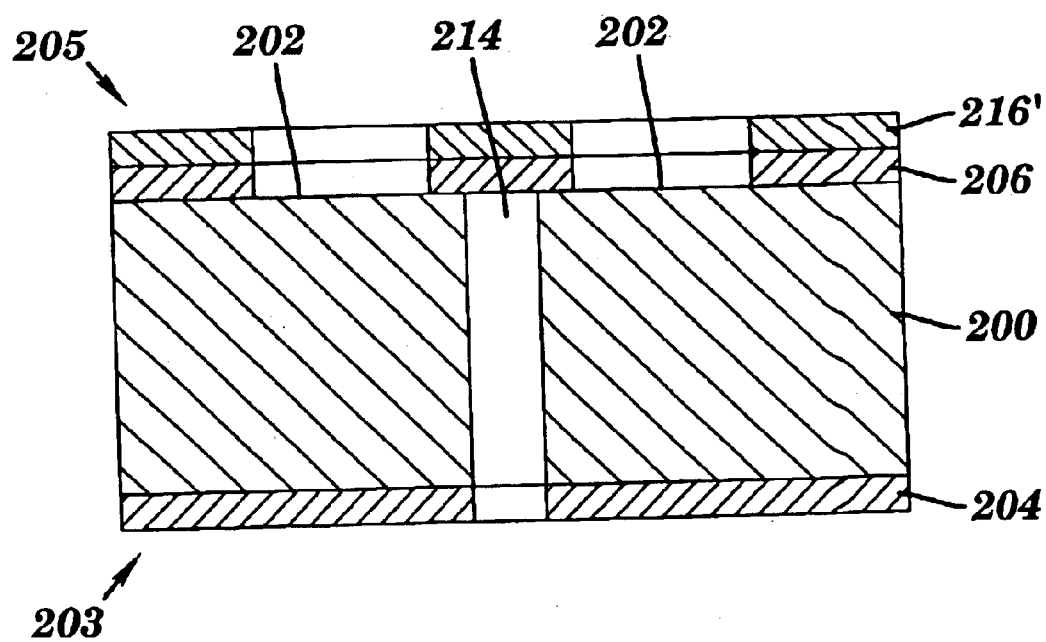

After alignment, areas of the photoresist 216 that define the outer diameter of the nozzle and the outer diameter of the recessed annular region are selectively exposed through an ejection side mask by an optical lithographic exposure tool passing short-wavelength light, such as blue or near-ultraviolet at wavelengths of 365, 405, or 436 nanometers. As shown in the cross-sectional view of FIG. 10C, the photoresist 216 is then developed to remove the exposed areas of the photoresist 218 such that the recessed annular region is open to the underlying silicon dioxide layer 220, while the unexposed areas remain protected by photoresist 216'. The exposed area 220 of the silicon dioxide layer 206 is then etched by a fluorine-based plasma with a high degree of anisotropy and selectivity to the protective photoresist 216' until the silicon substrate 202 is reached as shown in FIG. 10D.

Figure 10E:
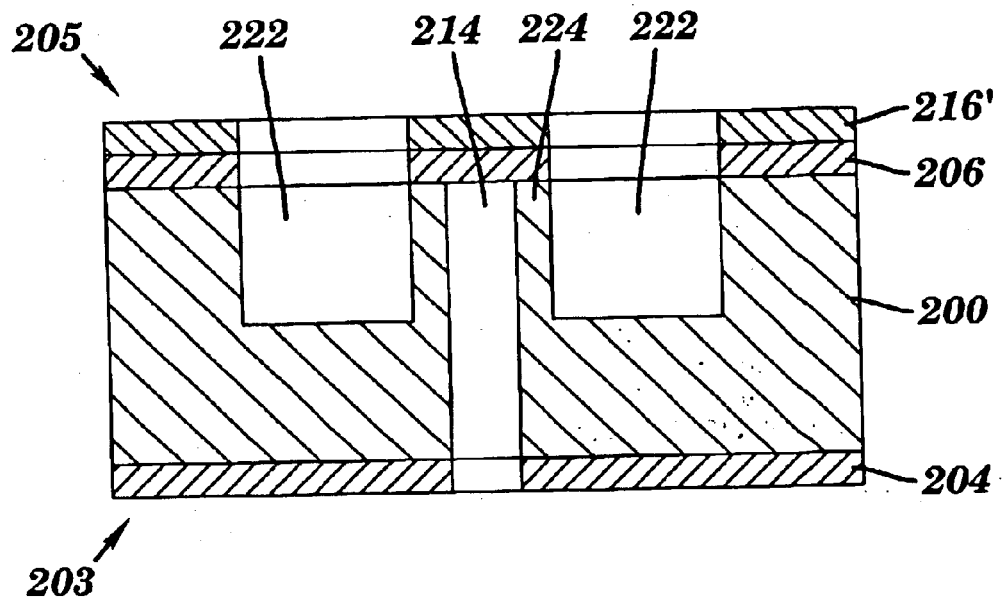
Figure 10F:
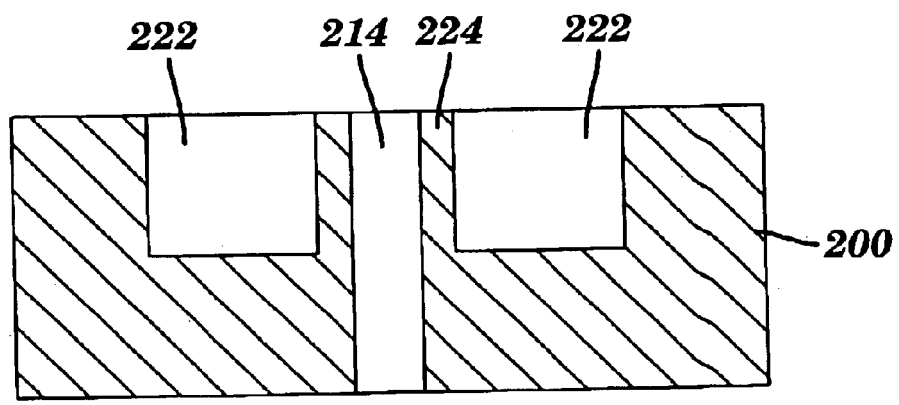

As shown in FIG. 10E, a fluorine-based etch creates a recessed annular region 222 that defines an ejection nozzle 224. After the desired depth is achieved for defining the recessed annular region 222 and nozzle 224, the remaining photoresist 216' is then removed in an oxygen plasma or in an actively oxidizing chemical bath like sulfuric acid ($H_2SO_4$) activated with hydrogen peroxide ($H_2O_2$). Then, the silicon dioxide layer 206 is removed using hydrofluoric acid to open up the through-substrate channel 214 as shown in FIG. 10F.

The fabrication method confers superior mechanical stability to the fabricated electrospray device by etching the features of the electrospray device from a monocrystalline silicon substrate without any need for assembly. The alignment scheme allows for nozzle walls of less than 2 $\mu$m and nozzle outer diameters down to 5 $\mu$m to be fabricated reproducibly. The fabrication sequence allows for the control of the nozzle height by adjusting the relative amounts of ejection side silicon etching. Further, the lateral extent and shape of the recessed annular region can be controlled independently of its depth. The depth of the recessed annular region also determines the nozzle height and is determined by the extent of the etch on the ejection side of the substrate. Control of the lateral extent and shape of the recessed annular region provides the ability to modify and control the electric field between the electrospray device and an extracting electrode.

Alternatively, the fabrication of the electrospray device may be accomplished whereby the through-substrate channel is etched partly from each side of the substrate in two steps in combination with a through-substrate alignment mark as shown in FIGS. 11A to B and 12A–E.

Injection Surface Processing: Entrance to Through-Wafer Channel

FIGS. 11A–11D illustrate the processing steps for the injection side of the substrate in fabricating the electrospray device of the present invention. Referring to the plan and cross-sectional views, respectively, of FIGS. 11A and 11B (taken along line 11B—11B of FIG. 11B), a double-side polished silicon substrate 200 is subjected to an elevated temperature in an oxidizing environment to grow a layer or film of silicon dioxide 204 on the injection side 203 and a layer or film of silicon dioxide 206 on the ejection side 205 of the substrate 200. Each of the resulting silicon dioxide layers 204 and 206 has a thickness of approximately 1–2 $\mu$m. The silicon dioxide layers 204 and 206 serve as masks for subsequent selective etching of certain areas of the silicon substrate. The silicon dioxide layer 206 also serves as an etch stop for the through-substrate alignment feature as described below.

Figure 11A:
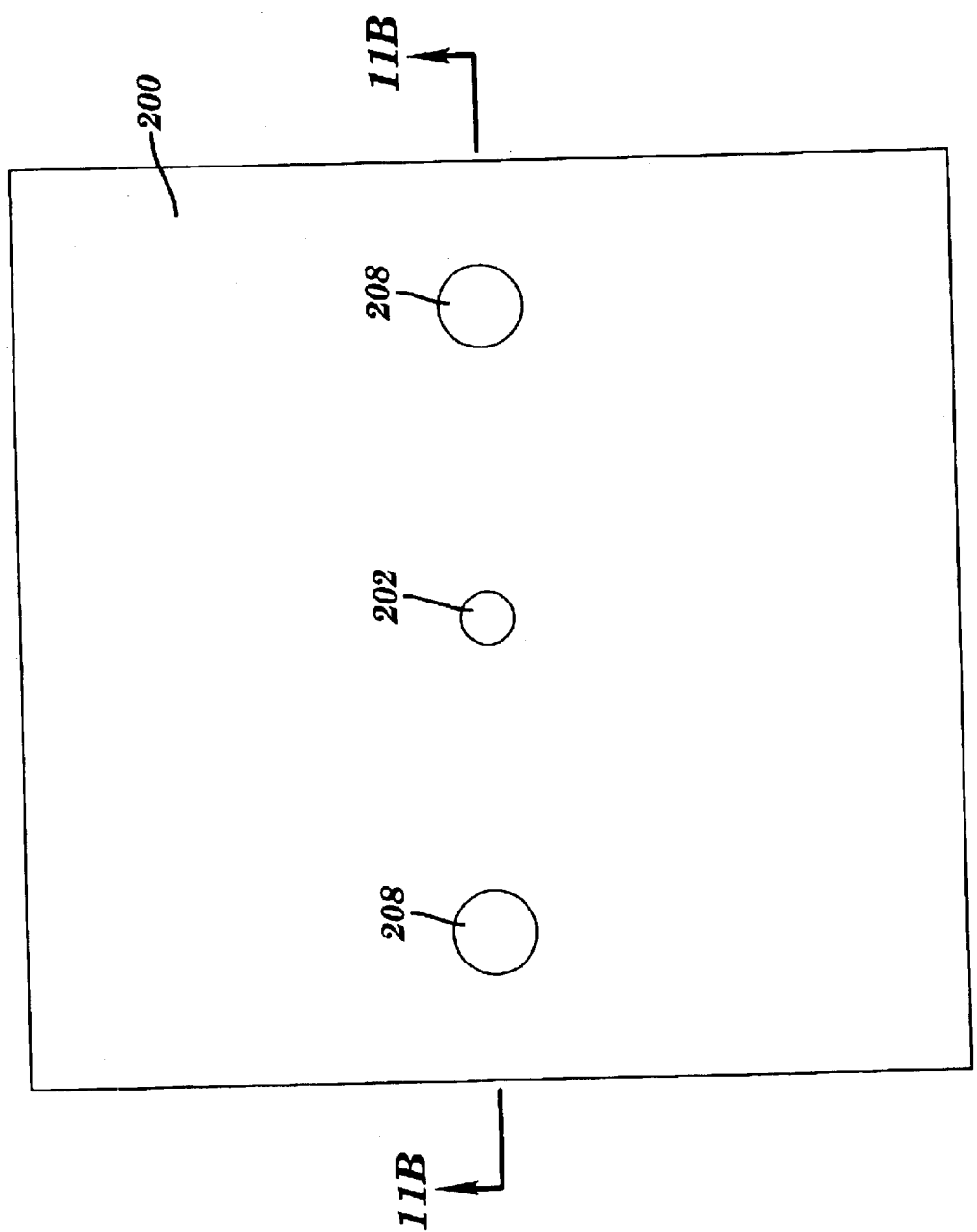
FIGS. 11A–11D show another embodiment of a fabrication sequence of the injection side of an electrospray device wherein a separate through-substrate alignment channel is incorporated into the device layout.
Figure 11B:
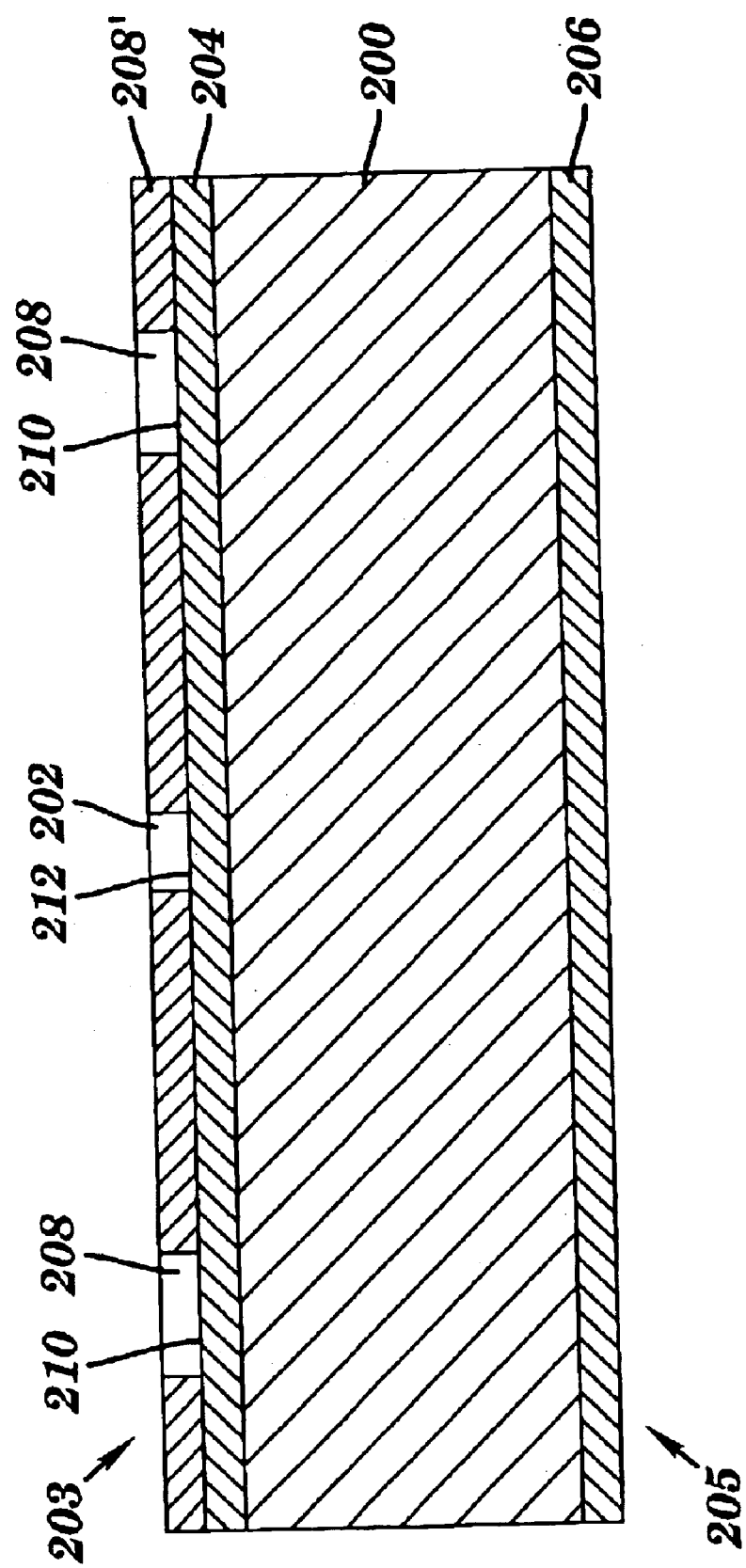
Figure 11C:
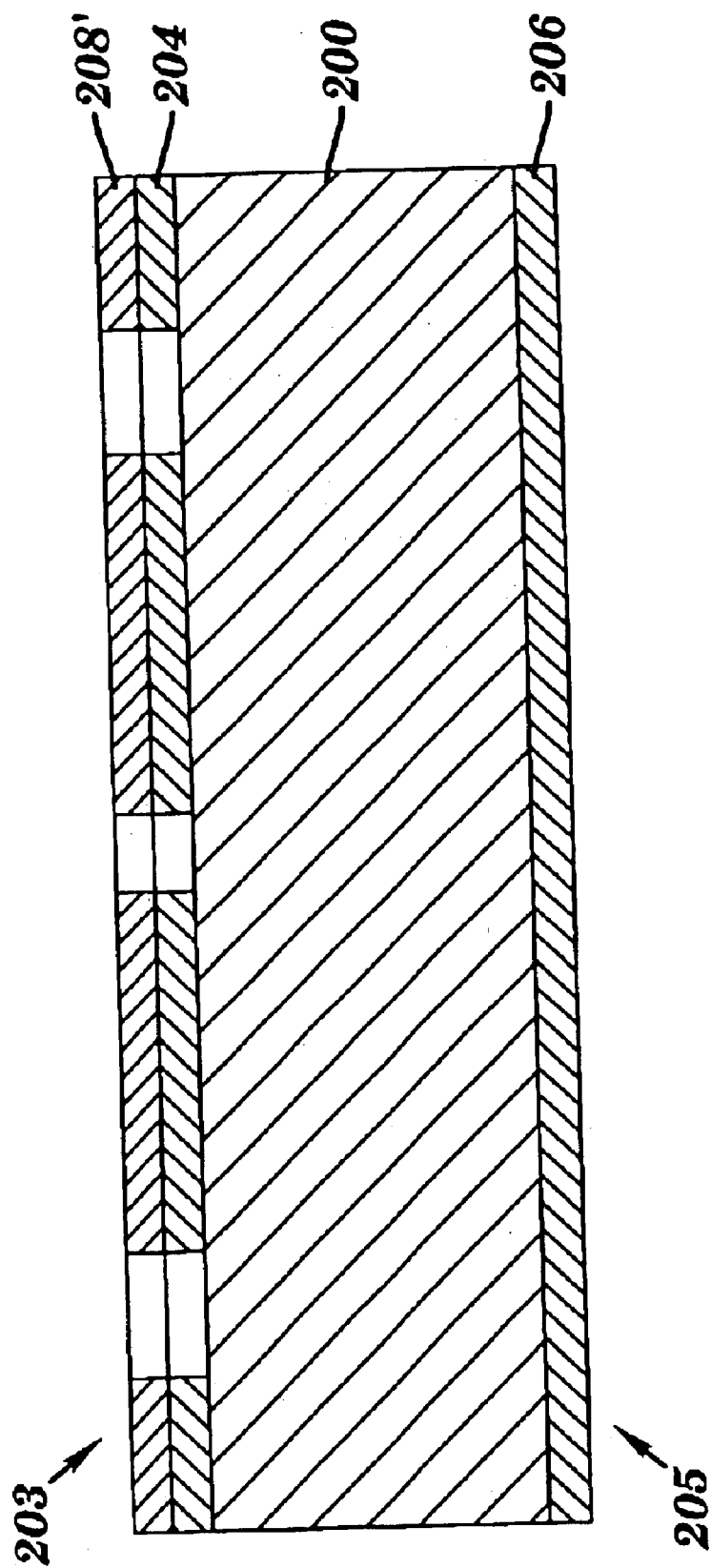

A film of positive-working photoresist 208' is deposited on the silicon dioxide layer 204 on the injection side 203 of the substrate 200. An area of the photoresist corresponding to the through wafer alignment 208 and the device channels 202 which will be subsequently etched is selectively exposed through a mask by an optical lithographic exposure tool passing short-wavelength light, such as blue or near-ultraviolet at wavelengths of 365, 405, or 436 nanometers. After development of the photoresist 208', the exposed area of the photoresist is removed and the underlying silicon dioxide layer of the alignment 210 and device 212 channels is exposed. The unexposed areas remain protected by the unexposed photoresist 208'. As shown in FIG. 11C the exposed area 212 of the silicon dioxide layer 204 is then etched by a fluorine-based plasma with a high degree of anisotropy and selectivity to the protective photoresist 208' until the silicon substrate 200 is reached. The remaining photoresist 208' provides additional masking during a subsequent fluorine based silicon etch to vertically etch certain patterns into the injection side 203 of the silicon substrate 204.

Figure 11D:
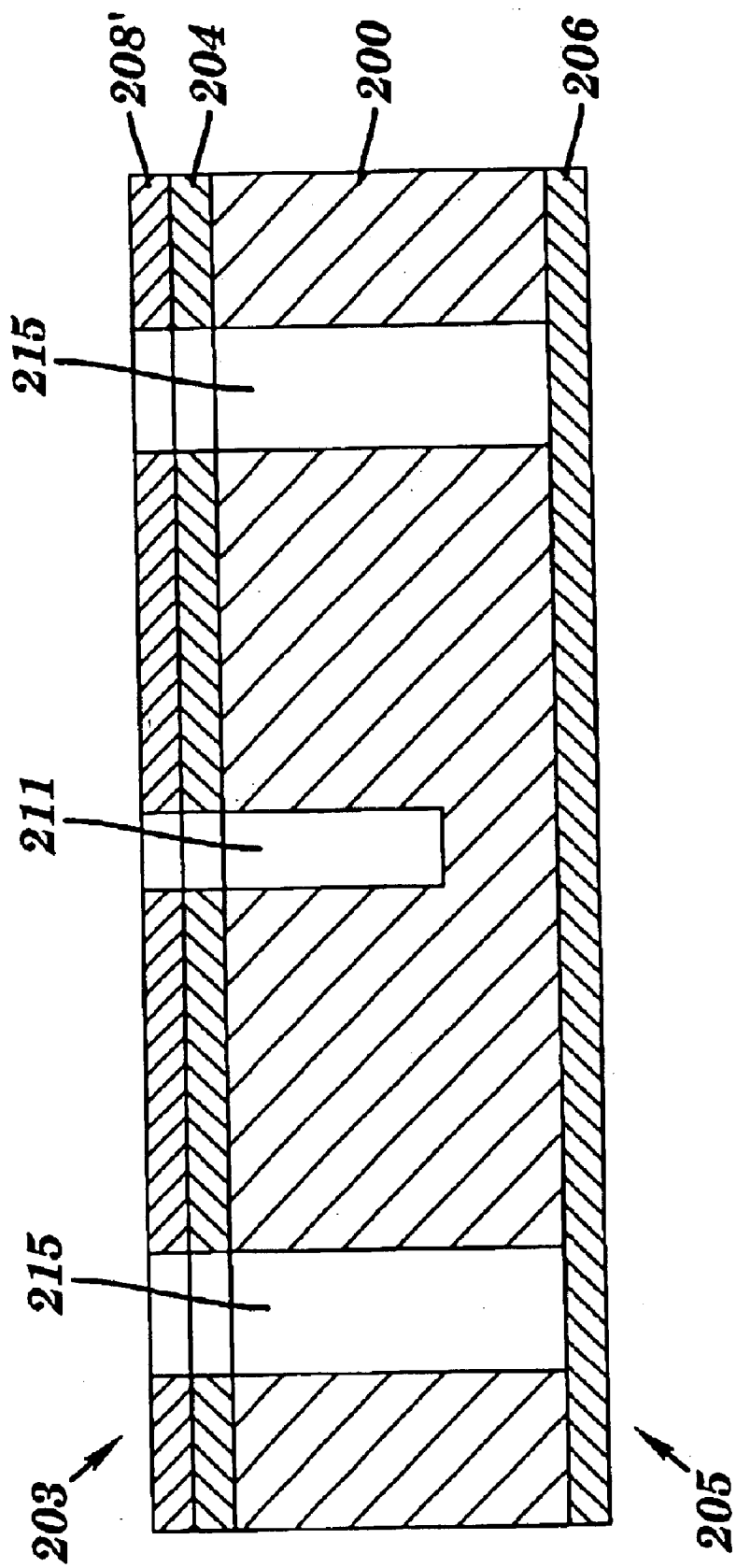

As shown in the cross-sectional view of FIG. 11D, the through-substrate alignment channel 215 and injection side channel 211 in the silicon substrate 200 is vertically etched by another fluorine-based etch. An advantage of the fabrication process described herein is that the dimensions of the features to be etched in silicon, such as the aspect ratio (depth to width), can be reliably and reproducibly limited and controlled. The fluorine-based etch rate is dependent on the feature dimensions being etched. Therefore, larger features etch more quickly through a substrate than smaller features. For the process described here, the through-substrate alignment mark 215 may be slightly larger in size (diameter) than the injection side channel 211. Therefore, the larger diameter through-substrate alignment channel 215 etches more quickly through the substrate 202 than the injection side channel 211. The through-substrate alignment marks are selectively etched completely through the silicon substrate 202 until the silicon dioxide layer 206, serving as an etch stop on the ejection surface 205, is reached. However, the smaller diameter injection side channel 211 is only etched partially through the wafer. Typically, the through-substrate alignment mark may be equivalent in diameter to up to tens of microns larger than the final through-substrate channel 214 to provide the required alignment tolerances.

The through-substrate alignment mark, consisting of for example, a 25 $\mu$m diameter circle, is incorporated in the channel mask. The through-substrate alignment mark is etched through the substrate to the silicon dioxide layer on the ejection side of the substrate. This silicon dioxide layer on the ejection surface serves as an etch stop for the injection surface processing. Silicon dioxide is transparent to visible light which allows the alignment mark from the injection side etch to be aligned with the ejection side mask. This alignment scheme allows for alignment of injection and ejection side features to within 1 μm. The silicon dioxide layer on the ejection surface is still intact and provides for easy coating of resist on the ejection side for the subsequent ejection surface processing.

Ejection Surface Processing: Nozzle and Surrounding Surface Structure

FIGS. 12A–E illustrate the processing steps for the ejection side 205 of the substrate in fabricating the electrospray device 100 of the present invention. Referring to the plan and cross-sectional views, respectively, of FIGS. 12A and 12B (taken along line 12B—12B of FIG. 12A), a film of positive-working photoresist is deposited on the silicon dioxide layer 206 on the ejection side 205 of the substrate 202. Patterns that define the inner and outer diameter of the nozzle and the outer diameter of the recessed annular region on the ejection side 205 are aligned to those previously formed on the injection side 203 of the substrate using the through-substrate alignment channels 215.

Figure 12A:
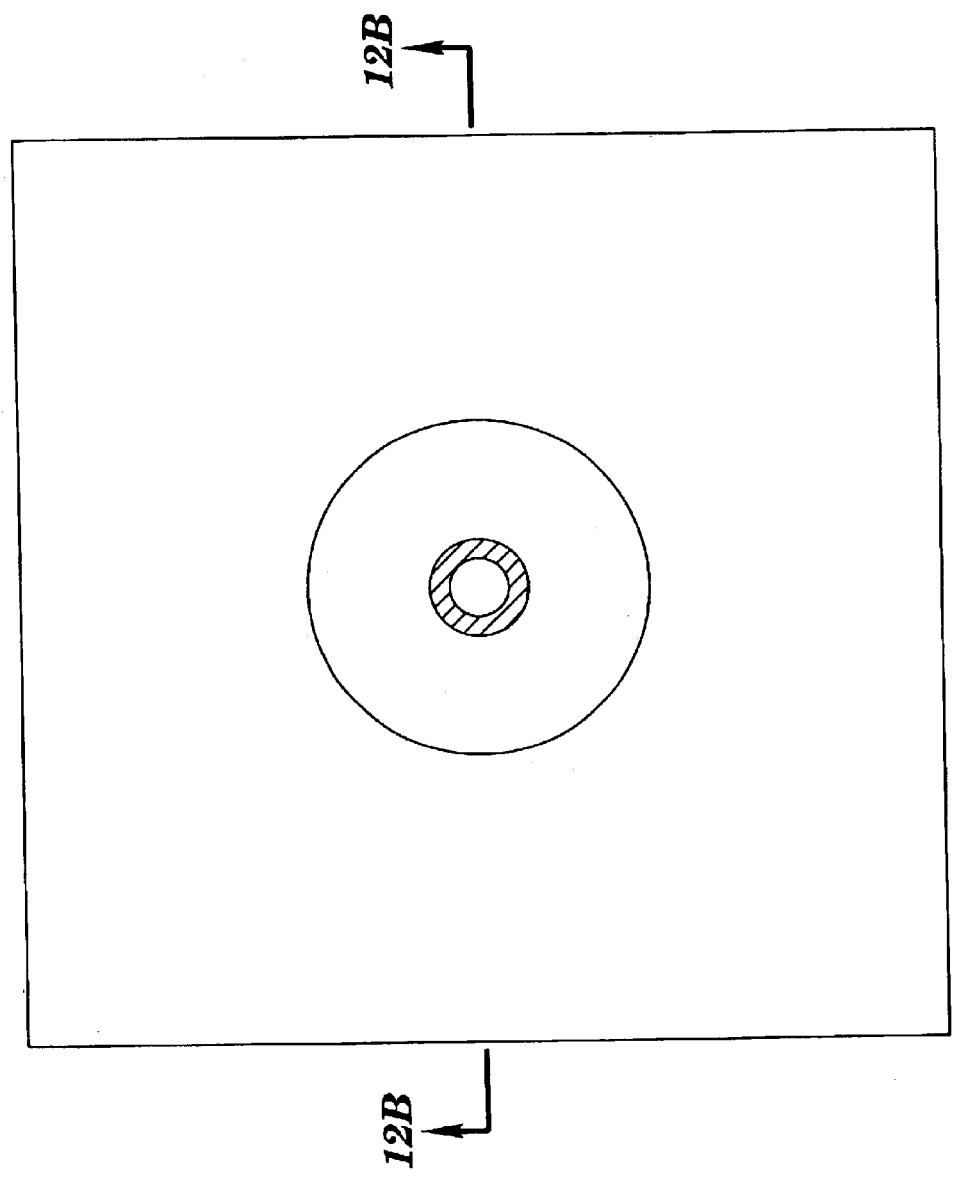
FIGS. 12A–12E show another embodiment of a fabrication sequence of the ejection side of an electrospray device wherein a separate through-substrate alignment channel is incorporated into the device layout.
Figure 12B:
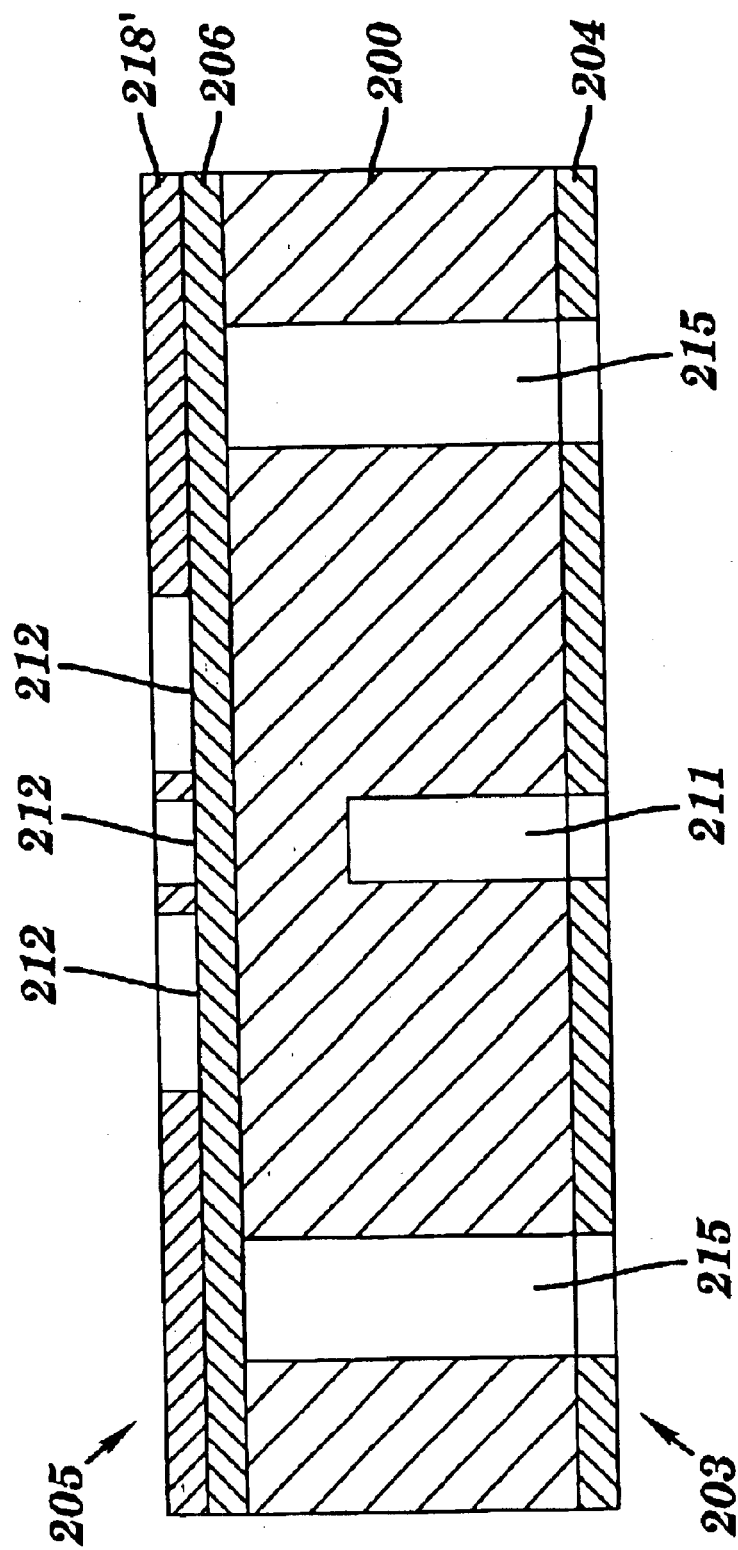
Figure 12C:
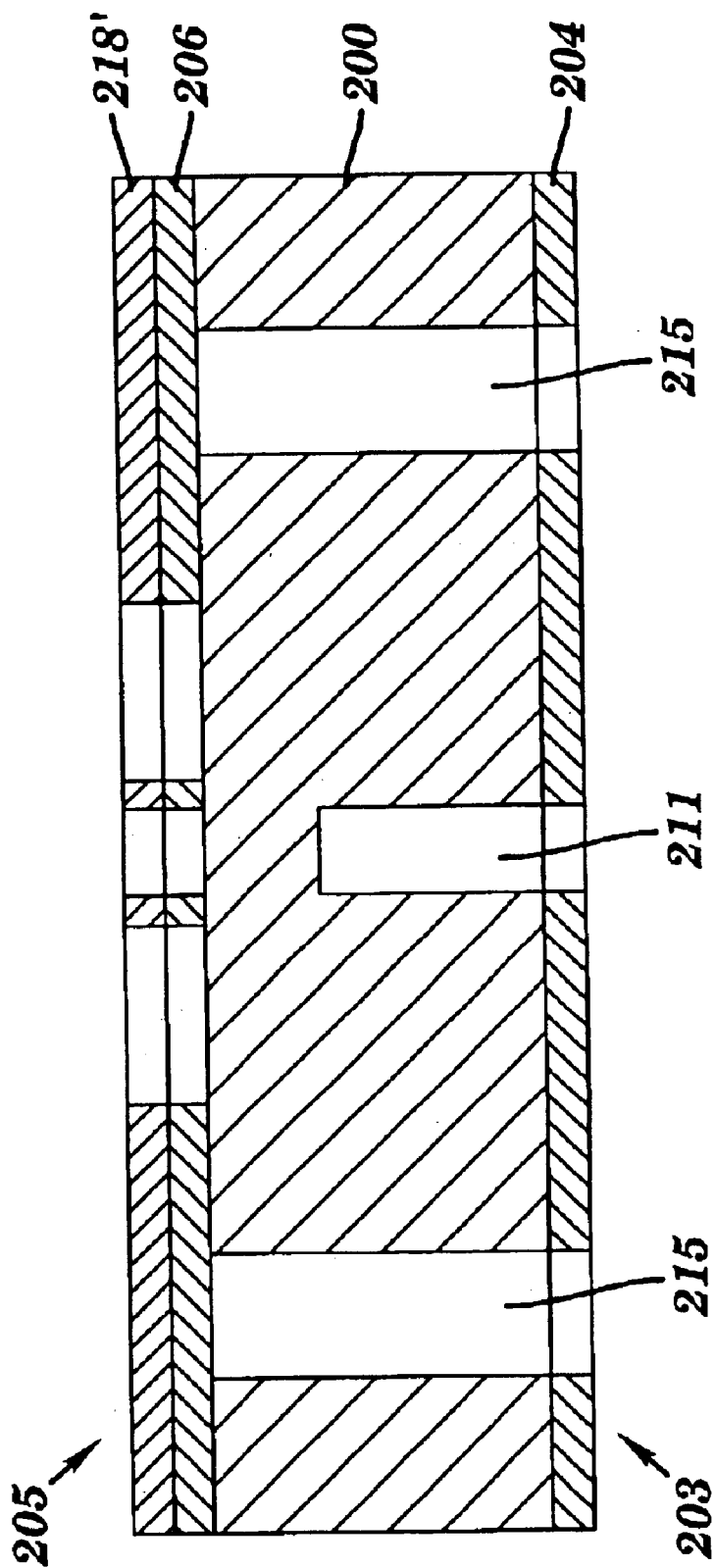

After alignment, areas of the photoresist that define the inner and outer diameter of the nozzle and the outer diameter of the recessed annular region are selectively exposed through an ejection side mask by an optical lithographic exposure tool. As shown in the cross-sectional view of FIG. 12C, the exposed photoresist 218' is then developed to remove the exposed areas of the photoresist such that the device features 212 are open to the underlying silicon dioxide layer 206, while the unexposed areas remain protected by the unexposed photoresist 218'. The exposed areas 212 of the silicon dioxide layer 206 are then etched by a fluorine-based plasma with a high degree of anisotropy and selectivity to the protective photoresist 218' until the silicon substrate 200 is reached as seen in FIG. 12C.

Figure 12D:
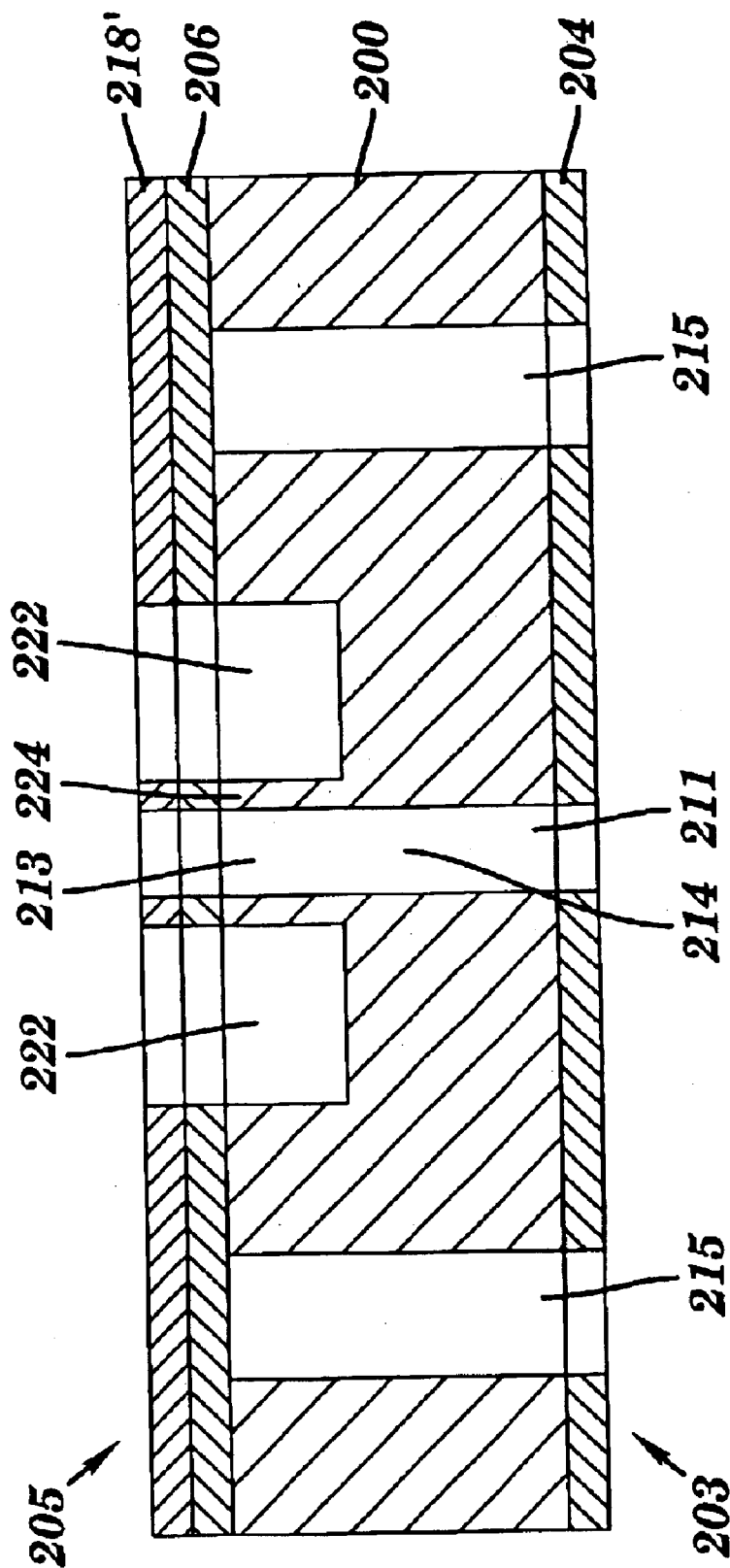
Figure 12E:
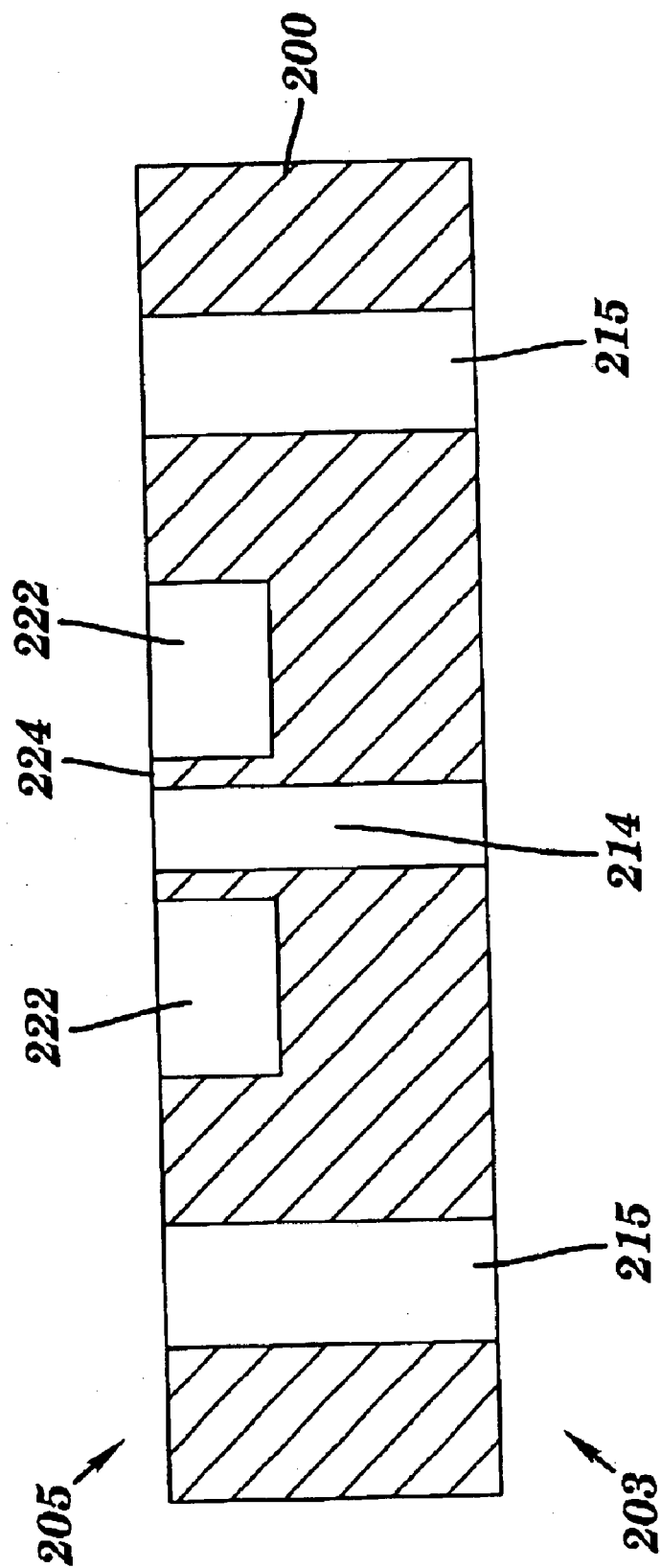

As shown in FIG. 12D, a fluorine-based etch creates an ejection nozzle 224, a recessed annular region 222 exterior to the nozzle and an ejection side channel 213 that is etched until the injection side channel 211 is reached forming the through-substrate channel 214. After the desired depth for the recessed annular region 222 and the nozzle 224 are achieved, the remaining photoresist 218' is then removed in an oxygen plasma or in an actively oxidizing chemical bath like sulfuric acid ($H_2SO_4$) activated with hydrogen peroxide ($H_2O_2$). The silicon dioxide layers 204 and 206 are removed using hydrofluoric acid to open up the through-substrate channel 214 as shown in FIG. 12E.

This fabrication sequence confers superior mechanical stability to the fabricated electrospray device by etching the features of the electrospray device from a monocrystalline silicon substrate without any need for assembly. Further, use of a visible alignment mark as described in the fabrication sequence of this device allows for alignment of injection side and ejection side features to better than 1 μm. This allows for overall nozzle dimensions that are smaller than previously achieved that use prior disclosed alignment schemes using infrared light. Control of the lateral extent and shape of the recessed annular region provides the ability to modify and control the electric field between the electrospray device 100 and an extracting electrode.

Discussed below is another scheme for fabricating a through wafer channel and nozzle. Here, front side to backside alignment of the channel and nozzle is conducted by patterning both injection and ejection sides of the wafer together prior to the etch processing. A double-side polished silicon substrate is subjected to an elevated temperature in an oxidizing environment to grow a layer or film of silicon dioxide on the injection and ejection side of the substrate. The resulting silicon dioxide layer has a thickness of approximately 1–2 μm. The silicon dioxide layer serves as a mask for subsequent selective etching of certain areas of the silicon substrate. A film of positive-working photoresist is deposited on the silicon dioxide layer of the injection and ejection sides of the wafer.

The injection and ejection masks are aligned to each other using an optical lithographic exposure tool. The silicon substrate is positioned between the aligned masks followed by injection and ejection side exposure by an optical lithographic exposure tool. Subsequent processing of the wafer is conducted as described previously.

Preparation of the Substrate for Electrical Isolation

Figure 13:
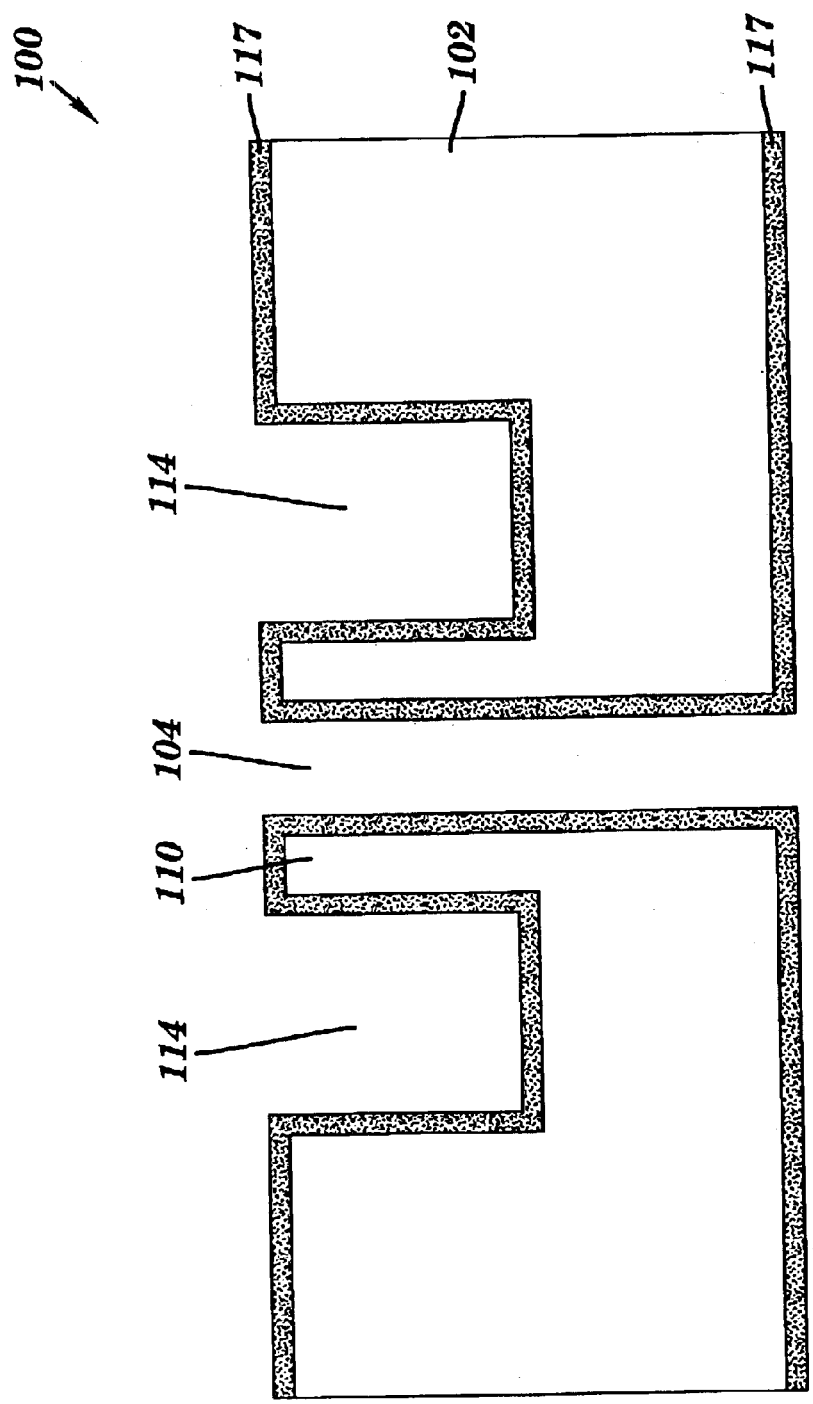
FIG. 13 shows an electrospray device with a sacrificial silicon dioxide layer.
Figure 14:
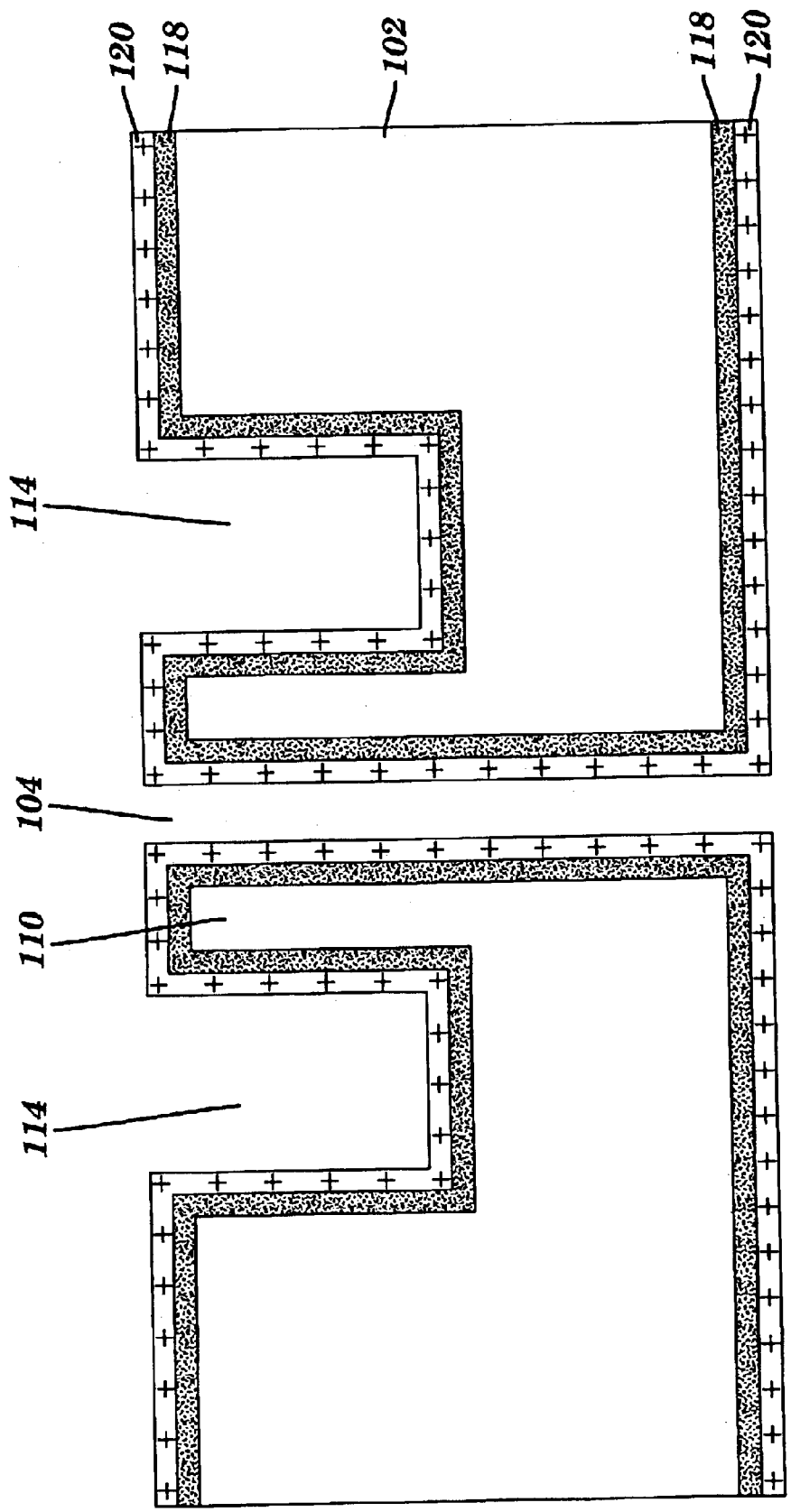
FIG. 14 shows an electrospray device with a silicon dioxide and a silicon nitride layer.
Figure 15:
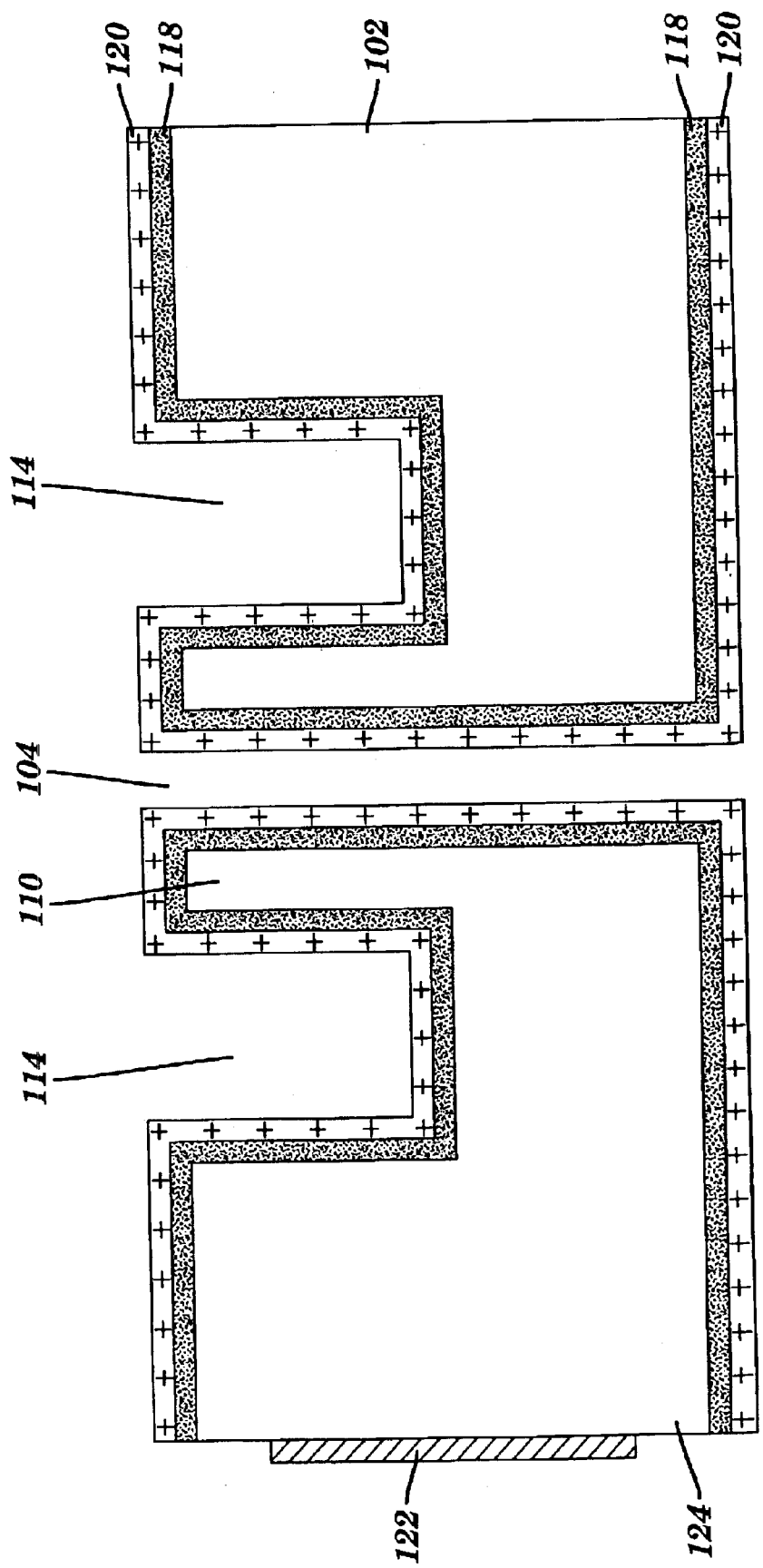
FIG. 15 shows an electrospray device with a silicon dioxide, a silicon nitride layer, and a conductive metal electrode on the edge of the silicon substrate.

As shown in the cross-sectional views of FIGS. 13–15, a layer of silicon dioxide 117 is grown on all silicon surfaces of the substrate 102 by subjecting the silicon substrate to elevated temperature in an oxidizing ambient. This layer is grown to typically less than 1 μm to remove any materials from the surfaces of the substrate. This silicon dioxide layer is removed from the silicon substrate using hydrofluoric acid. The silicon substrate is further subjected to elevated temperature in an oxidizing ambient furnace to grow silicon dioxide 118 to a thickness of 1 to 4 μm. A layer of silicon nitride 120 is further deposited on top of the silicon dioxide layer using low pressure chemical vapor deposition ("LPCVD") providing a conformal coating of silicon nitride on all surfaces up to 2 μm in thickness. The silicon nitride prevents water and ions from penetrating through the silicon dioxide layer, causing an electrical connection between the fluid in the through-wafer channel 104 and the silicon substrate 102. The layers of silicon dioxide 118 and silicon nitride 120 over all surfaces of the substrate, electrically isolates a fluid in the channel 104 from the silicon substrate and permits the application and sustenance of different electrical potentials to the fluid in the channel 104 and to the silicon substrate 102.

All silicon surfaces are oxidized to form silicon dioxide with a thickness that is controllable through choice of temperature and time of oxidation. All silicon dioxide surfaces are LPCVD coated with silicon nitride. The final thickness of the silicon dioxide and silicon nitride can be selected to provide the desired degree of electrical isolation in the device. A thicker layer of silicon dioxide and silicon nitride provides a greater resistance to electrical breakdown. The silicon substrate 100 is divided into the desired size or array of electrospray devices for purposes of metalization of the edge of the silicon substrate. As shown in FIG. 15, the edge 124 of the silicon substrate is coated with a conductive material 122 using well known thermal evaporation and metal deposition techniques.

The above described fabrication sequence for the electrospray device 100 can be easily adapted to and is applicable for the simultaneous fabrication of a single monolithic system comprising multiple electrospray devices including multiple channels and/or multiple ejection nozzles embodied in a single monolithic substrate. Further, the processing steps may be modified to fabricate similar or different electrospray devices merely by, for example, modifying the layout design and/or by changing the polarity of the photomask and utilizing negative-working photoresist rather than utilizing positive-working photoresist.

Liquid Chromatography and Electrospray Device Fabrication Procedure

The fabrication of a liquid chromatography/electrospray ("LC/ESI") device of the present invention is explained with reference to FIGS. 16A–I. The LC/ESI device is preferably fabricated as a monolithic silicon micro device utilizing established, well-controlled thin-film silicon processing techniques such as thermal oxidation, photolithography, reactive-ion etching (RIE), chemical vapor deposition, ion implantation, and metal deposition. Fabrication using such silicon processing techniques facilitates massively parallel processing of similar devices, is time- and cost-efficient, allows for tighter control of critical dimensions, is easily reproducible. and results in a wholly integral device, thereby eliminating any assembly requirements.

Figure 16A:
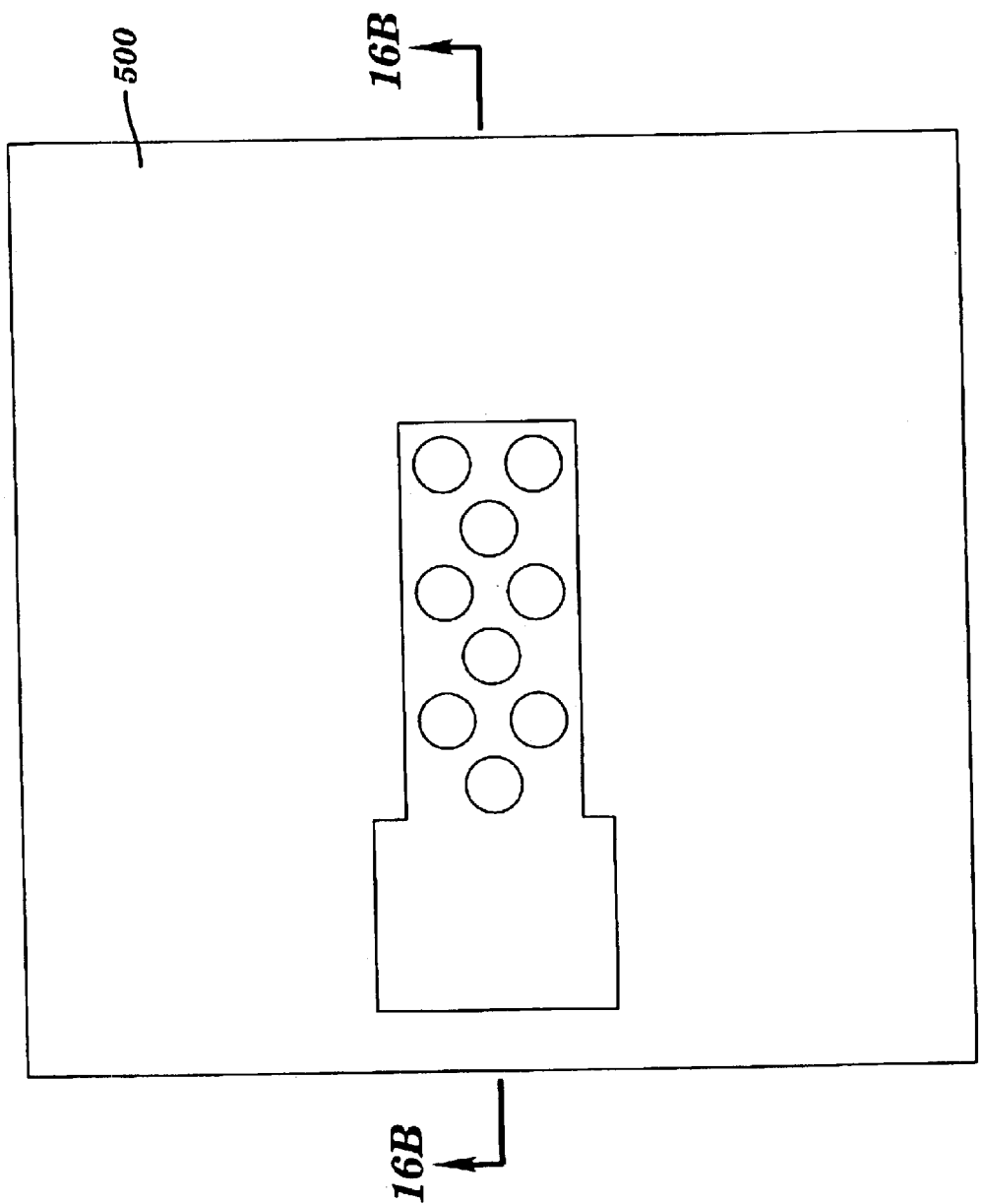
FIGS. 16A–16I show an embodiment of a chromatography side fabrication sequence of an, integrated liquid chromatography-electrospray device.
Figure 16B:
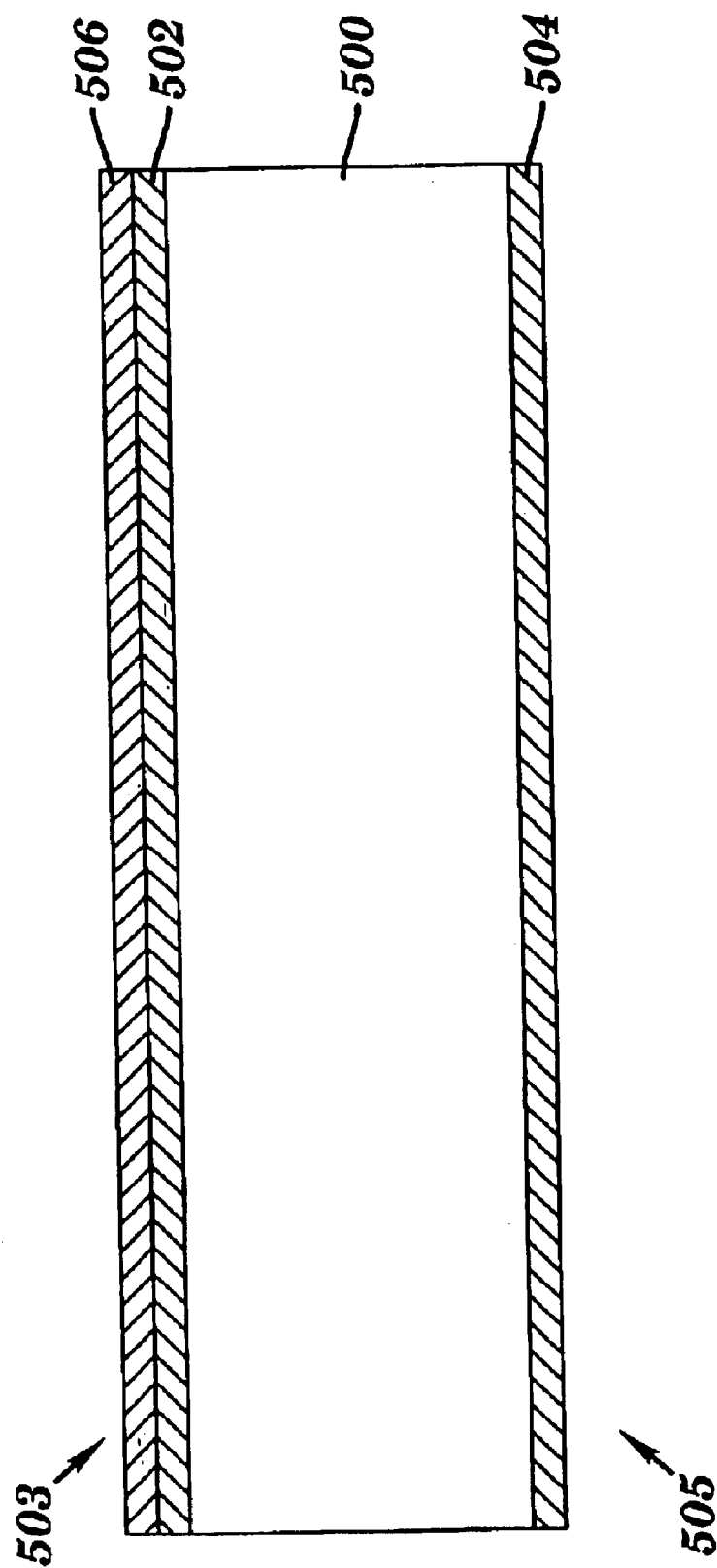

Referring to the plan and cross-sectional views, respectively, of FIGS. 16A and 16B (taken along line 16B—16B of FIG. 16A), a silicon wafer substrate 500, double-side polished and approximately 250–300 $\mu$m in thickness, is subjected to an elevated temperature in an oxidizing ambient to grow a layer or film of silicon dioxide 502 on the chromatography side 503 and a layer or film of silicon dioxide 504 on the electrospray side 505 of the separation substrate 500. Each of the resulting silicon dioxide layers 502 and 504 has a thickness of approximately 1–2 $\mu$m. The silicon dioxide layers 502 and 504 serve as masks for subsequent selective etching of certain areas of the separation substrate 500.

A film of positive-working photoresist 506 is deposited on the silicon dioxide layer 502 on the chromatography side 503 of the separation substrate 500. Certain areas of the photoresist 506 corresponding to the reservoirs, sample injection channels, separation channel and separation posts which will be subsequently etched are selectively exposed through a mask by an optical lithographic exposure tool.

Figure 16C:
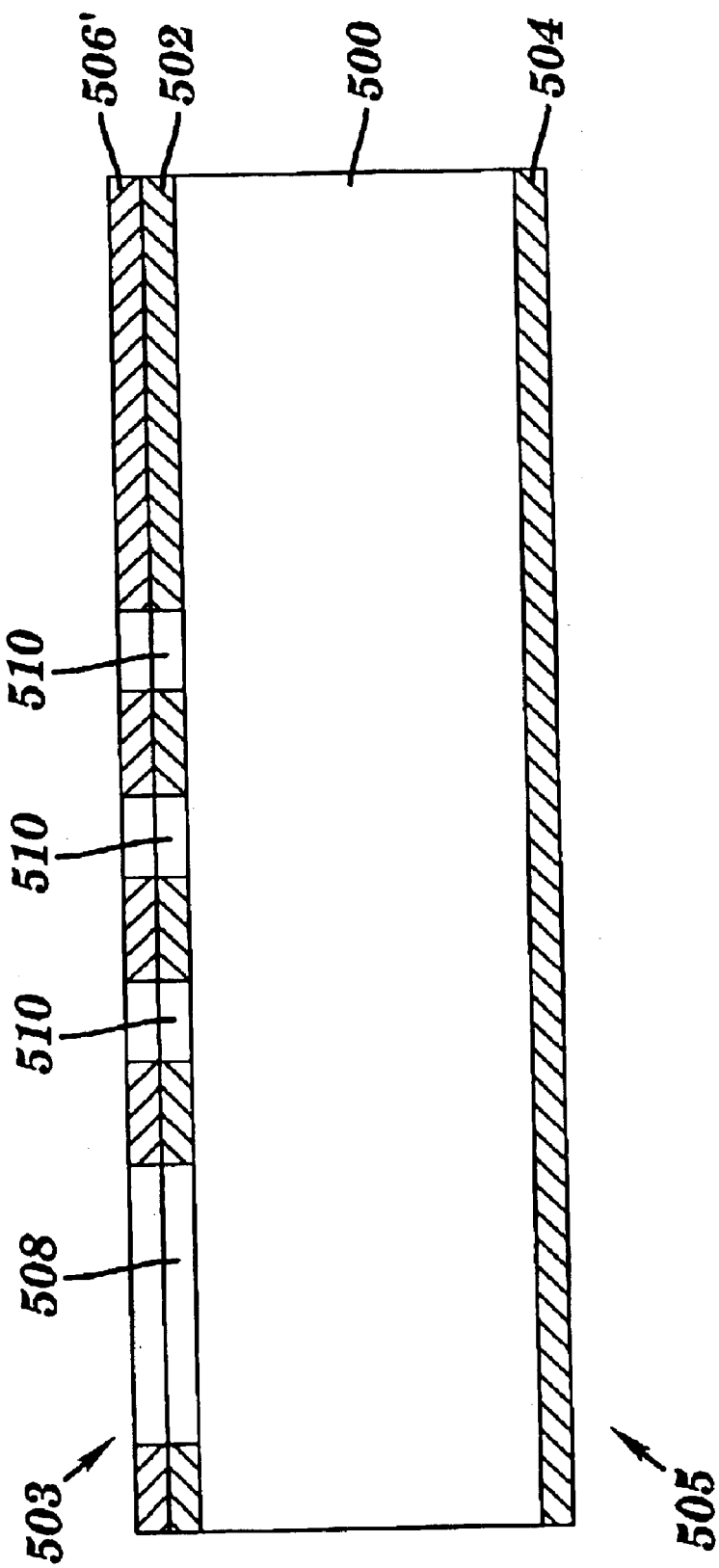

Referring to the cross-sectional view of FIG. 16C, after development of the photoresist 506, the exposed areas of the photoresist corresponding to the reservoir 508 and separation channel 510, respectively, are removed and open to the underlying silicon dioxide layer 502, while the unexposed areas remain protected by photoresist 506'. The exposed areas 508 and 510 of the silicon dioxide layer 502 are then etched by a fluorine-based plasma with a high degree of anisotropy and selectivity to the protective photoresist 506' until the silicon separation substrate 500 is reached. The remaining photoresist is removed in an oxygen plasma or in an actively oxidizing chemical bath like sulfuric acid ($H_2SO_4$) activated with hydrogen peroxide ($H_2O_2$).

Figure 16D:
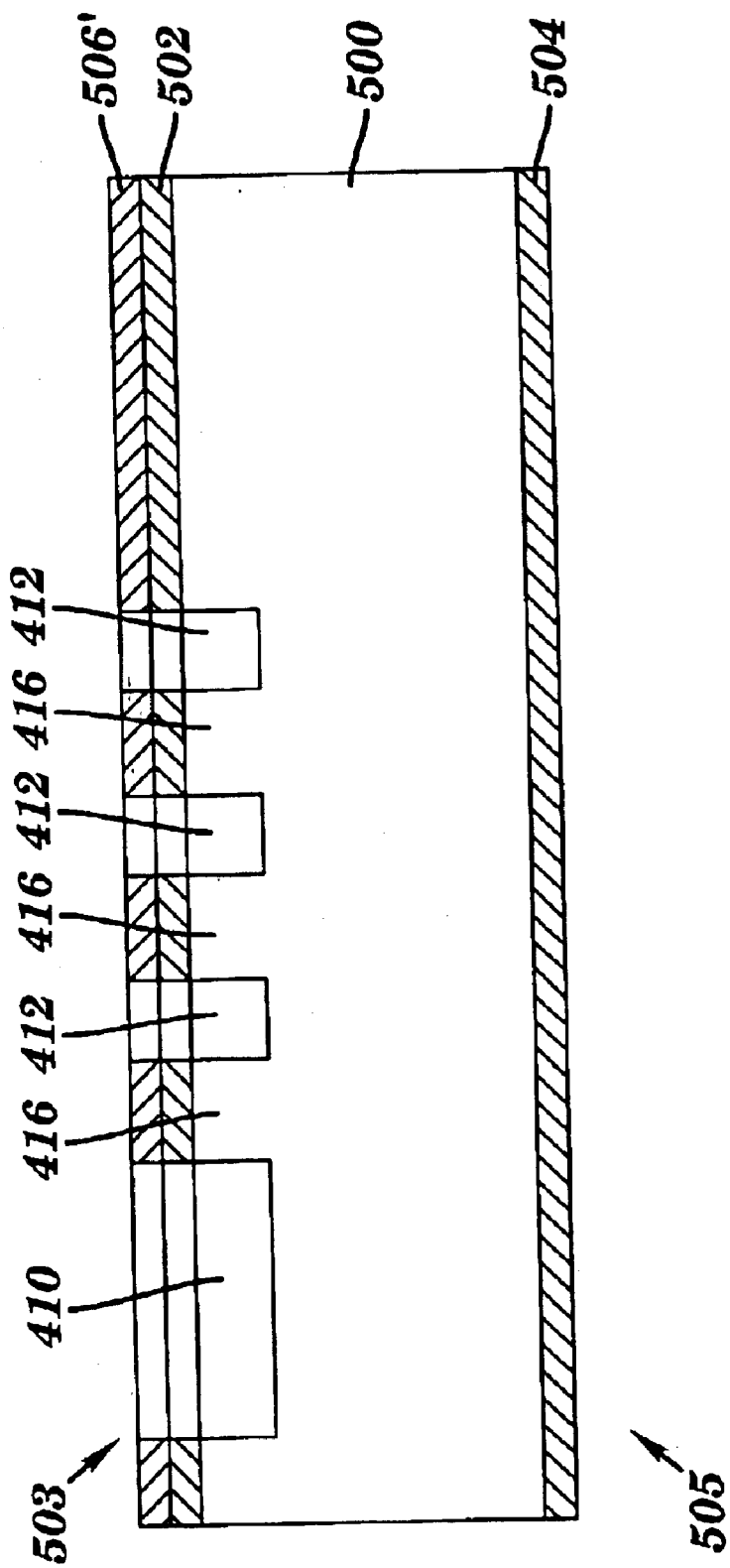

As shown in the cross-sectional view of FIG. 16D, the reservoir 410, the separation channel 412, and the separation posts 416 in the separation channel are vertically formed in the silicon separation substrate 500 by another fluorine-based etch as described in U.S. Pat. No. 5,501,893, which is hereby incorporated by reference. Preferably, the reservoir 410 and the separation channel 412 have the same depth controlled by the etch time at a known etch rate. The depth of the reservoir 410 and the channel 412 is preferably between approximately 5–20 $\mu$m and more preferably approximately 10–15 $\mu$m.

Figure 16E:
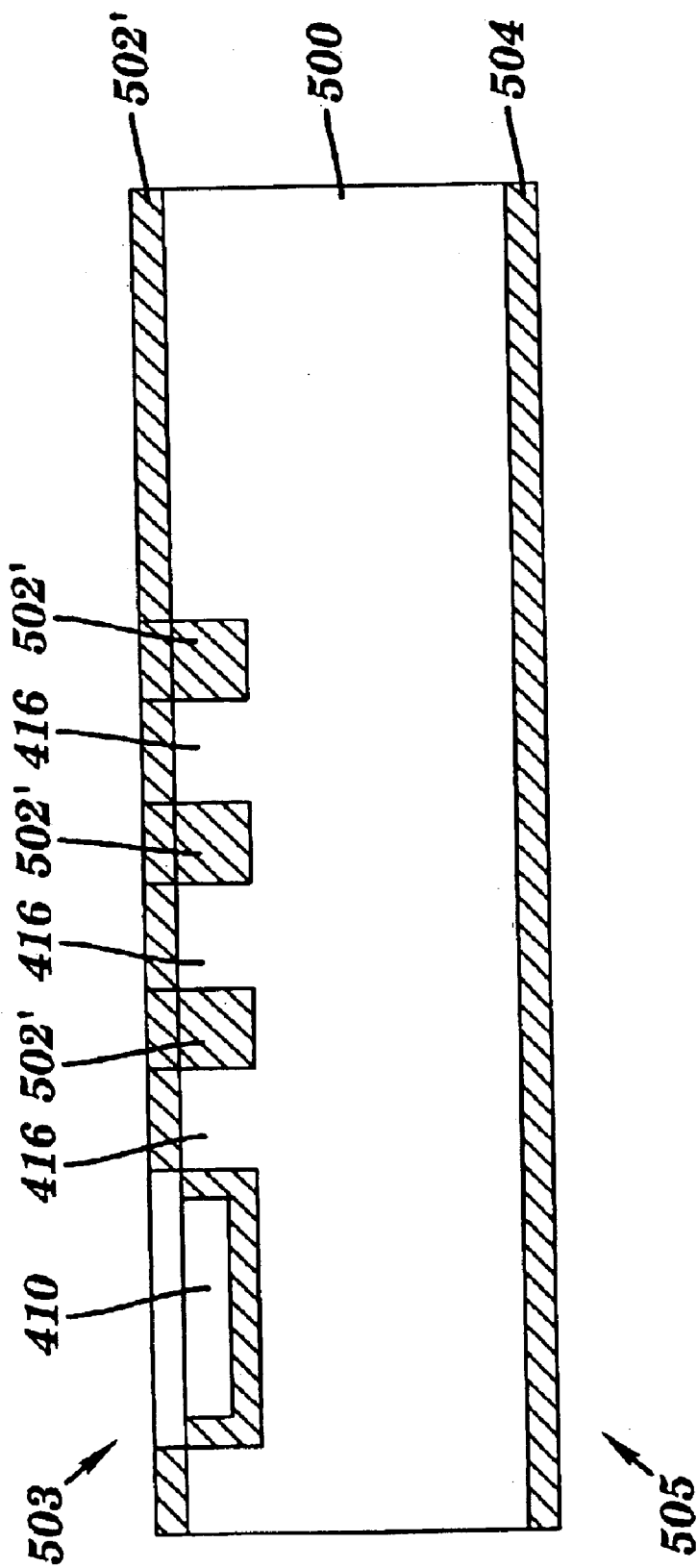

Referring to the cross-sectional view of FIG. 16E, the remaining photoresist 506' is removed and the substrate 500 is subjected to an elevated temperature in an oxidizing ambient to grow a layer or film of silicon dioxide 502' sufficient to minimize the space between the posts 416 created during the previous etch described in FIG. 16D. Alternatively, PECVD silicon dioxide may be deposited on the chromatography side of the substrate sufficient to enclose the space between the posts 416.

Figure 16F:
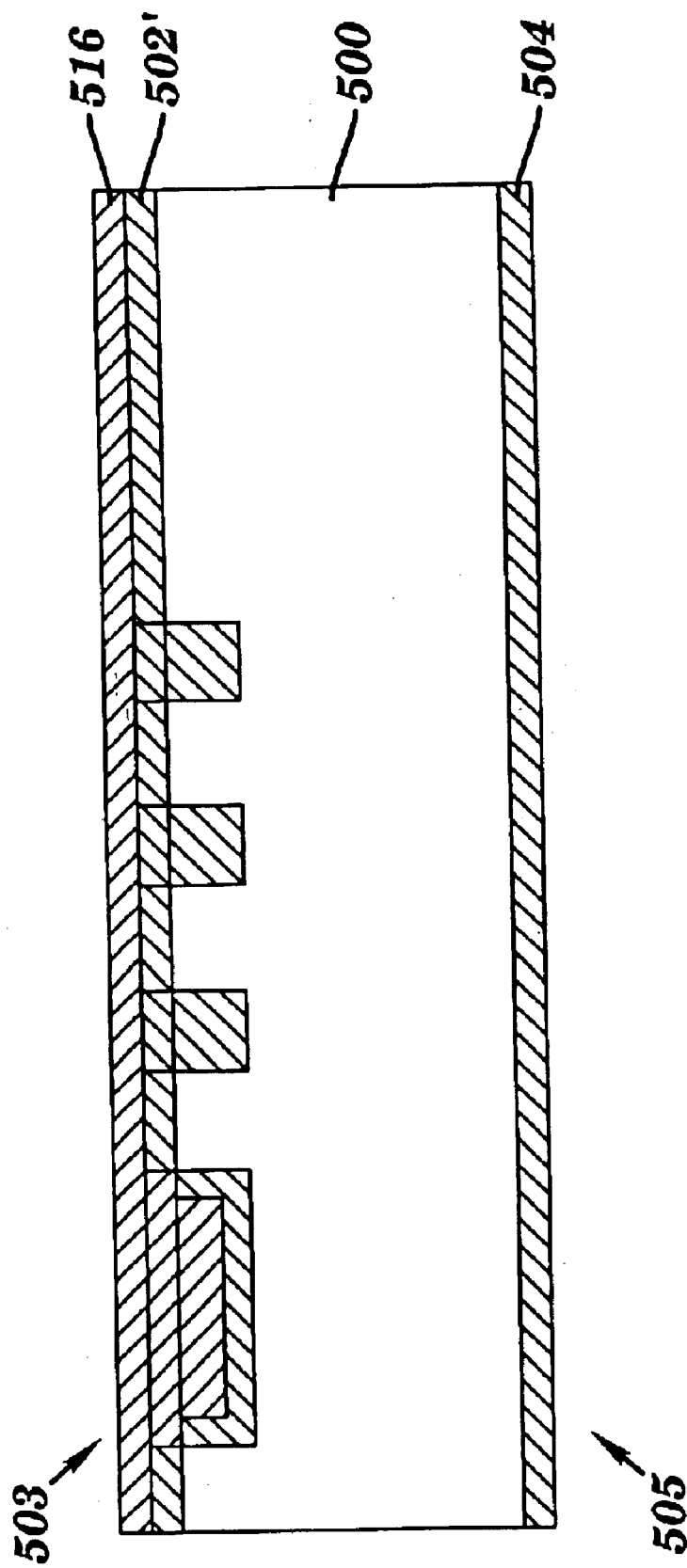
Figure 16G:
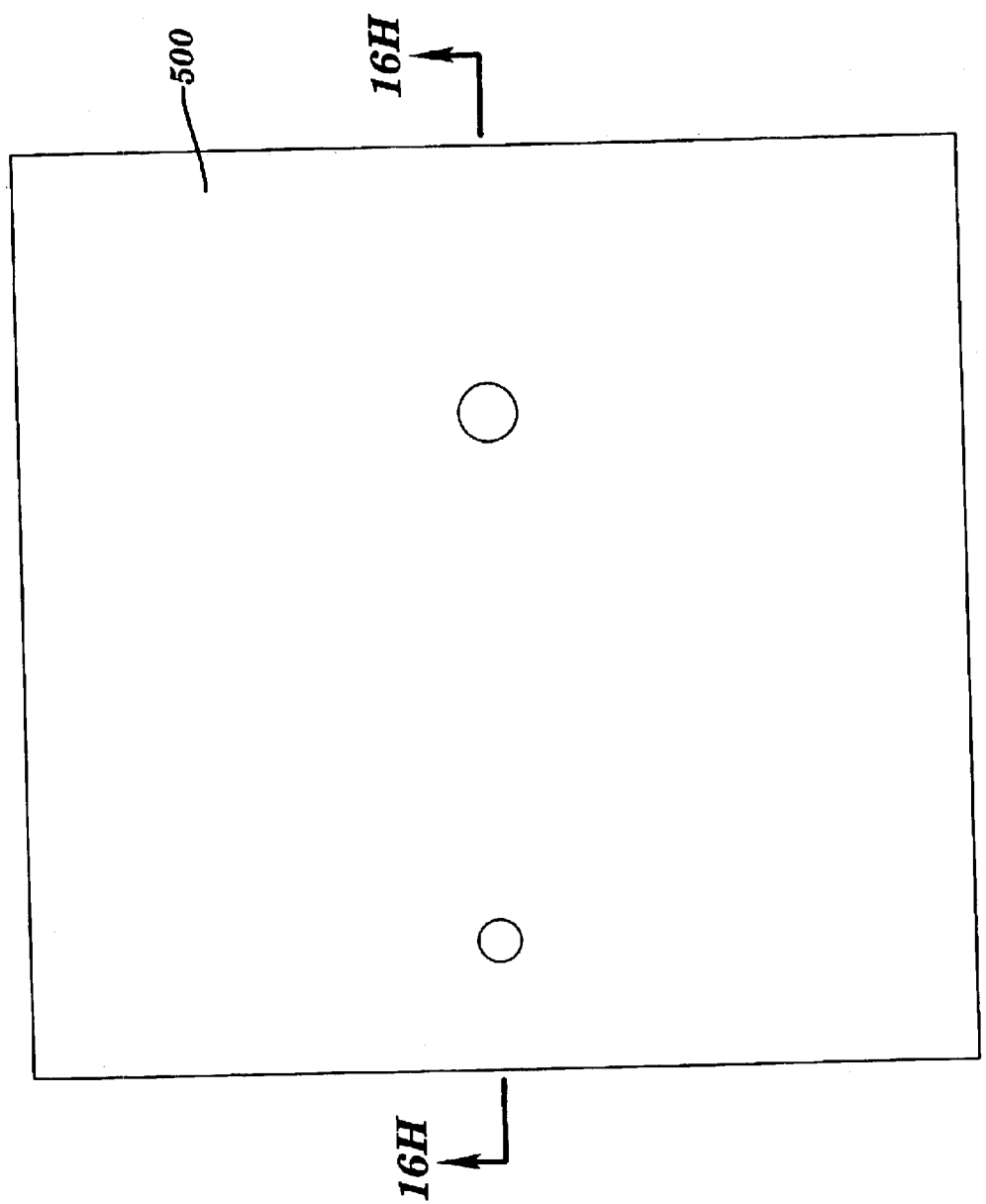
Figure 16H:
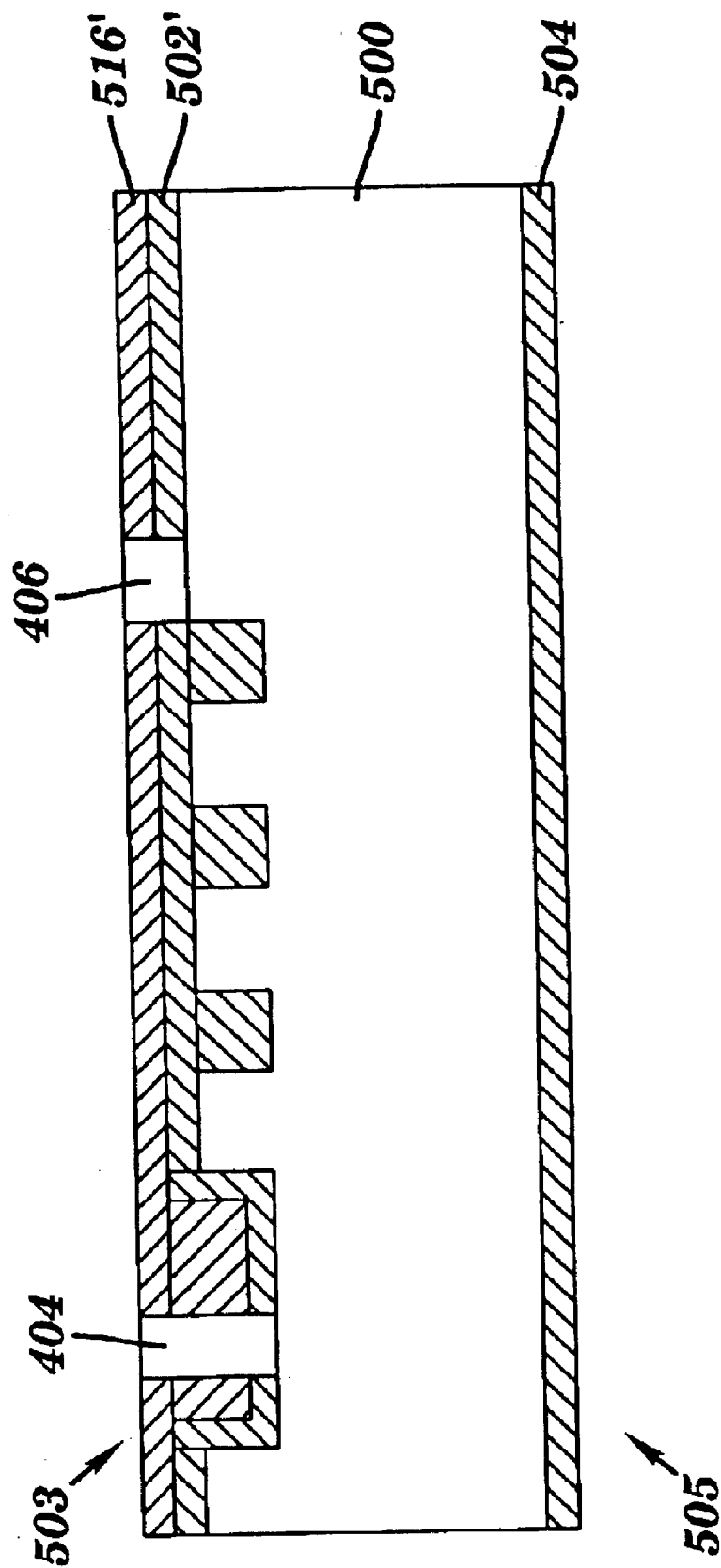

Referring to the cross-sectional view of FIG. 16F, a film of positive-working photoresist 516 is deposited on the silicon dioxide layer 502' on the chromatography side 503 of the separation substrate 500. Referring now to the plan and cross-sectional views of FIGS. 16G and 16H (taken along line 16H—16H of the FIG. 16G), respectively, certain areas of the photoresist 516 corresponding to the reservoir through-substrate channel 404 and the electrospray through-substrate channel 406 that will be subsequently etched are selectively exposed through a mask by an optical lithographic exposure tool. After development of the photoresist 516', the exposed area 518 of the photoresist 516' corresponding to the reservoir through-substrate channel and the electrospray through-substrate channel is removed to expose the underlying silicon dioxide layer 502' of the separation substrate 500. The exposed silicon dioxide layer is then etched by a fluorine-based plasma with a high degree of anisotropy and selectivity to the protective photoresist 516' until the silicon separation substrate 500 is reached. The remaining photoresist is left in place to provide additional masking during the subsequent through-substrate etch of the silicon substrate 500.

Figure 16I:
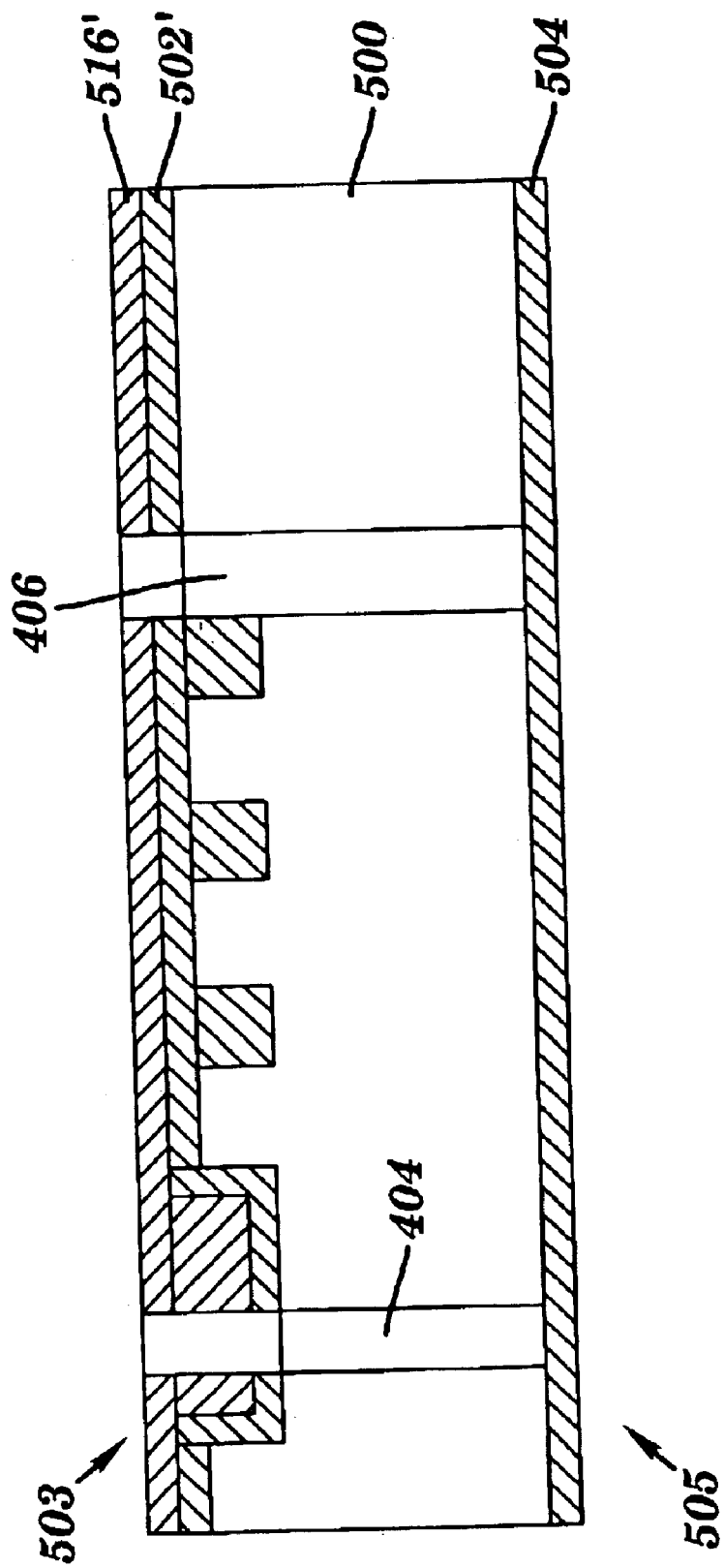

Referring now to the cross-sectional view of FIG. 16I, the reservoir through-substrate channel and the electrospray through-substrate channel is vertically formed through the silicon separation substrate 500 by a fluorine-based etch as described in U.S. Pat. No. 5,501,893, which is hereby incorporated by reference. The reservoir through-substrate channel 404 and the electrospray through-substrate channel 406 are etched until the silicon dioxide layer 504 is reached. The remaining photoresist is removed in an oxygen plasma or in an actively oxidizing chemical bath like sulfuric acid ($H_2SO_4$) activated with hydrogen peroxide ($H_2O_2$).

Figure 17B:
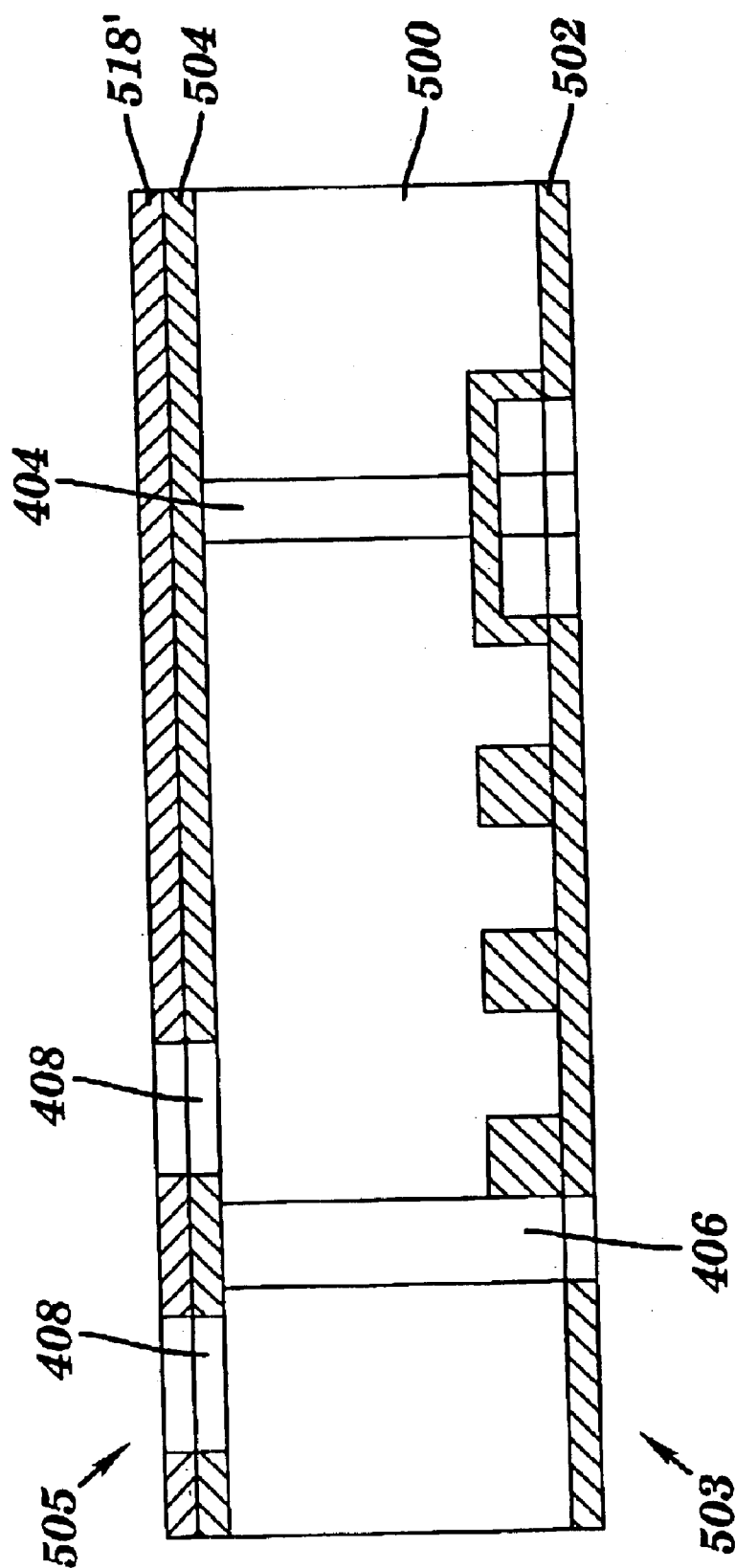

The remaining nozzle and recessed annular region are etched using the same method as that outlined previously in the fabrication of the ejection surface processing of the electrospray device as shown in FIGS. 17A–D. FIG. 17A is a plan view of the pattern that defines the recessed annular region 408 on the electrospray side 505 of the substrate 500. The existing features are aligned to those previously formed on the chromatography side 503 of the substrate using through-substrate alignment channels.

After alignment, areas of the photoresist that define the pattern that defines the recessed annular region 408 on the electrospray side 505 of the substrate 500 are selectively exposed through an ejection side mask by an optical lithographic exposure tool. As shown in the cross-sectional view of FIG. 17B (taken along line 17B—17B of FIG. 17A), the exposed photoresist 518' is then developed to remove the exposed areas of the photoresist to the underlying silicon dioxide layer 504. The exposed areas of the silicon dioxide layer 504 are then etched by a fluorine-based plasma with a high degree of anisotropy and selectivity to the protective photoresist 518' until the silicon substrate 500 is reached.

Figure 17C:
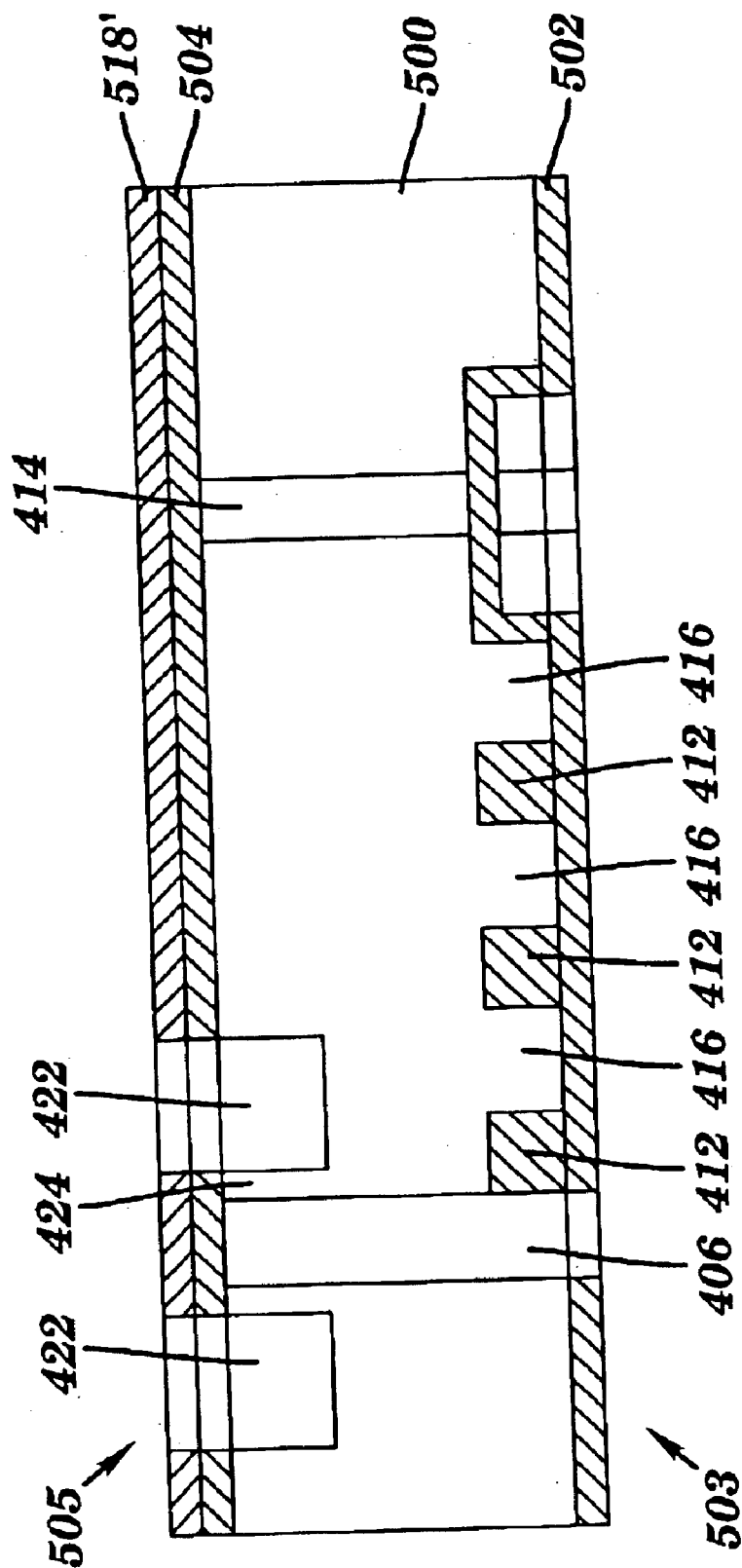
Figure 17D:
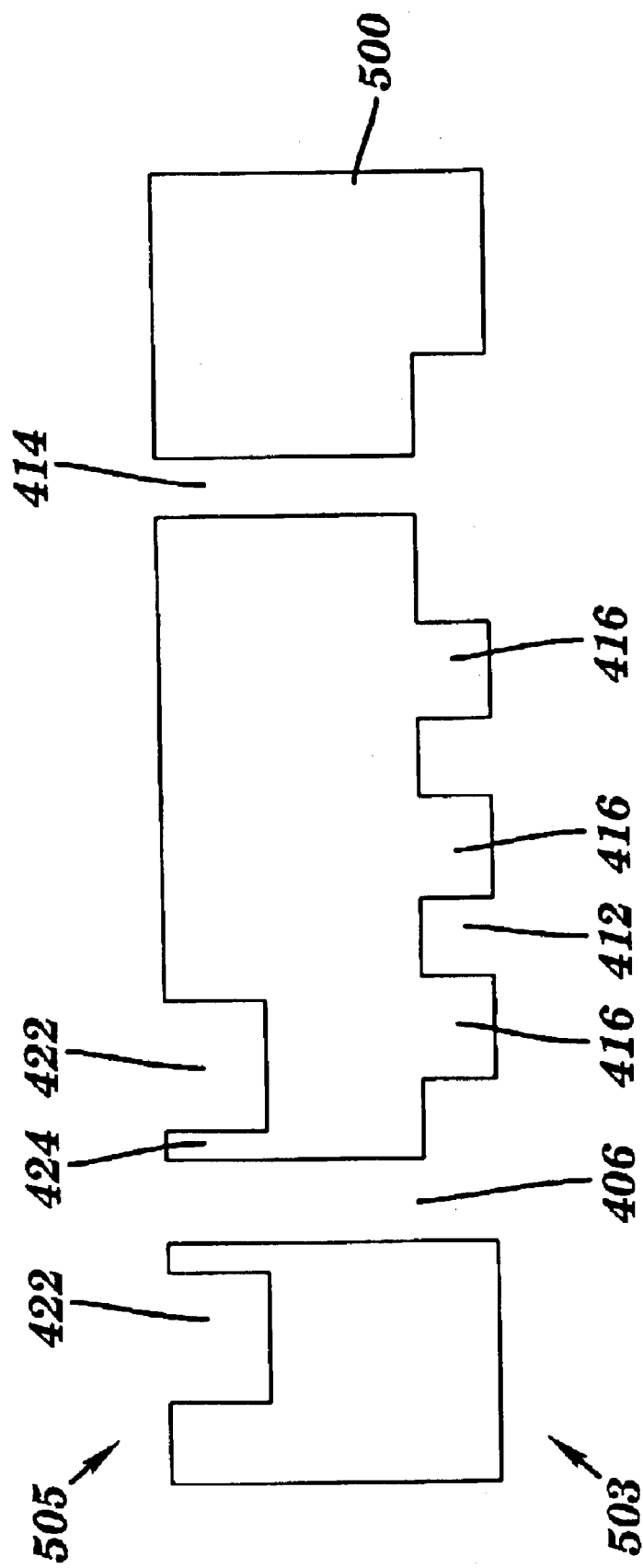

As shown in FIG. 17C, a fluorine-based etch creates an ejection nozzle 424, a recessed annular region 422 exterior to the nozzle. After the desired depth for the recessed annular region 422 and the nozzle 424 are achieved, the remaining photoresist 518' is then removed in an oxygen plasma or in an actively oxidizing chemical bath like sulfuric acid ($H_2SO_4$) activated with hydrogen peroxide ($H_2O_2$). The silicon dioxide layers 502' and 504 are removed using hydrofluoric acid to open up the through-substrate channel as shown in FIG. 17D.

An advantage to defining the reservoir through-substrate channel and the electrospray nozzle on the same side of the completed LC/ESI device is that the backside of the substrate is then free from any features. This substrate may be bonded to another glass or silicon substrate that may be further bonded to a protective package.

Preparation of the Substrate for Electrical Isolation

A layer of silicon dioxide is grown on all silicon surfaces of the substrate by subjecting the silicon substrate to elevated temperature in an oxidizing ambient. This layer is grown to typically less than 1 µm to remove any materials from the surfaces of the substrate. This silicon dioxide layer is removed from the silicon substrate using hydrofluoric acid. The silicon substrate is further subjected to elevated temperature in an oxidizing ambient to grow silicon dioxide 118 to a thickness of 1 to 4 µm. A layer of silicon nitride 122 is further deposited on top of the silicon dioxide layer using low pressure chemical vapor deposition (LPCVD) providing a conformal coating of silicon nitride on all surfaces up to 2 µm in thickness. Alternatively, plasma enhanced chemical vapor deposition can be used to selectively deposit silicon dioxide and/or silicon nitride on vertical surfaces exposed to the plasma. Silicon nitride is well known to prevent water and ions from penetrating through a silicon dioxide layer of silicon devices. The silicon nitride further prevents an electrical connection between the fluid in the LC/ESI device and the silicon substrate 162. The layer of silicon dioxide 118 and silicon nitride 122 over all surfaces of the silicon substrate 162 electrically isolates a fluid in the channel from the substrate 162 and permits the application and sustenance of different electrical potentials to the fluid in the device and to the silicon substrate 200. Additional layers of silicon dioxide can be deposited using LPCVD to allow for chemical modification of silanol groups on the silicon dioxide surface. The final cross-sectional area should be identical along the entire length of the separation channel and the electrospray through-substrate channel.

Electrodes 176 and bond pads in the cover substrate, preferably comprising glass and/or silicon, are deposited using similar well-known thermal evaporation and metal deposition. The cover substrate is preferably hermetically bonded by any suitable method to the separation substrate for containment and isolation of the fluid in the LC/ESI device. Critical considerations in any bonding method include the alignment of features in the separation and the cover substrates to ensure proper functioning of the liquid chromatography device after bonding and the provision in layout design for conductive lead-throughs such as the bond pads and/or metal lines so that the electrodes (if any) are accessible from outside the liquid chromatography device.

The cross-sectional schematic view of FIG. 6C shows a liquid chromatography-electrospray system 160 comprising a liquid chromatography device of the present invention integrated with an electrospray device of the present invention. A homogeneous interface is formed between the exit orifice 170 of the liquid chromatography device and the entrance orifice of the electrospray device. The single integrated system allows for the fluid exiting the exit orifice of the liquid chromatography device to be delivered on-chip to the entrance orifice of the electrospray device in order to generate an electrospray.

Multiple Liquid Chromatography-Electrospray Systems on a Single Chip

Multiples of the liquid chromatography-electrospray system may be formed on a single chip to deliver a multiplicity of samples to a common point for subsequent sequential analysis.

Interface of a Multi-System Chip to Mass Spectrometer

A radially distributed array of electrospray nozzles on a multi-system chip may be interfaced with a sampling orifice of a mass spectrometer by positioning the nozzles near the sampling orifice. The tight radial configuration of electrospray nozzles allows the positioning thereof in close proximity to the sampling orifice of a mass spectrometer.

A multi-system chip may be rotated relative to the sampling orifice to position one or more of the nozzles for electrospray near the sampling orifice. Appropriate voltage(s) may then be applied to the one or more of the nozzles for electrospray. Alternatively, the multi-system chip may be fixed relative to the sampling orifice of a mass spectrometer such that all nozzles, which converge in a relatively tight radius, are appropriately positioned for the electrospray process. As is evident, eliminating the need for nozzle repositioning allows for highly reproducible and quick alignment of the single multi-system chip and increases the speed of the analyses.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of producing an electrospray device comprising:

providing a substrate having opposed first and second surfaces, each coated with a photoresist;

exposing the photoresist on the first surface to an image to form a pattern in the form of a spot on the first surface;

removing the photoresist on the first surface where the pattern is in the form of a hole in the photoresist;

removing material from the substrate coincident with the hole in the photoresist on the first surface to form a channel extending through the photoresist on the first surface and through the substrate up to the photoresist on the second surface;

exposing the photoresist on the second surface to an image to form an annular pattern circumscribing an extension of the channel through the photoresist on the second surface;

removing the photoresist on the second surface where the annular pattern is;

removing material front the substrate coincident with where the pattern in the photoresist on the second surface has been removed to form an annular recess extending partially into the the substrate; and removing all coatings from the first and second surface of the substrate to form the electrospray device.

2. A method according to claim 1, wherein the substrate is silicon and layers of silicon dioxide are present between the coatings of photoresist and the substrate, said method further comprising:

removing the silicon dioxide from the first surface after said removing the photoresist on the first surface and removing the silicon dioxide from the second surface after said removing the photoresist on the second surface.

3. A method of producing an electrospray device comprising:

providing a substrate having opposed lust and second surfaces, each coated with a photoresist;

exposing the photoresist on the first surface to an image to form a pattern in the form of at least 3 substantially aligned spots on the first surface;

removing the photoresist on the first surface where the pattern is in the form of 3 holes in the photoresist corresponding to where the spots in the photoresist were;

removing material from the substrate coincident with where the pattern in the photoresist on the first surface has been removed to faint a central channel aligned with and between two outer channels, said channels extending through the photoresist on the first surface and into the substrate, wherein the central channel has a diameter which is less than that of the outer channels such that the central channel extends farther from the second surface at the substrate than the outer channels which extend up to the photoresist on the the second surface;

exposing the photoresist on the second surface to an image which forms an annular pattern circumscribing a spot, wherein the spot is coincident with an extension of the central channel through the photoresist on the second surface and a portion of the substrate;

removing the photoresist on the second surface where the annular pattern circumscribing the spot is;

removing material from the substrate coincident with where the pattern in the photoresist on the second surface has been removed to form an annular recess extending partially into the substrate which circumscribes the central channel which extends through the substrate and the photoresist on the first and second surfaces;

removing alt coatings from the first and second surfaces of the substrate; and coating all surfaces of the substrate with an insulating material to form the electrospray device.

4. A method according to claim 3, wherein the substrate is silicon and layers or silicon dioxide are present between she coatings of photoresist and the substrate, said method further comprising:

removing the silicon dioxide from the first surface after said removing the photoresist on the first surface and removing the silicon dioxide from the second surface after said removing the photoresist on the second surface.

5. A method according to claim 3, wherein the insulating material is selected from the group consisting of silicone dioxide, silicon nitride, and combinations thereof.

6. A method of forming a liquid separation device comprising:

providing a substrate having opposed first and second surfaces, each coated with a photoresist;

exposing the photoresist on the first surface to an image to form a pattern in the form of a plurality of spots on the first surface;

removing the photoresist on the first surface where the pattern is in she form of a plurality of holes in the photoresist corresponding to where the spots in due photoresist were;

removing material front the substrate coincident with where the pattern in the photoresist on the first surface has been removed to form a large reservoir proximate a first end of the substrate and a plurality of smaller holes closer to a second opposite end or the substrate than the reservoir, said reservoir and holes extending through the photoresist on the first surface and partially into the substrate;

filling the smaller holes and surfaces of the reservoir with a coating;

applying a further photoresist layer over the coating on the surfaces of the reservoir, the filled holes, and the photoresist on the first surface;

exposing the further photoresist to an image to form a pattern in the form of spots, with one spot coincident with what was part of the reservoir and the other spot being closer to the second end of the substrate than the filled holes;

removing the further photoresist where the pattern is to form holes corresponding to where the spots in the photoresist were;

removing material from the substrate coincident with where the pattern in the further photoresist has been removed to form a pair of channels, with a first channel extending through what was the reservoir up to the photoresist on the second surface and a second channel extending through the substrate up to the photoresist on the second surface at a location closer to the second end of the substrate than the filled holes; and removing all coatings from the first and second surfaces of the substrate; and coating all surfaces of the substrate with an insulating material to form the liquid separation device.

7. A method according to claim 6, wherein, between said removing material from the substrate coincident with where the pattern in the further photoresist has been removed and said removing all coatings, said method further comprises:

exposing the photoresist on the second surface to an image which forms an annular pattern circumscribing on extension of the first channel through the photoresist on the second surface;

removing the photoresist on the second surface where the annular pattern is; and removing material from the substrate coincident with where the pattern in the photoresist on the second surface has been removed to form an annular recess extending partially into the substrate which circumscribes the first channel which extends through the substrate and the photoresist on the first and second surfaces.

8. A method according to claim 7, wherein the substrate is silicon and layers of silicon dioxide are present between the coatings of photoresist and the substrate, said method further comprising:

removing the silicon dioxide from the first surface after said removing the photoresist on the first surface and removing the silicon dioxide from the second surface after said removing the photoresist on the second surface.

9. A method according to claim 6, wherein the insulating material as selected from the group consisting of silicone dioxide, silicon nitride, and combinations thereof.

10. A method according to claim 6, wherein said removing material from the substrate further define posts in the substrate.

11. A method according to claim 10, wherein posts are silicon, said method further comprising:

oxidizing the silicon posts to produce silicon dioxide posts.

* * * * *